United States Patent
Kapas et al.

(10) Patent No.: US 10,441,714 B2
(45) Date of Patent: Oct. 15, 2019

(54) PROTECTIVE CASE FOR AN AUTO-INJECTOR

(71) Applicant: Pirouette Medical LLC, Boston, MA (US)

(72) Inventors: Elijah Kapas, Medford, MA (US); Matthew Kane, Somerville, MA (US); Conor Cullinane, Hampton, NH (US)

(73) Assignee: Pirouette Medical LLC, Boston, MA (US)

( * ) Notice: Subject to any disclaimer, the term of this patent is extended or adjusted under 35 U.S.C. 154(b) by 0 days.

(21) Appl. No.: 16/152,934

(22) Filed: Oct. 5, 2018

(65) Prior Publication Data
US 2019/0105442 A1 Apr. 11, 2019

Related U.S. Application Data

(60) Provisional application No. 62/574,405, filed on Oct. 19, 2017, provisional application No. 62/568,567, filed on Oct. 5, 2017.

(51) Int. Cl.
*A61M 5/00* (2006.01)
*A61M 5/142* (2006.01)
(Continued)

(52) U.S. Cl.
CPC .......... *A61M 5/14248* (2013.01); *A47J 41/02* (2013.01); *A61M 5/002* (2013.01);
(Continued)

(58) Field of Classification Search
CPC .......... A61B 2050/0052; B65D 81/383; B65D 81/81; B65D 81/3834; G01N 2001/005; Y10T 428/231; F25D 2201/14
See application file for complete search history.

(56) References Cited

U.S. PATENT DOCUMENTS

| 1,560,375 A | 11/1925 | Blackman |
| 3,074,541 A | 1/1963 | Roehr |

(Continued)

FOREIGN PATENT DOCUMENTS

| DE | 19725203 C2 | 10/2002 |
| DE | 202013105855 U1 | 1/2014 |

(Continued)

OTHER PUBLICATIONS https://www.linkedin.com/pulse/epibracelet-a-wearable-portable-fashionable-automatic-langan-m-d-/.
(Continued)

*Primary Examiner* — Brian D Nash

(74) *Attorney, Agent, or Firm* — Goodwin Procter LLP

(57) ABSTRACT

The application describes a protective case for an auto-injector. The medicament contained within these auto-injectors can be susceptible to degradation due to exposure to extreme temperatures and light. Thus, one embodiment of the protective case reduces the rate of heat transfer between the internal storage compartment of the case and the external atmosphere by including particularly configured vacuum chambers. Additionally, as auto-injectors become smaller, portability can be desirable. Thus, another embodiment of the protective case includes low-profile cases that allow the user to keep the auto-injector with them, e.g., by attaching the case to a common everyday item.

30 Claims, 74 Drawing Sheets

(51) Int. Cl.
  *A61M 5/32* (2006.01)
  *A47J 41/02* (2006.01)
  *A61M 5/20* (2006.01)

(52) U.S. Cl.
  CPC .......... *A61M 5/20* (2013.01); *A61M 5/3287* (2013.01); *A61M 2005/1426* (2013.01); *A61M 2005/14252* (2013.01); *A61M 2005/2006* (2013.01); *A61M 2209/06* (2013.01)

(56) References Cited

U.S. PATENT DOCUMENTS

| | | | |
|---|---|---|---|
| 3,193,126 A | 7/1965 | Bramming | |
| 4,287,943 A | 9/1981 | Hotta | |
| 4,429,793 A | 2/1984 | Ehmann | |
| 4,573,581 A | 3/1986 | Galloway et al. | |
| 4,738,364 A | 4/1988 | Yeager | |
| 5,015,235 A | 5/1991 | Crossman | |
| 5,107,649 A * | 4/1992 | Benson | A47J 27/002 52/309.4 |
| 5,361,603 A | 11/1994 | Merritt-Munson | |
| 5,390,791 A | 2/1995 | Yeager | |
| 5,405,012 A | 4/1995 | Shindler et al. | |
| 5,658,259 A | 8/1997 | Pearson et al. | |
| 5,714,217 A | 2/1998 | Andersen et al. | |
| 5,858,001 A | 1/1999 | Tsals et al. | |
| 5,934,099 A * | 8/1999 | Cook | A61J 1/165 206/570 |
| 5,950,827 A | 9/1999 | Odom et al. | |
| 5,983,661 A | 11/1999 | Wiesman | |
| 6,086,562 A | 7/2000 | Jacobsen et al. | |
| 6,336,340 B1 | 1/2002 | Laby | |
| 6,405,556 B1 | 6/2002 | Bucholz | |
| 6,508,391 B2 | 1/2003 | Gilbert | |
| 6,595,362 B2 | 7/2003 | Penney et al. | |
| 6,605,067 B1 | 8/2003 | Larsen | |
| 6,780,426 B2 | 8/2004 | Zhang et al. | |
| 6,935,133 B2 | 8/2005 | Keeter et al. | |
| 6,984,222 B1 | 1/2006 | Hitchins et al. | |
| 7,047,983 B2 | 5/2006 | Manougian et al. | |
| 7,434,686 B2 | 10/2008 | Prindle | |
| 7,597,196 B2 | 10/2009 | Langone | |
| 7,686,786 B2 | 3/2010 | Moller et al. | |
| 8,137,314 B2 | 3/2012 | Mounce et al. | |
| 8,152,771 B2 | 4/2012 | Mogensen et al. | |
| 8,298,173 B2 | 10/2012 | Bates et al. | |
| 8,323,250 B2 | 12/2012 | Chong et al. | |
| 8,424,317 B2 * | 4/2013 | Dain | F16L 59/065 62/100 |
| 8,517,988 B2 | 8/2013 | Smith | |
| 8,684,968 B2 | 4/2014 | Genosar | |
| 8,734,396 B2 | 5/2014 | Wyss | |
| 8,753,310 B2 | 6/2014 | Sullivan et al. | |
| 8,932,254 B2 | 1/2015 | Eaton | |
| 9,072,838 B2 | 7/2015 | Hogdahl | |
| 9,096,364 B2 | 8/2015 | Rust et al. | |
| 9,168,337 B2 | 10/2015 | Miyazaki | |
| 9,174,002 B2 | 11/2015 | Chang et al. | |
| 9,220,837 B2 | 12/2015 | Pesach et al. | |
| 9,227,023 B2 | 1/2016 | Kraft | |
| D758,712 S * | 6/2016 | Ladegast | D3/203.1 |
| 9,381,294 B2 | 7/2016 | Ziegner | |
| 9,408,984 B2 | 8/2016 | Durack et al. | |
| 9,480,792 B2 | 11/2016 | Constantineau et al. | |
| 9,486,616 B2 | 11/2016 | Eppstein et al. | |
| 9,533,105 B2 | 1/2017 | Veasey et al. | |
| 9,590,683 B2 | 3/2017 | Greiner | |
| 9,597,450 B2 | 3/2017 | Cindrich et al. | |
| 9,676,522 B1 * | 6/2017 | Stovall | B65D 25/42 |
| 9,707,156 B2 | 7/2017 | Wengreen et al. | |
| 9,750,892 B2 | 9/2017 | Radmer et al. | |
| 10,265,471 B2 * | 4/2019 | Kapas | A61M 5/2033 |
| 2002/0091357 A1 | 7/2002 | Trautman et al. | |
| 2004/0211806 A1 | 10/2004 | Wilkerson et al. | |
| 2005/0222539 A1 | 10/2005 | Gonzales et al. | |
| 2005/0279664 A1 | 12/2005 | Hommann | |
| 2007/0125677 A1 | 6/2007 | Oronsky et al. | |
| 2008/0295833 A1 | 12/2008 | Rohrschneider et al. | |
| 2010/0187270 A1 | 7/2010 | Puglisi | |
| 2010/0270315 A1 | 10/2010 | Davis | |
| 2010/0282762 A1 | 11/2010 | Leonard | |
| 2011/0083445 A1 | 4/2011 | Heyd et al. | |
| 2011/0276027 A1 | 11/2011 | Trautman et al. | |
| 2012/0191102 A1 | 7/2012 | Matsumoto et al. | |
| 2012/0310175 A1 | 12/2012 | Vedrine et al. | |
| 2012/0318808 A1 * | 12/2012 | McCormick | F16L 59/065 220/592.21 |
| 2013/0043285 A1 * | 2/2013 | Cordray | A45C 11/20 224/148.3 |
| 2014/0088508 A1 | 3/2014 | Ryan et al. | |
| 2014/0090997 A1 | 4/2014 | Dasbach et al. | |
| 2014/0138402 A1 | 5/2014 | Warren et al. | |
| 2014/0142507 A1 | 5/2014 | Armes | |
| 2014/0166528 A1 | 6/2014 | Bianchi | |
| 2014/0166654 A1 * | 6/2014 | Lane | A47G 19/2272 220/262 |
| 2014/0309591 A1 | 10/2014 | Holmqvist | |
| 2015/0158658 A1 * | 6/2015 | Anelevitz | A47G 19/2227 220/592.24 |
| 2015/0166244 A1 * | 6/2015 | Wood | B65D 81/18 220/592.25 |
| 2015/0314117 A1 | 11/2015 | Arami et al. | |
| 2015/0343151 A1 | 12/2015 | Stefansen | |
| 2016/0030284 A1 | 2/2016 | Vedrine | |
| 2016/0038689 A1 | 2/2016 | Lee et al. | |
| 2016/0067144 A1 * | 3/2016 | Chang | A61M 5/19 |
| 2016/0153625 A1 * | 6/2016 | Maglica | F21L 4/045 362/187 |
| 2016/0175524 A1 | 6/2016 | Henderson et al. | |
| 2016/0237752 A1 | 8/2016 | Jones | |
| 2016/0251140 A1 * | 9/2016 | Wengreen | B65B 63/08 62/457.2 |
| 2016/0287791 A1 | 10/2016 | Olson | |
| 2016/0296710 A1 | 10/2016 | Bainton et al. | |
| 2017/0056579 A1 | 3/2017 | Muri | |
| 2017/0143896 A1 | 5/2017 | Lorenzen et al. | |
| 2017/0143900 A1 | 5/2017 | Rioux et al. | |
| 2017/0175859 A1 | 6/2017 | Brockmeier | |
| 2017/0209643 A1 | 7/2017 | Geipel et al. | |
| 2017/0297805 A1 * | 10/2017 | Yaguchi | A23G 9/22 |
| 2017/0343247 A1 * | 11/2017 | Ahmad | F25B 9/04 |
| 2018/0214343 A1 * | 8/2018 | Cantor | A61J 1/165 |
| 2019/0060569 A1 * | 2/2019 | Kapas | A61M 5/2033 |

FOREIGN PATENT DOCUMENTS

| | | |
|---|---|---|
| JP | 2008237589 A | 10/2008 |
| WO | WO-1997039787 A1 | 10/1997 |
| WO | WO-2001087739 A1 | 11/2001 |
| WO | WO-2007051563 A1 | 5/2007 |
| WO | WO-2009062510 A1 | 5/2009 |
| WO | WO-2011012849 A1 | 2/2011 |
| WO | WO-2012058192 A1 | 5/2012 |
| WO | WO-2013147440 A1 | 10/2013 |
| WO | WO-2014072993 A3 | 7/2014 |
| WO | WO-2016055505 A1 | 4/2016 |
| WO | WO-2017072333 A1 | 5/2017 |
| WO | WO-2017083622 A1 | 5/2017 |
| WO | WO-2017118681 A1 | 7/2017 |
| WO | WO-2018181291 A1 | 10/2018 |

OTHER PUBLICATIONS http://www.enableinjections.com/.
International Search Report and Written Opinion issused for PCT/US2018/054615, dated Jan. 28, 2019.

* cited by examiner

| Exemplary Properties for Protective Cases | | |
|---|---|---|
| Description | Noted Value | Notes |
| Maximum Pressure for Thermally Isolated Case | 0.1 torr | PRESSURE WITHIN THE SEALED VACUUM CHAMBER CAN BE LESS THAN OR EQUAL TO 0.1 torr |
| High Aspect Ratio (A.R) | A.R > 1 | Width / Height > 1 |
| Low Aspect Ratio (A.R) | A.R < 1 | Width / Height < 1 |

FIG. 133

PROTECTIVE CASE FOR AN AUTO-INJECTOR

CROSS-REFERENCE TO RELATED APPLICATIONS

This application claims priority to and the benefit of U.S. Provisional Patent Application No. 62/574,405, titled "Protective Case for an Auto-Injector," which was filed on Oct. 19, 2017, and U.S. Provisional Patent Application No. 62/568,567, titled "Protective Case for an Auto-Injector," which was filed on Oct. 5, 2017, the disclosures of both of which are herein incorporated by reference in their entireties.

TECHNICAL FIELD

In general, various embodiments of this invention relate to protective cases for drug or biological delivery devices and, specifically, to protective cases forming a vacuum sealed chamber that provides thermal isolation for the enclosed device.

BACKGROUND

The auto-injector market is growing rapidly through an increase in prescriptions, along with new indications for use. Patients are actively seeking solutions to address the anxiety associated with the existing pain points of using protective cases, including poor portability, unwanted attention, and temperature susceptibility.

Existing protective cases address some of the patient's anxieties, but fall short on others and often leave the patients seeking out alternatives. Accordingly, an improved protective case is needed.

SUMMARY

Various embodiments of the invention described herein feature a protective auto-injector case that addresses some of the shortcomings of conventional devices. The auto-injector case can be portable, adaptable, and low-profile. The auto-injector case can also increase the time a patient can maintain their auto-injector device in an adverse climate, as compared to a device without the case. Furthermore, the auto-injector case can allow the patient to prioritize their needs and determine which configuration of the protective case is best for them.

Proposed herein is a protective case adapted for both low and high aspect ratio auto-injectors. As depicted in FIG. 1, the aspect ratio is calculated by dividing the width by the height. The width of the device is measured as the smallest straight-line length on the injection surface of the device that is in contact with a patient's skin during injection (parallel to the injection surface). The height is defined as the largest straight-line length of the device away from the skin during injection (perpendicular to the injection surface). See the ranges for the low and high aspect ratios in the parameter table shown in FIG. 133.

Embodiments of the case may include cases that can be rigid or flexible in nature. The casing material may be metal, thermoplastic (TP), thermoplastic elastomer (TPE), fiber reinforced composite, ceramic, or a combination of materials to provide physical and/or thermal protection for the device. In various embodiments, the case is substantially symmetrical about a horizontal plane and may be uniform about a central axis. The case may be configured in such a means that it is adaptable to everyday use items, and can be attached, whether molded or not, to different cases or objects to increase portability. In addition, certain embodiments may allow the user to carry a single device or multiple devices.

Certain rigid embodiments of the case may contain two vacuum sealed chambers forming an enclosure around the device, to provide thermal protection. The protective case may consist of upper and lower portions of equal or unequal proportions which when mated together form a sealed enclosure. The lower portion may include a double wall, forming a lower vacuum chamber in between, and a lower sidewall flange, where the lower vacuum chamber extends within at least a portion of the lower sidewall flange. The upper portion may include a double wall forming an upper vacuum chamber therebetween and an upper sidewall flange, where the upper vacuum chamber extends within at least a portion of the upper sidewall flange. When the lower portion and the upper portion are mated, the lower and upper sidewall flanges overlap to form a substantially sealed thermally isolated interior cavity for receiving the auto-injector. The pressure in each of the vacuum chambers may be set to reduce the rate of heat transfer and outlined in the parameter table shown in FIG. 133.

In one aspect, an embodiment of the protective case may provide a lower rate of heat transfer between the internal chamber and the external environment or vice versa. In addition to the sealed vacuum chamber, an embodiment may contain an additional passive means of reducing the rate of heat transferred to or from the device. The internal sealed chamber may contain an additional thermal barrier to improve the insulating properties. The additional thermal barrier may consist of a TP, thermoplastic elastomer (TPE), open or closed cell foam layer or combinations of such, which may or may not be one complete piece but consists of multiple pieces that may interlock when the two halves of the case are mated together forming a substantially sealed barrier. The additional thermal barrier may prevent direct contact with the disposed device and the internal cavity wall further limiting the rate of heat transfer. The TP, TPE, or open or closed cell foam pieces may be affixed to the housing through various means including adhesive, mechanical means, or form molded to the housing. The additional insulating barrier may further consist of at least one of a lower insulating barrier disposed about an interior perimeter of the lower sidewall flange and an upper insulating barrier disposed about an interior perimeter of the upper sidewall flange. In addition to the insulating barrier applied to the internal cavity of the case, the internal surfaces of the vacuum chamber may be polished or coated with a reflective layer to reduce the heat transfer through radiation. The coating applied to both surfaces, or at minimum one surface, of the sealed vacuum chamber may act as a reinforcement or aid in the structural integrity of the rigid case in addition to providing a reflective barrier. Furthermore, the case may have an exterior layer or coating consisting of a metal, TP, TPE, fiber reinforced composite, ceramic, or open or closed cell foam or a combination of such materials to aid in thermally insulating the case and disposed device.

The proposed embodiments of the rigid and elastic cases may provide a means of securing the device in a stable manner to eliminate or reduce any motion of the device relative to the case due to external loading or vibration. The method of which the case may secure the device can provide a means to aid in the placement of the device for orientation as well as aid in the removal of the device. The method of which the barrier on the internal chamber of the case may provide an insulating means, it may further assist in securing and stabilizing the device. The insulation barrier may form a cavity that releasably receives portion of the device and can provide the user with accessibility to remove the device from the case. The case may include a lower stabilizing element disposed within the lower portion and/or an upper stabilizing element disposed within the upper portion to support the auto-injector disposed in the interior cavity. The stabilizing element can include a material including a closed cell polymer foam, an open cell polymer foam, rubber, TP, TPE, and/or combinations thereof. The barrier material may be chosen such that its properties aid in thermally isolating the device as well as aid in damping induced vibrations. Furthermore, embodiments may be configured to protect more than one device as well as hold dissimilar devices if deemed necessary. The configuration of holding multiple devices is not limited to a horizontal or vertical layout of stacking, but instead allows for the best optimized method of storing the devices while maintaining a relatively low-profile case.

The sidewall flanges of the upper and lower portions of the thermally protective case may overlap axially, radially, and/or circumferentially to provide an adequately sealed joint. The sealed enclosure may be formed by several different configurations of mates between the upper and lower portion, some of which may include a friction fit, a threaded connection, etc. Embodiments which contain a threaded connection to facilitate the joint between the two halves may provide threads on either corresponding half such that the threads are concealed when connected. In some embodiments the thermal barrier affixed to the inner housings may provide the bond between the two halves of the case. Additionally, when the lower portion and the upper portion are mated together, the interior of the enclosure may be thermally isolated as well as substantially watertight. Embodiments of the rigid case may provide a watertight/water-resistant seal to protect the device from exposure to water or other fluids. The watertight/water-resistant connection between the upper and lower halves of the sealed enclosure may be facilitated by means of a gasket of suitable material, or through the addition of a coating or separate material applied at the joint interface.

An embodiment of the auto-injector case may consist of an ergonomic shape such that it fits easily into an individual's hand and the contours of the case may provide adequate surface area for proper handling. Furthermore, the embodiment may contain an external coating or layering applied to the case. The exterior layer or coating may consist of a metal, TP, TPE, fiber reinforced composite, ceramic, or open or closed cell foam, or a combination of such materials. The external coating may provide the following functionalities; shock absorbing, textured to aid in handling or gripping of the case, contoured surface profiles to aid in handling or gripping, thermal insulation for the device, degradation protection from environmental effects, and structural support for the case integrity. The case can further include an external surface including an embossed surface, a ribbed surface, a grip, and/or combinations thereof. In certain embodiments the insulation barrier may protrude radially from the case to provide a user interface for device removal. Furthermore, the coating or layering may provide a means of applying a label to the external surface of the case.

Examples of the proposed case for an auto-injector include, but are not limited to, embodiments that may provide a means of attachment to everyday items such as keychains, lanyards, wrist straps, cell phones, bikes, etc. Additionally, certain embodiments may include the use of a combination of rigid and elastic cases to provide more accessibility or portability. The attachment mechanisms may include, but are not limited to; a strap, a clip, a pin, a clamp, a mount, a tab forming an eyelet, an adhesive layer, and/or combinations thereof. The method of which the embodiment may provide or allow for a means of attachment between the protective case with a user or object. In various embodiments the protective case forms a second cavity for receiving a second device (e.g., a cell phone and/or a second auto-injector device). In some instances, the second cavity circumscribes at least a portion of the device or auto-injector device.

In some embodiments the case may have an internal power source to allow certain functionalities of the case while storing the device. The case may provide audible instructions relating to the contained device for performing an injection or the stored condition of the device. Additionally, the case may provide connectivity to everyday smart devices for additional functionality. Certain embodiments may allow for the user to monitor the temperature, and location of the case. Additionally, the connected case may allow the user to see if other auto-injector devices are nearby. Additional embodiments may contact emergency responders or next of kin once the auto-injector device has been removed from the case. The case may also provide a display and/or interface for inspection of the case and internal conditions. The case may also provide a means of detecting excessive vibrations or impacts while storing the device. Furthermore, information about the case and contained auto-injector device may be monitored remotely by the manufacturer.

In general, embodiments of the invention are of a protective case for an auto-injector device, for which the case may be rigid, elastic or combination of the two. The method can include the following: (I) a protective case forming a cavity that releasably receives at least a portion of the auto-injector device; (II) the protective case which may contain a lower portion including a double wall forming a lower vacuum chamber therebetween and a lower sidewall flange, where the lower vacuum chamber extends within at least a portion of the lower sidewall flange; and a mating upper portion including a double wall forming an upper vacuum chamber therebetween and an upper sidewall flange, where the upper vacuum chamber extends within at least a portion of the upper sidewall flange; (III) mating the sidewall flanges on the lower and upper portions to form a substantially sealed thermally isolated and or watertight/water-resistant interior cavity for the auto-injector; (IV) and providing a means of attachment for the case to common everyday objects.

In general, in one aspect, embodiments of the invention feature a protective case for enclosing a compact auto-injector used for delivering a medicament dose. The protective case can include a lower portion including a double wall forming a lower vacuum chamber therebetween and a lower sidewall flange, where the lower vacuum chamber extends within at least a portion of the lower sidewall flange; and a mating upper portion including a double wall forming an upper vacuum chamber therebetween and an upper sidewall flange, where the upper vacuum chamber extends within at least a portion of the upper sidewall flange, such that when the lower portion and the upper portion are mated, the lower and upper sidewall flanges overlap to form a substantially sealed thermally isolated interior cavity for receiving the auto-injector.

In various embodiments, the case is substantially symmetrical about a horizontal plane. The case can also be substantially uniform about a central vertical axis. In some instances, the pressure in each of the lower vacuum chamber and the upper vacuum chamber is less than about 0.1 torr. The lower portion and the upper portion can be disk shaped. In various configurations, the lower sidewall flange and the upper sidewall flange overlap axially, radially, and/or circumferentially.

In various embodiments, mating surfaces of the lower sidewall flange and the upper sidewall flange form a threaded interface and/or are sized to maintain a sliding interference fit. In some instances, the protective case also includes a lower insulating ring disposed about an interior perimeter of the lower sidewall flange and/or an upper insulating ring disposed about an interior perimeter of the upper sidewall flange. The insulating ring can include various materials including, for example, a closed cell polymer foam, an open cell polymer foam, rubber, TP, TPE, and/or combinations thereof. In some instances, the protective case also includes a lower stabilizing element disposed within the lower portion and/or an upper stabilizing element disposed within the upper portion to support the auto-injector when disposed in the interior cavity. The stabilizing element can include various materials including, for example, a closed cell polymer foam, an open cell polymer foam, rubber, TP, TPE, and/or combinations thereof. The protective case itself can include various materials including, for example a metal, a polymer, a composite material, a ceramic, and/or combinations thereof.

In various embodiments, the protective case also includes an attachment device to facilitate a user carrying the case. The attachment device can include an adjustable elastic strap, a non-elastic strap, a wrist strap, a wrist band, a clip, a tether, a necklace, a pin, a clamp, a mount, a tab forming an eyelet, an adhesive layer, a hand grip surface, and/or combinations thereof. In some instances, the protective case is further characterized by an absence of active thermal control of the interior cavity. In some configurations, when the lower portion and the upper portion are mated, the substantially sealed thermally isolated interior cavity is at least one of substantially watertight and substantially water resistant. The protective case can also include an external surface that includes a coating, an embossed surface, a ribbed surface, a grip, and/or combinations thereof. In some embodiments, the protective case includes a reflective coating disposed on an interior surface of the lower vacuum chamber and the upper vacuum chamber. The interior cavity may be adapted to receive multiple auto-injectors.

In general, in another aspect, embodiments of the invention feature a method of thermally isolating a compact auto-injector containing a medicament dose from ambient environmental temperatures. The method can include the steps of providing a protective case that includes (i) a lower portion including a double wall forming a lower vacuum chamber therebetween and a lower sidewall flange, where the lower vacuum chamber extends within at least a portion of the lower sidewall flange, and (ii) a mating upper portion including a double wall forming an upper vacuum chamber therebetween and an upper sidewall flange, where the upper vacuum chamber extends within at least a portion of the upper sidewall flange; placing the auto-injector into an interior cavity portion formed by at least one of the lower portion and the upper portion; and mating the lower and upper sidewall flanges in overlapping relation to form a substantially sealed thermally isolated interior cavity for the auto-injector.

In various embodiments, the method can also include providing an attachment device to associate the protective case with a user. The attachment device can include an adjustable elastic strap, a non-elastic strap, a wrist strap, a wrist band, a clip, a tether, a necklace, a pin, a clamp, a mount, a tab forming an eyelet, an adhesive layer, a hand grip surface, and/or combinations thereof. In some cases, the method is further characterized by an absence of actively thermally controlling the interior cavity.

In general, in another aspect, embodiments of the invention feature an apparatus for associating an auto-injector device with a user. The apparatus can include a protective case forming a cavity for releasably receiving at least a portion of the auto-injector device, and an attachment device coupled to the protective case.

In various embodiments, the protective case forms a second cavity for receiving a second device. The second device can include a cell phone and/or a second auto-injector device. In some instances, the cavity circumscribes at least a portion of the auto-injector device. The attachment device can include an adjustable elastic strap, a non-elastic strap, a wrist strap, a wrist band, a clip, a tether, a necklace, a pin, a clamp, a mount, a tab forming an eyelet, an adhesive layer, a hand grip surface, and/or combinations thereof.

In general, in another aspect, embodiments of the invention feature a method for associating an auto-injector device with a user. The method can include the steps of providing a protective case forming a cavity for releasably receiving at least a portion of the auto-injector device, and providing an attachment device adapted to be coupled to the protective case.

In various embodiments, the protective case forms a second cavity for receiving a second device. The second device can include a cell phone and/or a second auto-injector device. In some instances, the cavity circumscribes at least a portion of the auto-injector device. The attachment device can include an adjustable elastic strap, a non-elastic strap, a wrist strap, a wrist band, a clip, a tether, a necklace, a pin, a clamp, a mount, a tab forming an eyelet, an adhesive layer, a hand grip surface, and/or combinations thereof.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention. In the following description, various embodiments of the present invention are described with reference to the following drawings, in which:

FIG. 133 is a table showing exemplary properties for protective cases.

DETAILED DESCRIPTION

Figure 1:
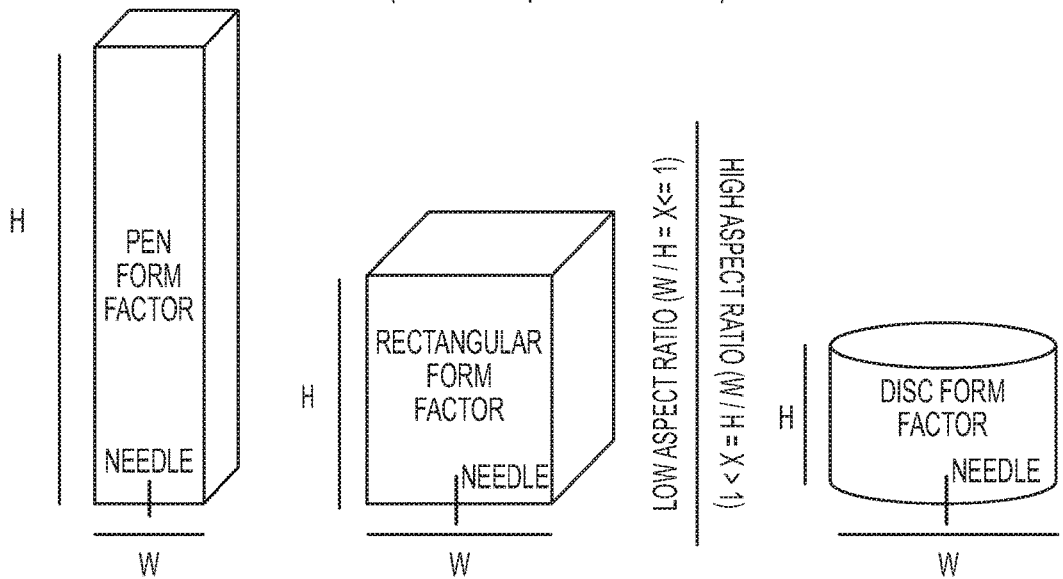
FIG. 1 is a depiction of existing low aspect ratio auto-injectors, as well as an example high aspect ratio auto-injector, according to one embodiment.
Figure 2:
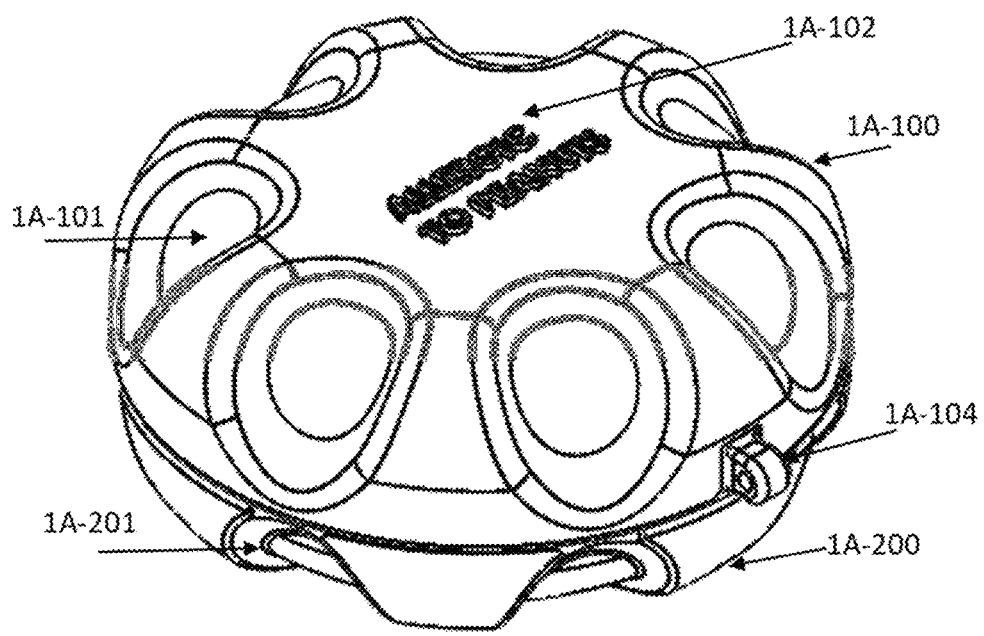
FIGS. 2-15 are schematic views of a vacuum sealed protective case with IoT (internet of things) functionality for a high aspect ratio auto-injector, according to example embodiments.
Figure 3:
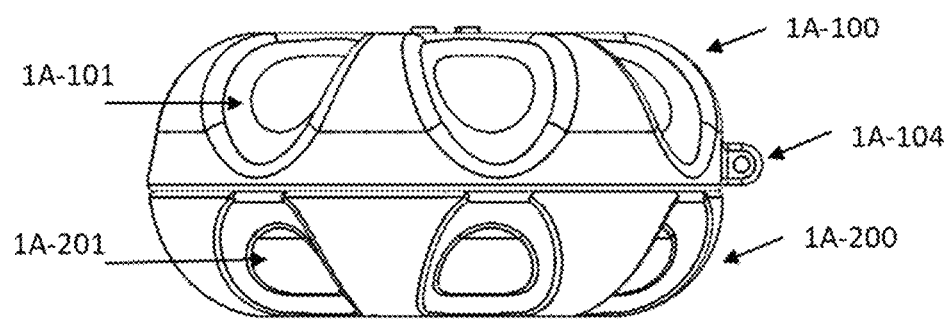
Figure 4:
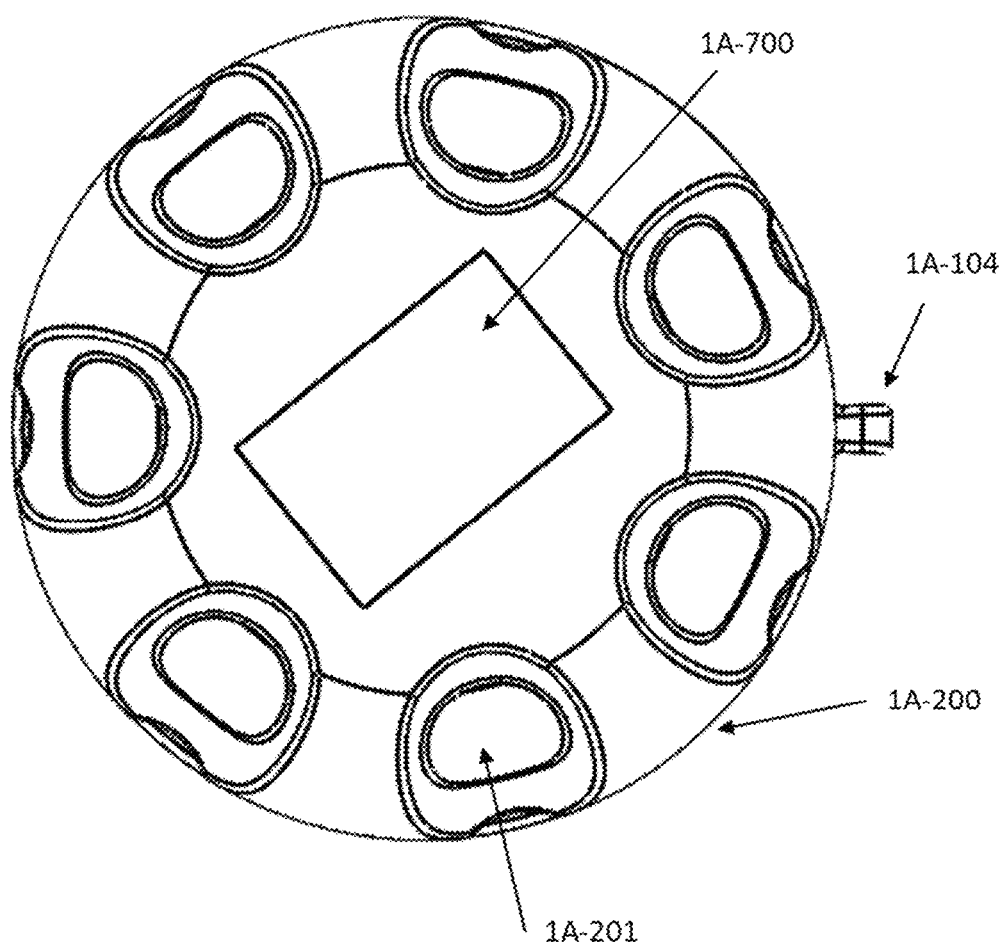
Figure 5:
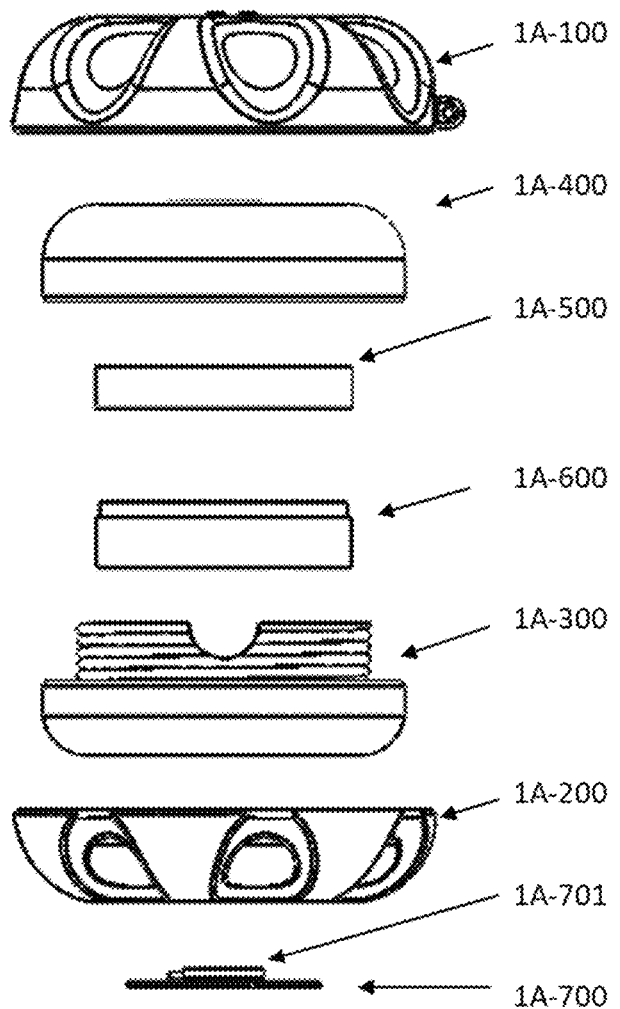
Figure 6:
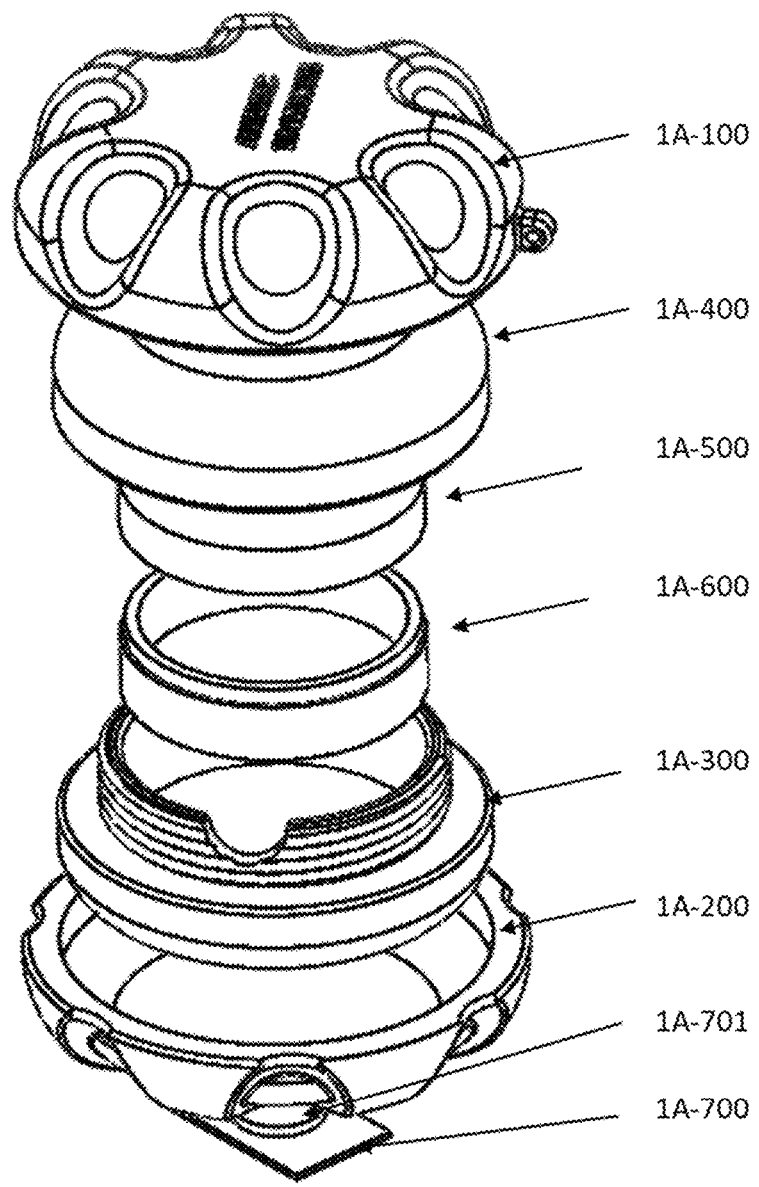
Figure 7:
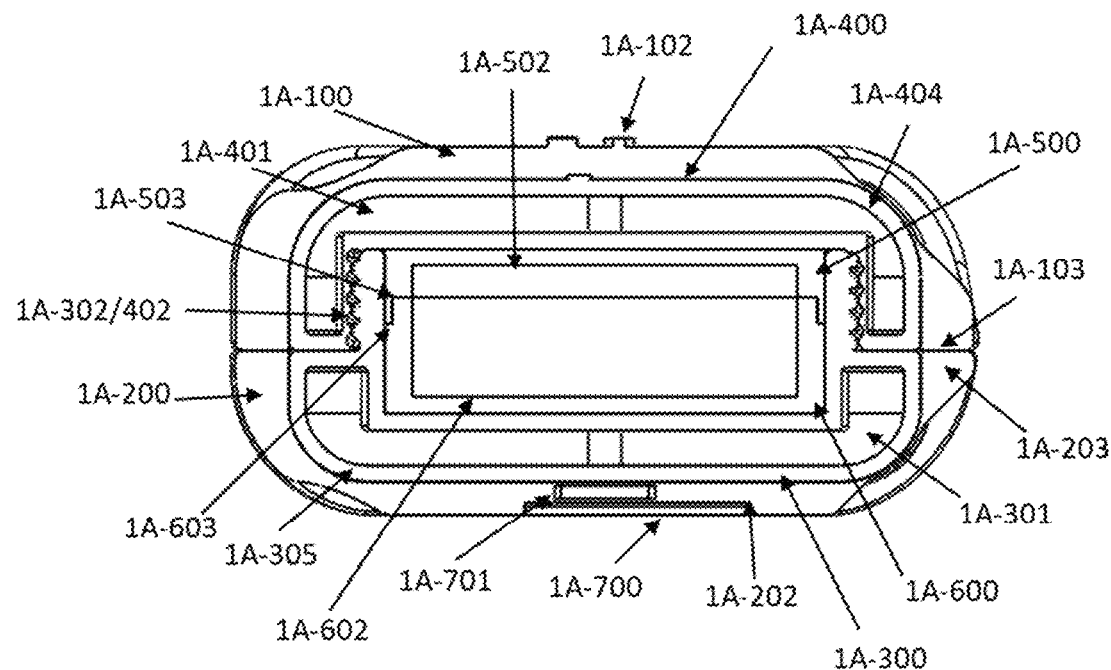
Figure 8:
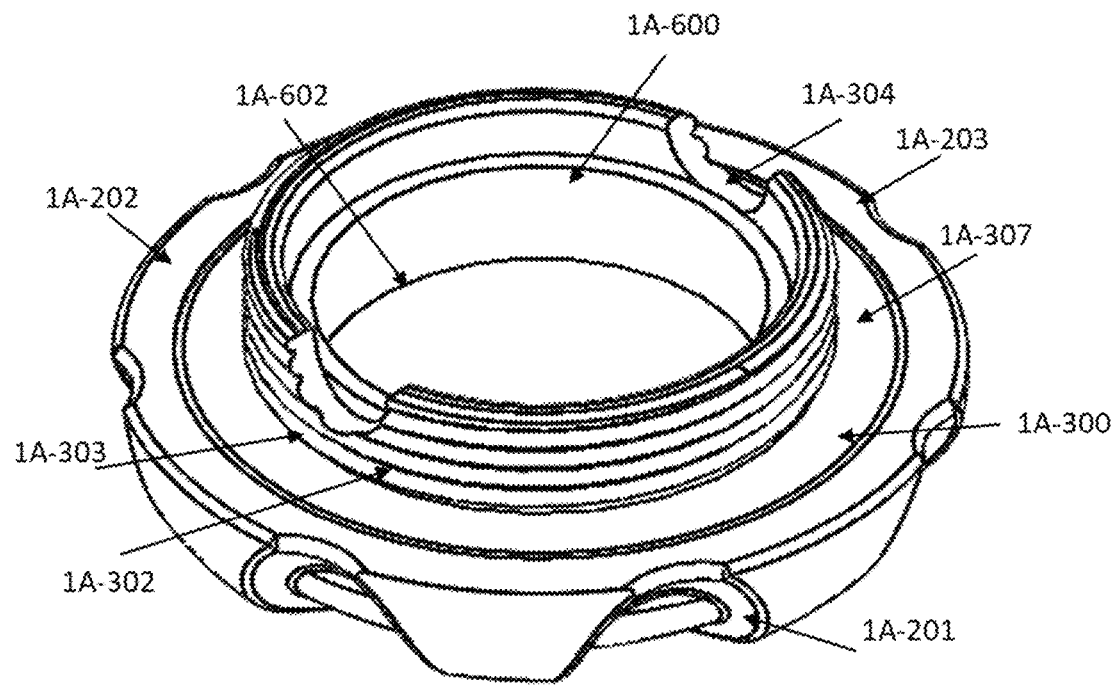
Figure 9:
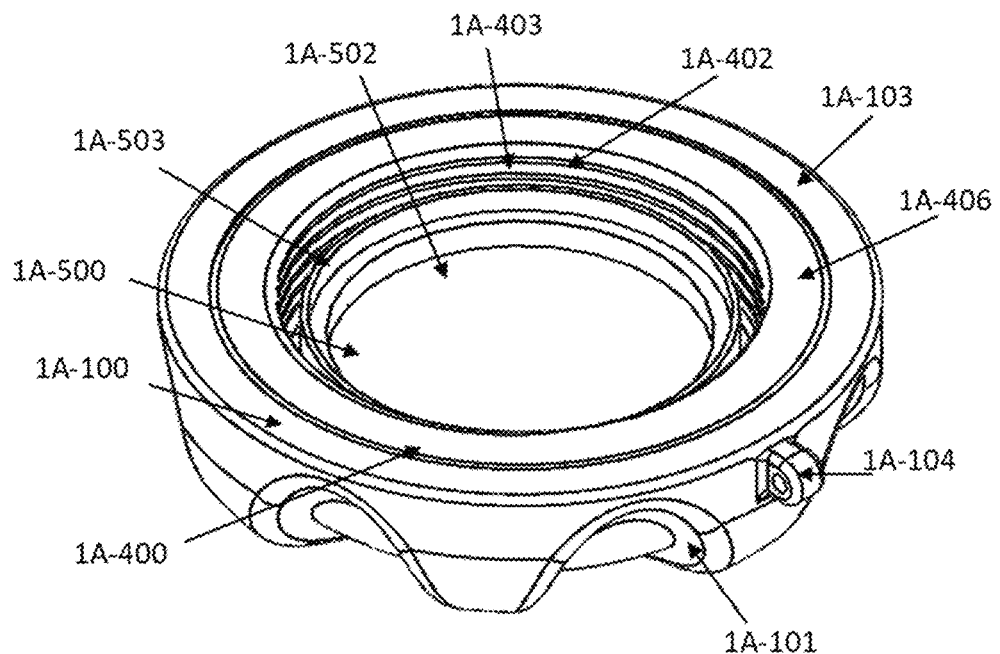
Figure 10:
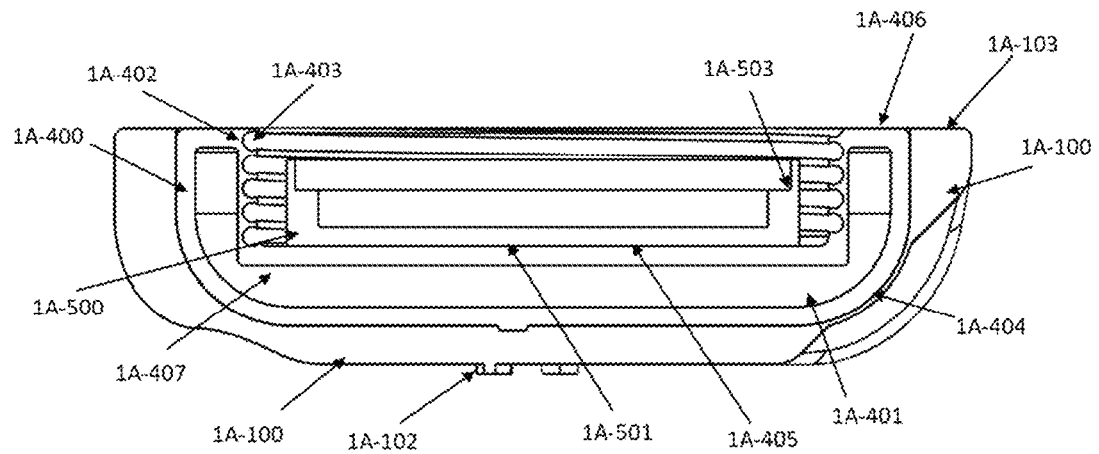
Figure 11:
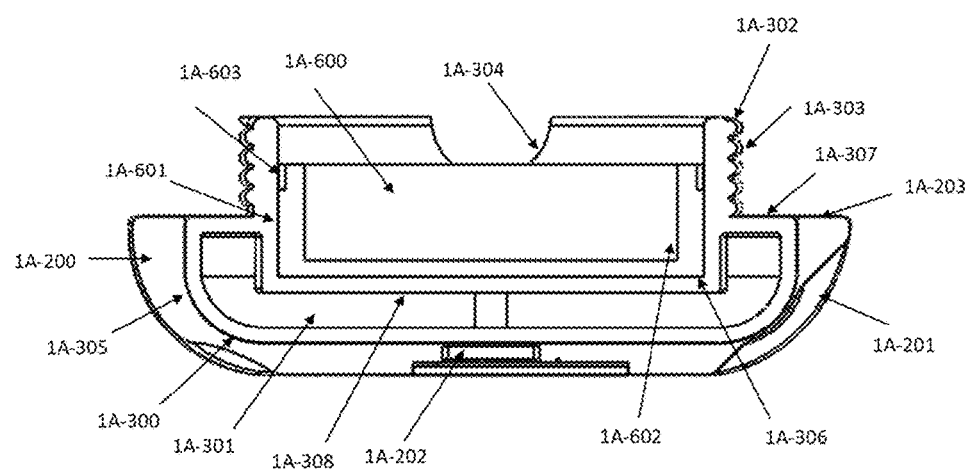
Figure 12:
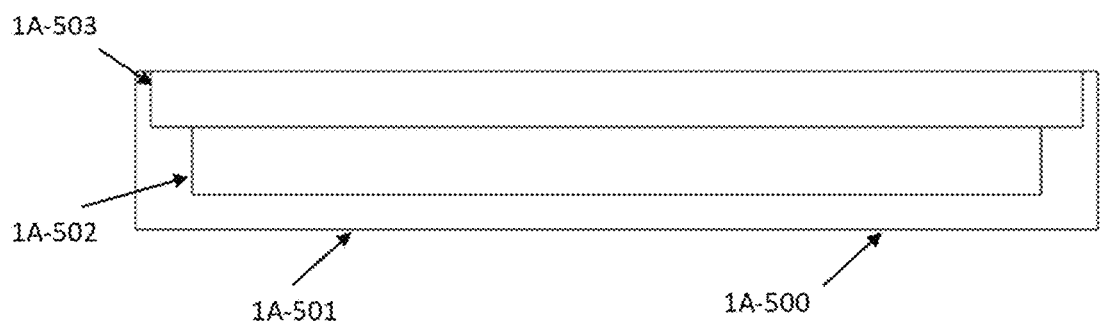
Figure 13:
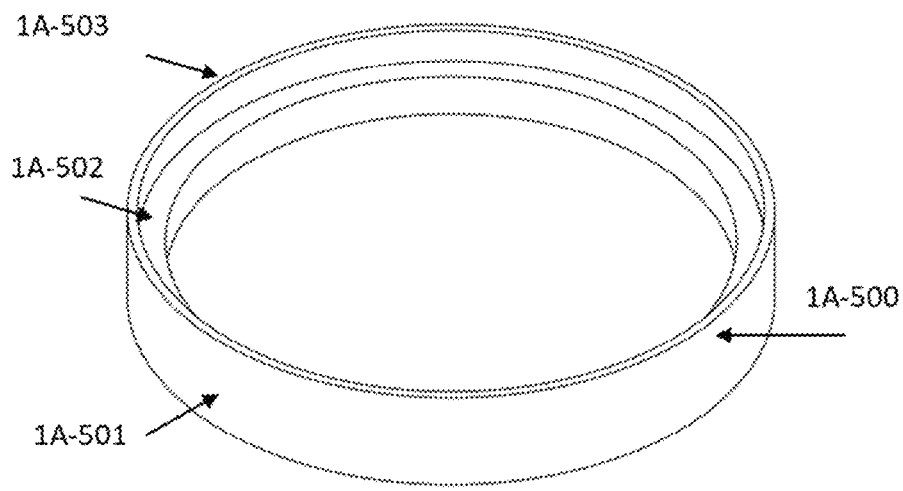
Figure 14:
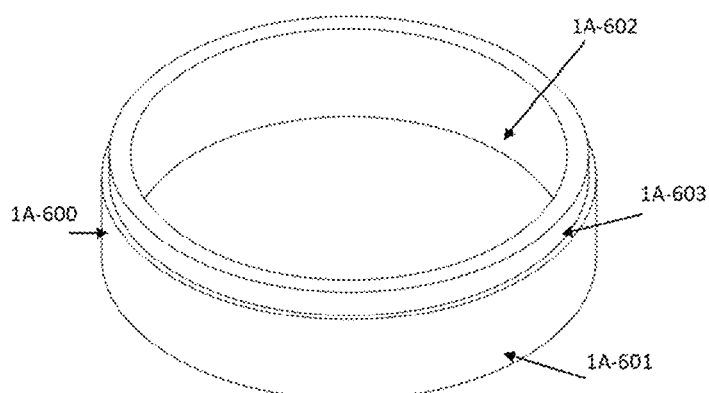
Figure 15:
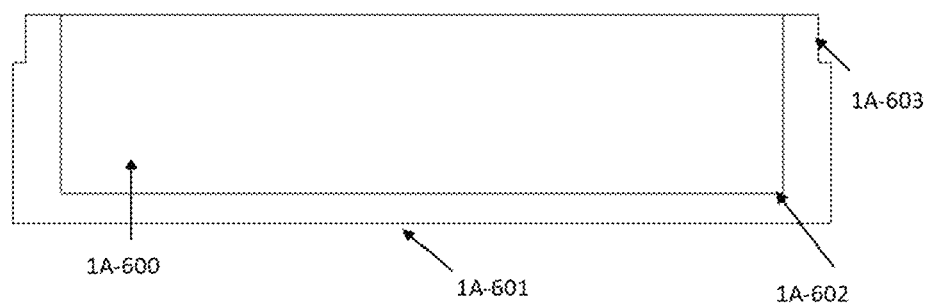
Figure 16:
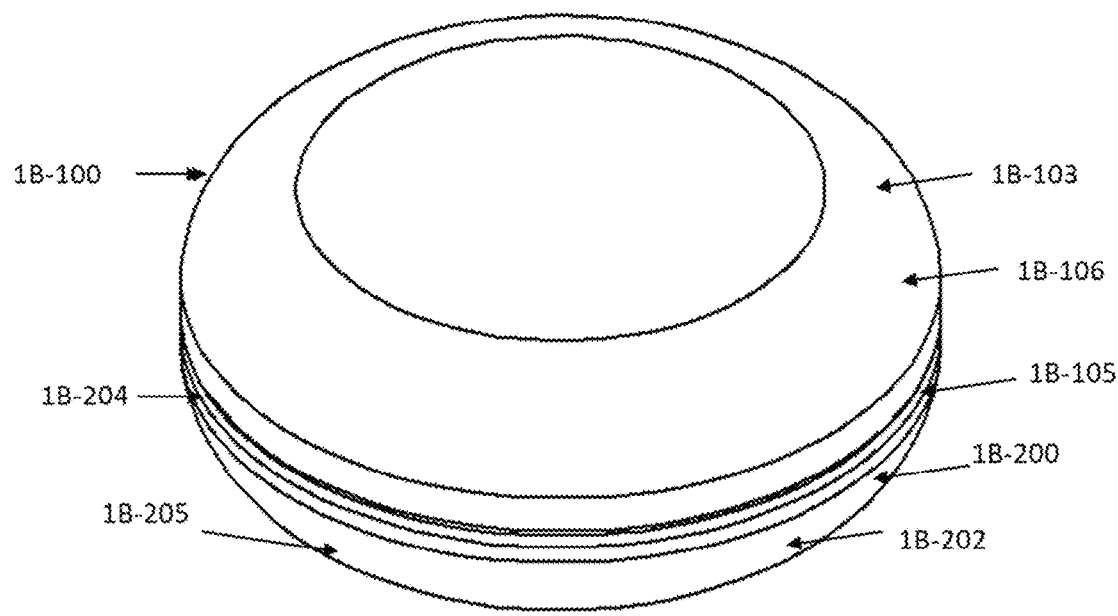
FIGS. 16-58 are schematic views of a vacuum sealed protective case for carrying a single high aspect ratio auto-injector, according to example embodiments.
Figure 17:
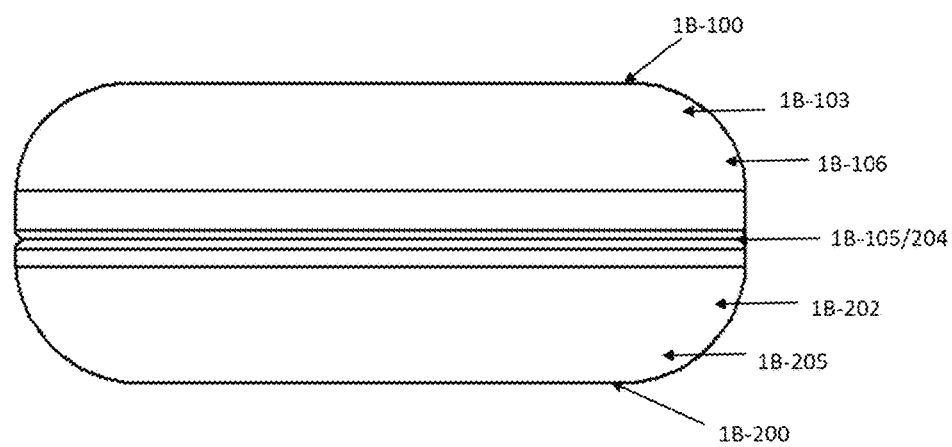
Figure 18:
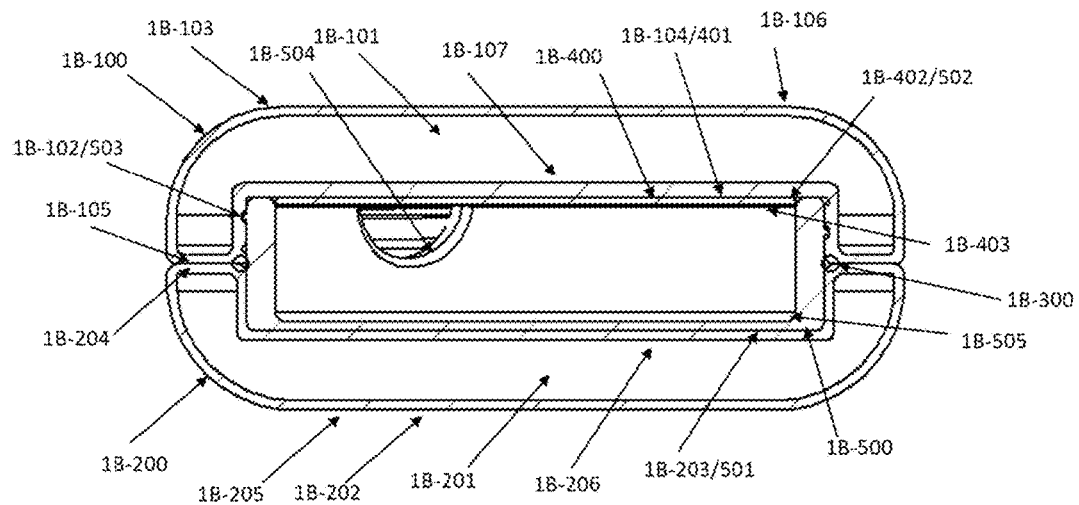
Figure 19:
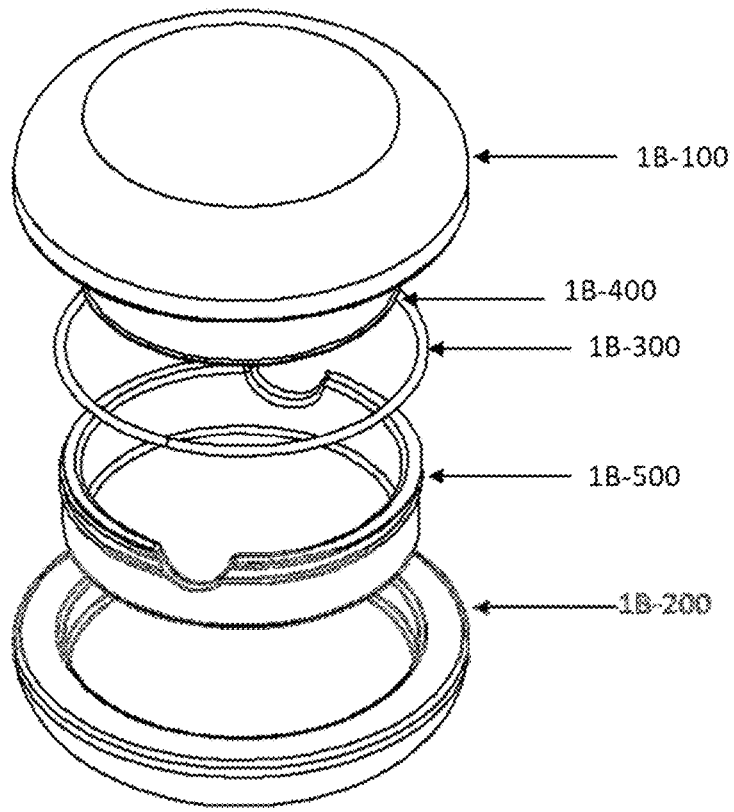
Figure 20:
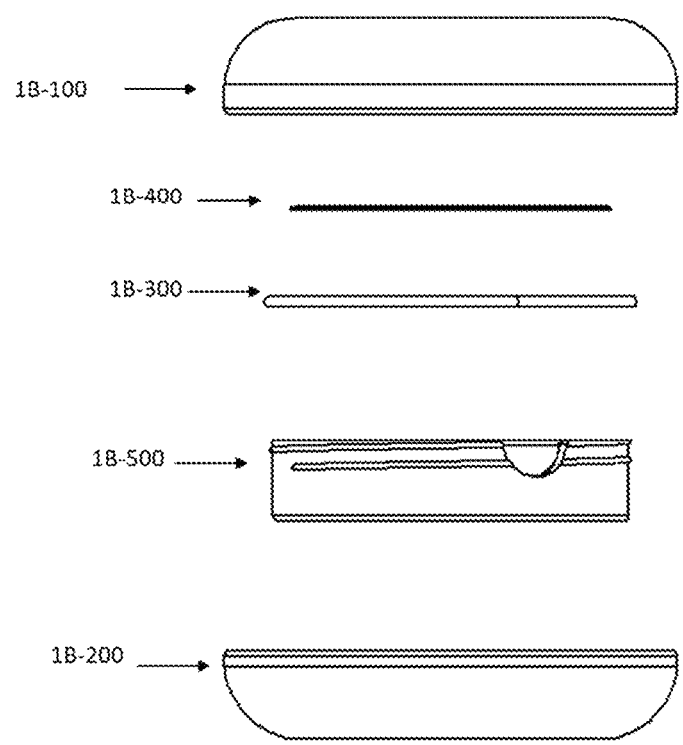
Figure 21:
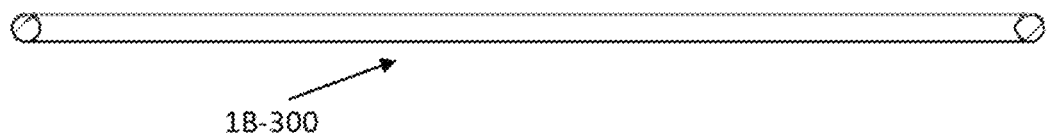
Figure 22:
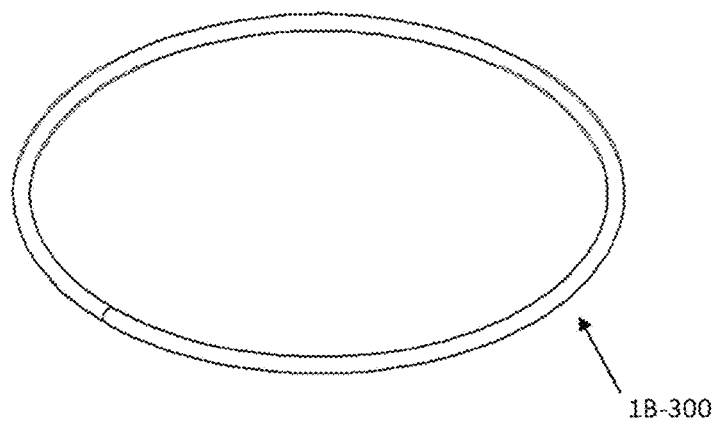
Figure 23:
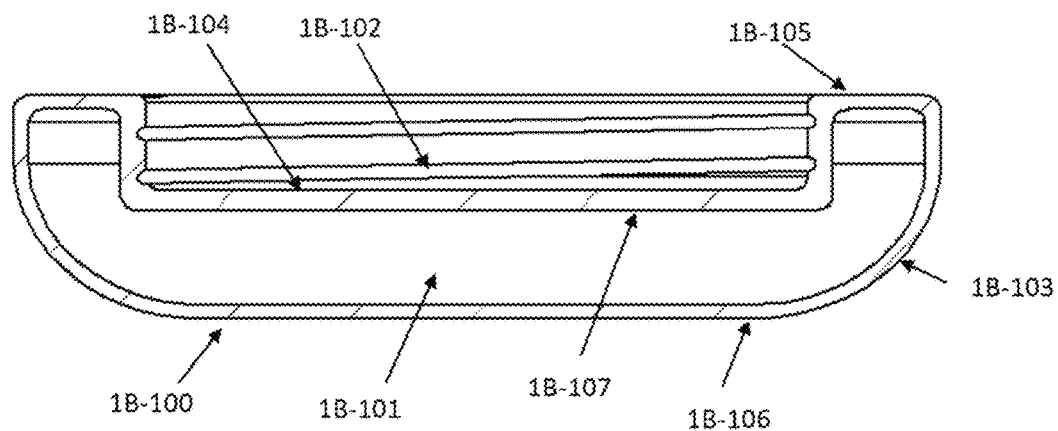
Figure 24:
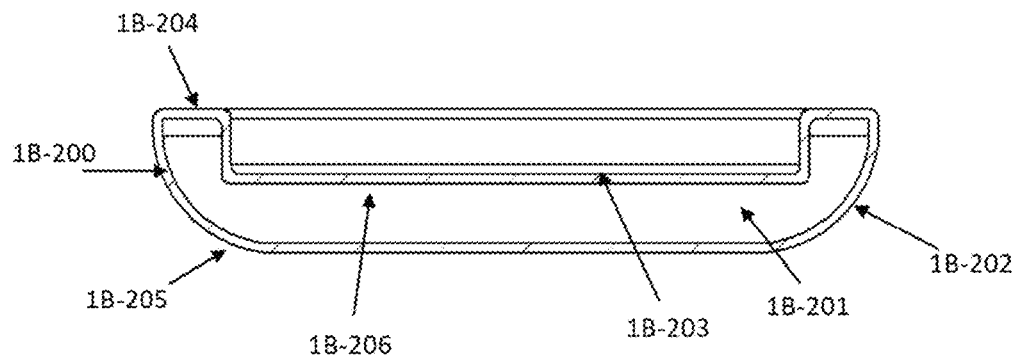
Figure 25:
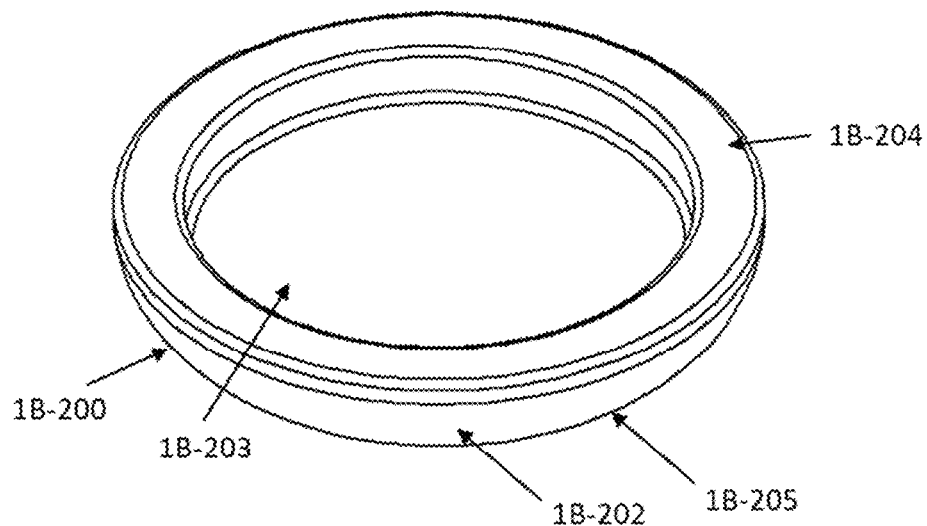
Figure 26:
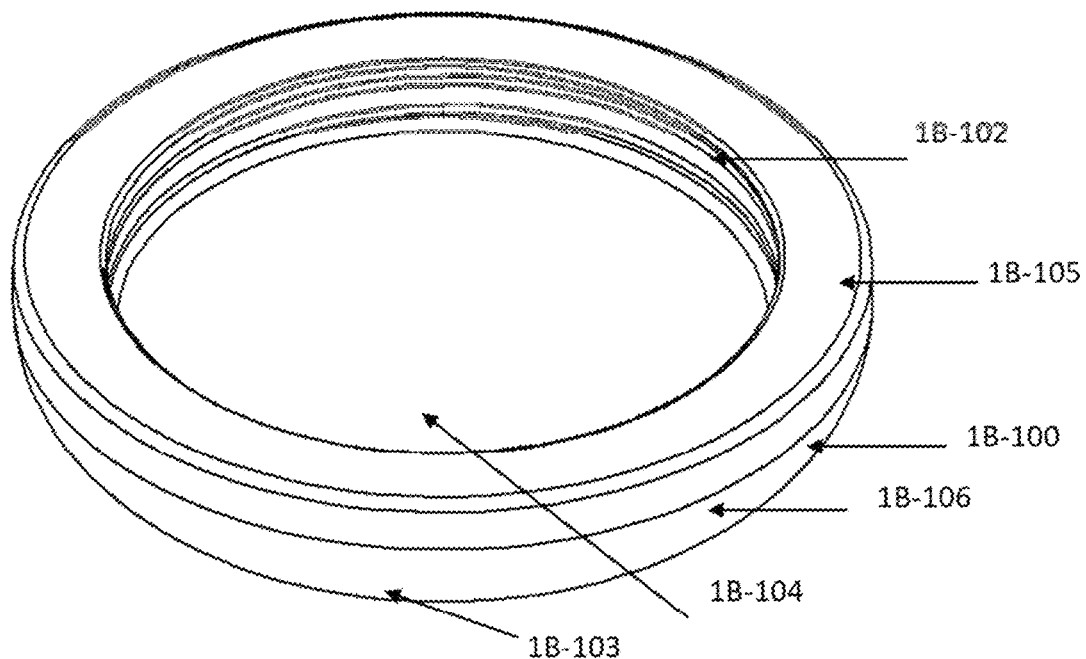
Figure 27:
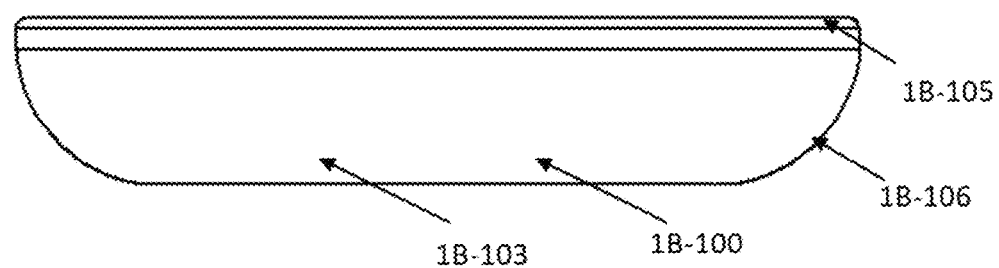
Figure 28:
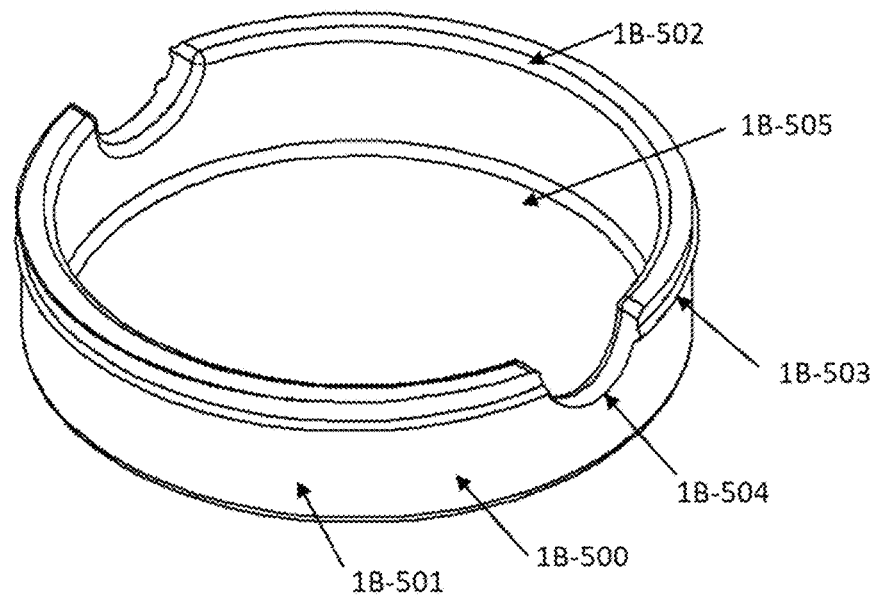
Figure 29:
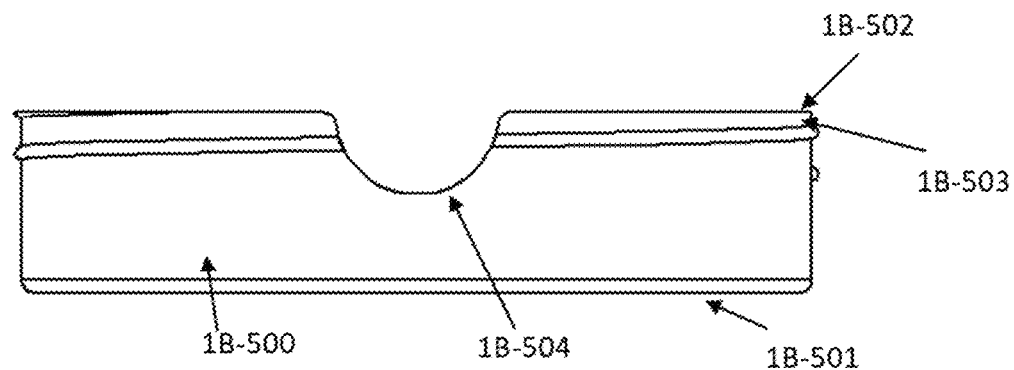
Figure 30:
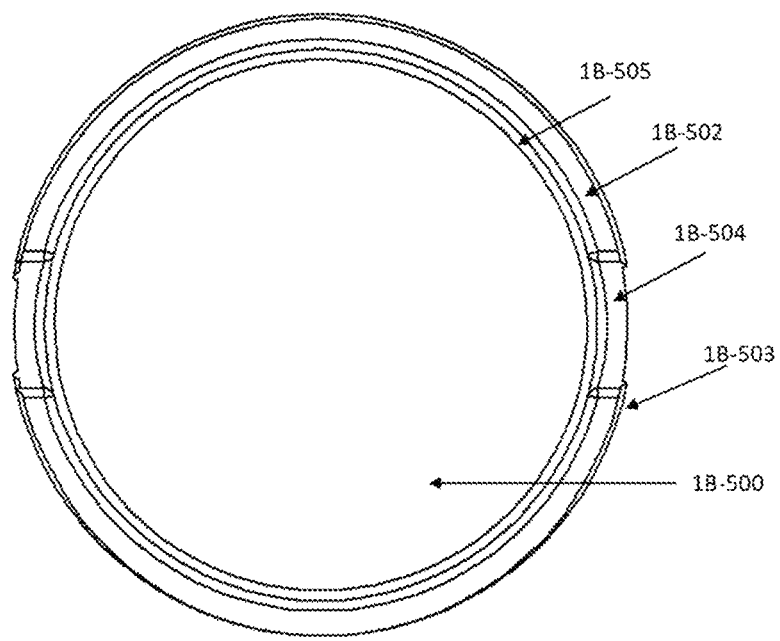
Figure 31:
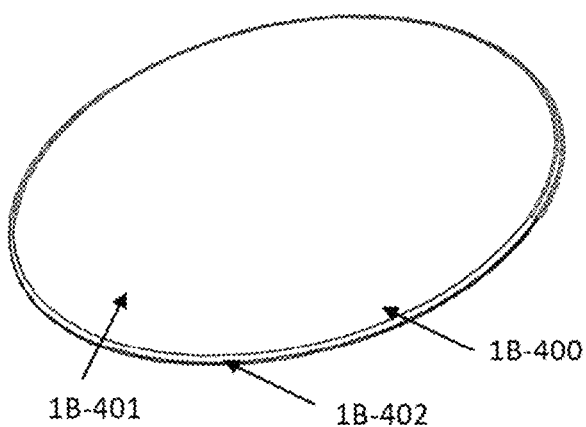
Figure 32:
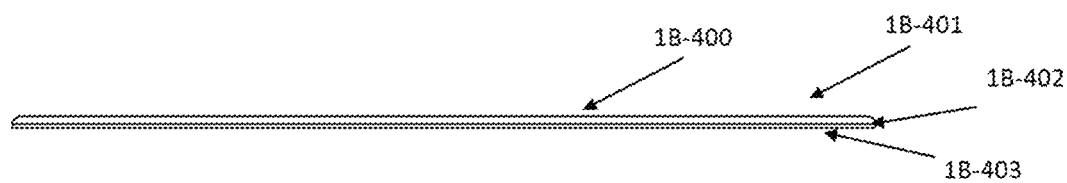
Figure 33:
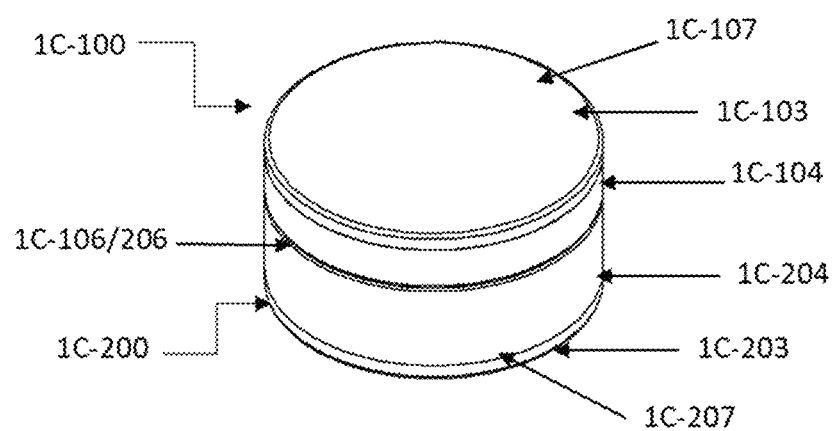
Figure 34:
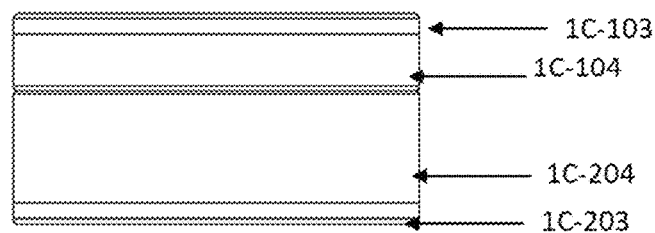
Figure 35:
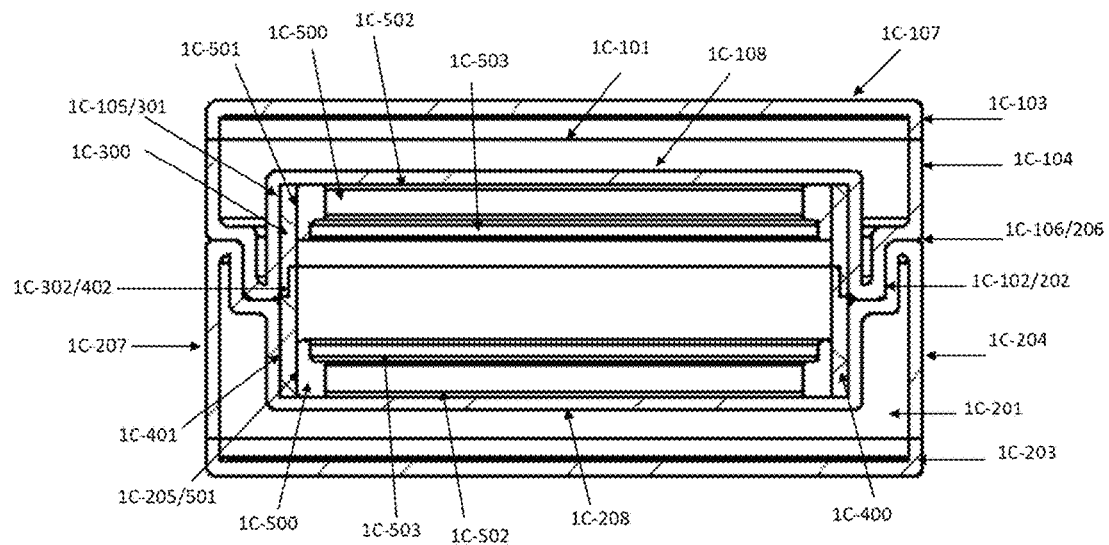
Figure 36:
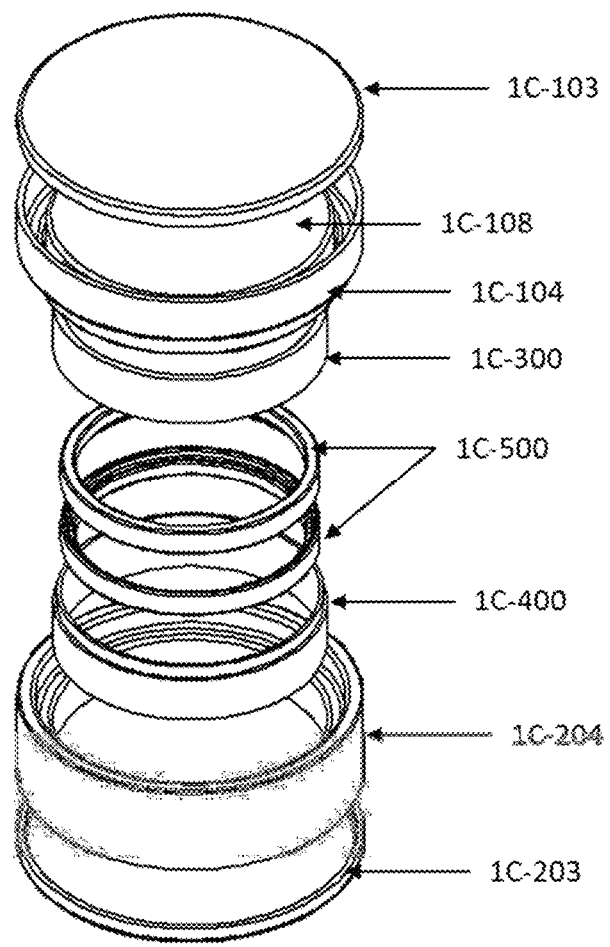
Figure 37:
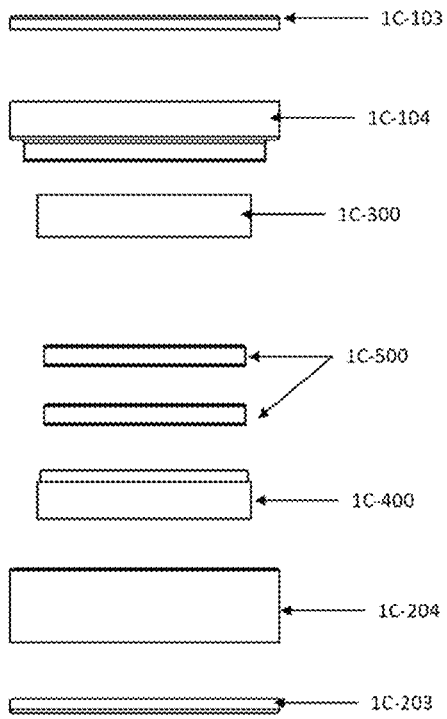
Figure 38:
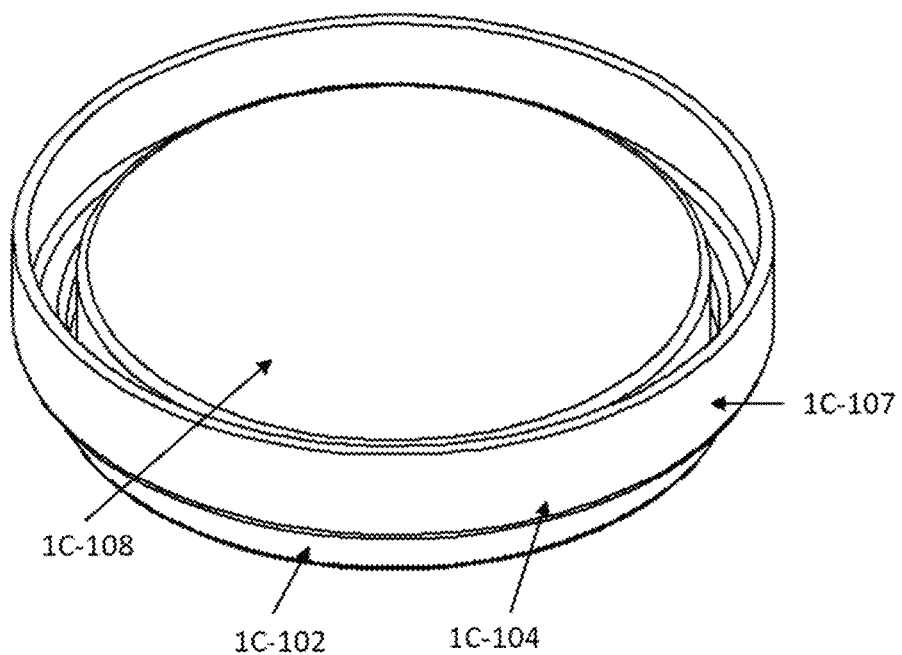
Figure 39:
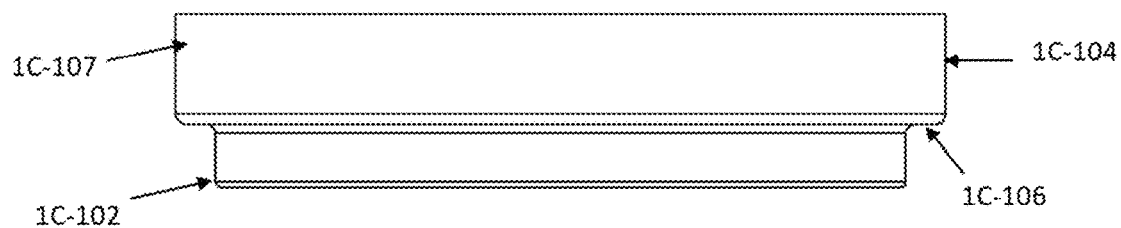
Figure 40:
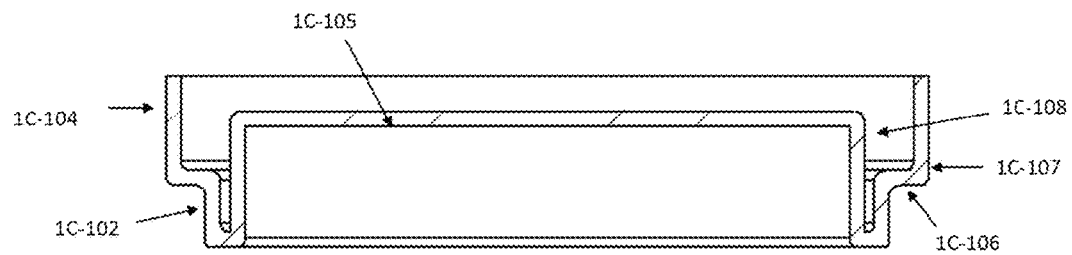
Figure 41:
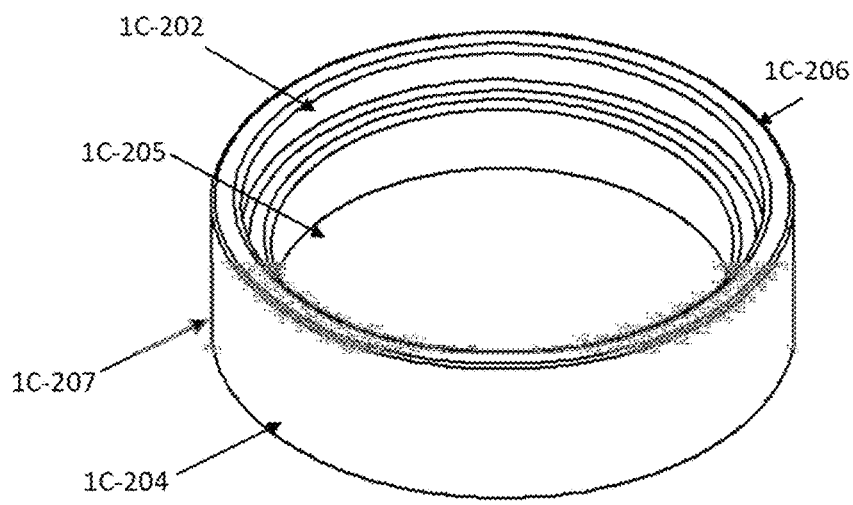
Figure 42:
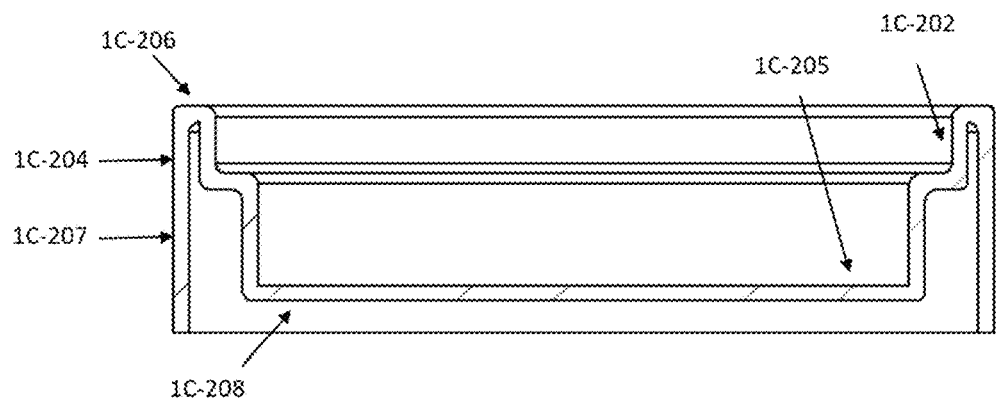
Figure 43:
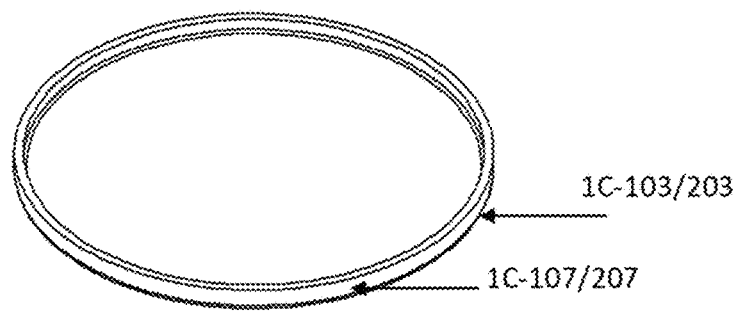
Figure 44:
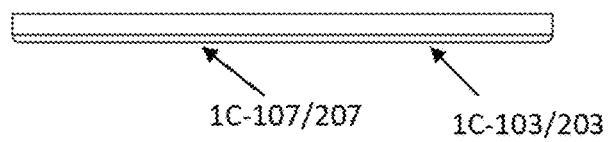
Figure 45:
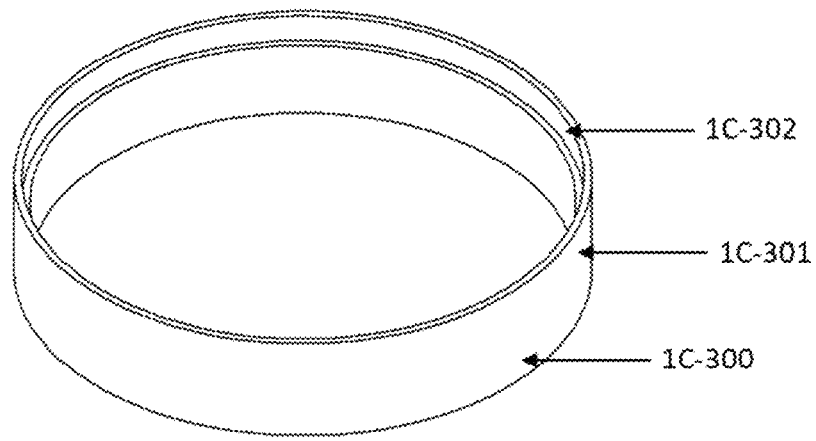
Figure 46:
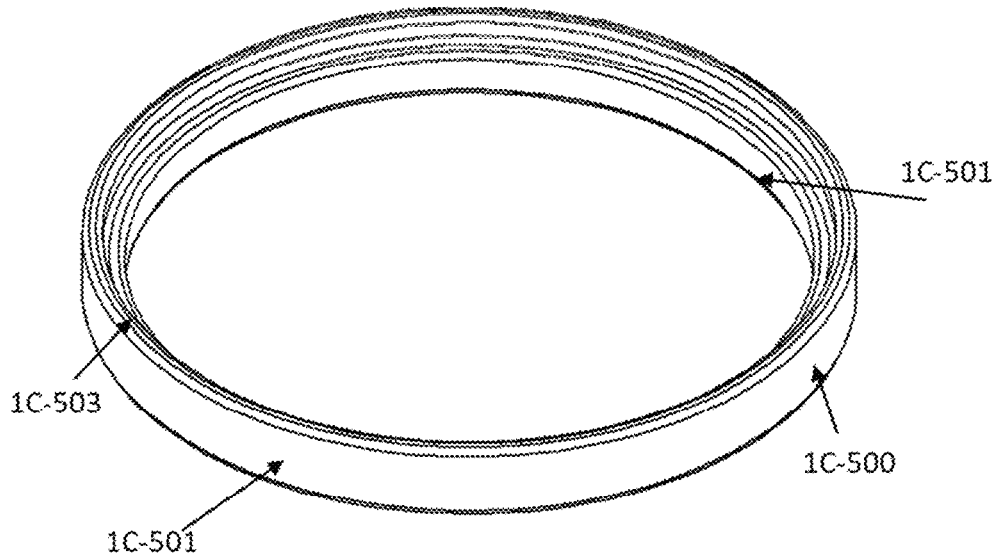
Figure 47:
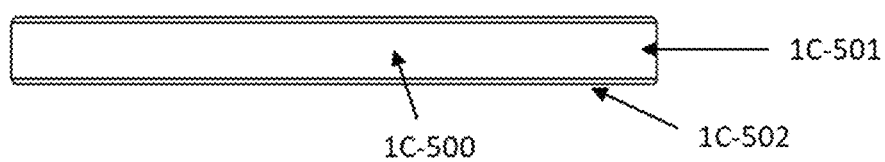
Figure 48:
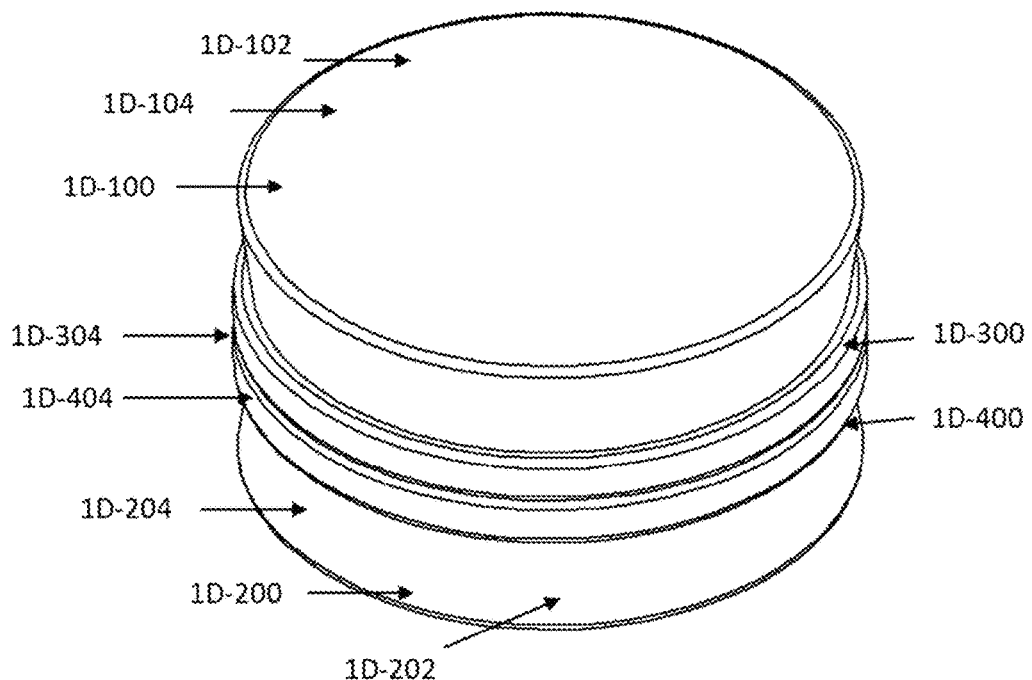
Figure 49:
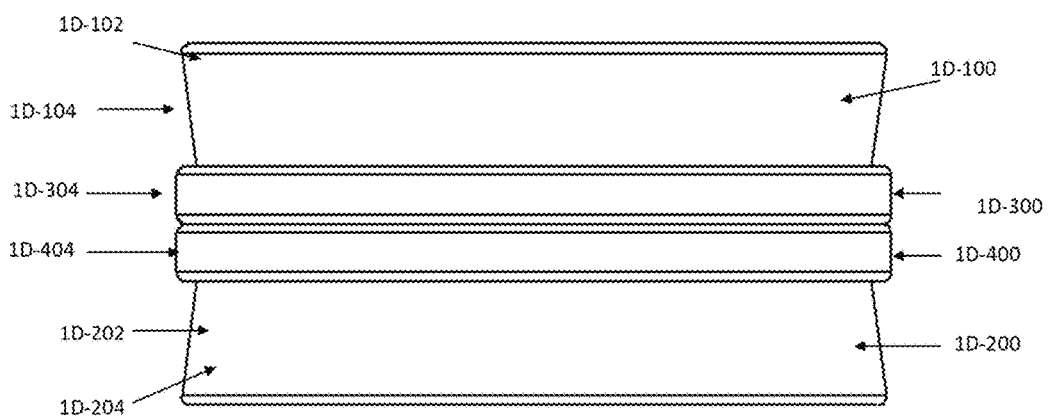
Figure 50:
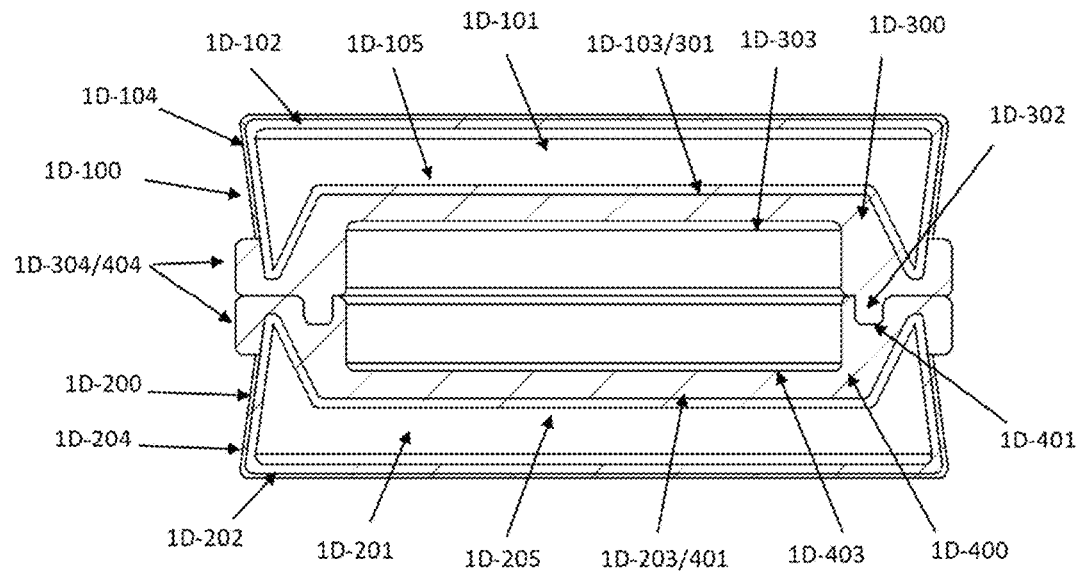
Figure 51:
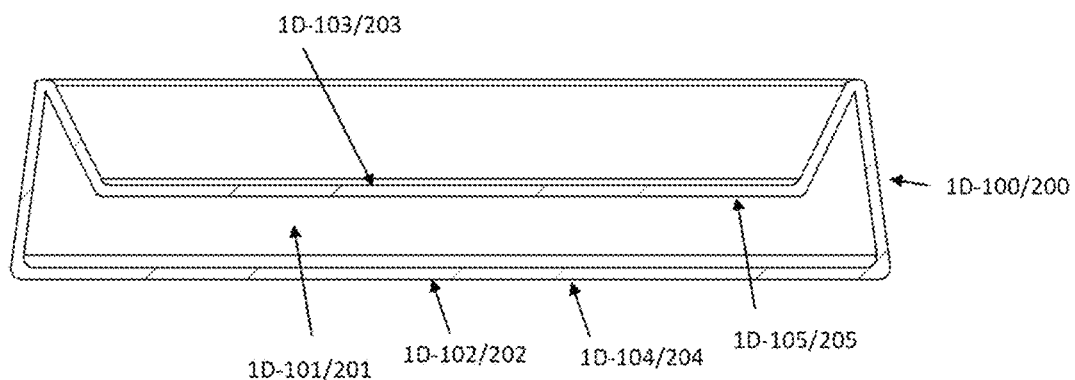
Figure 52:
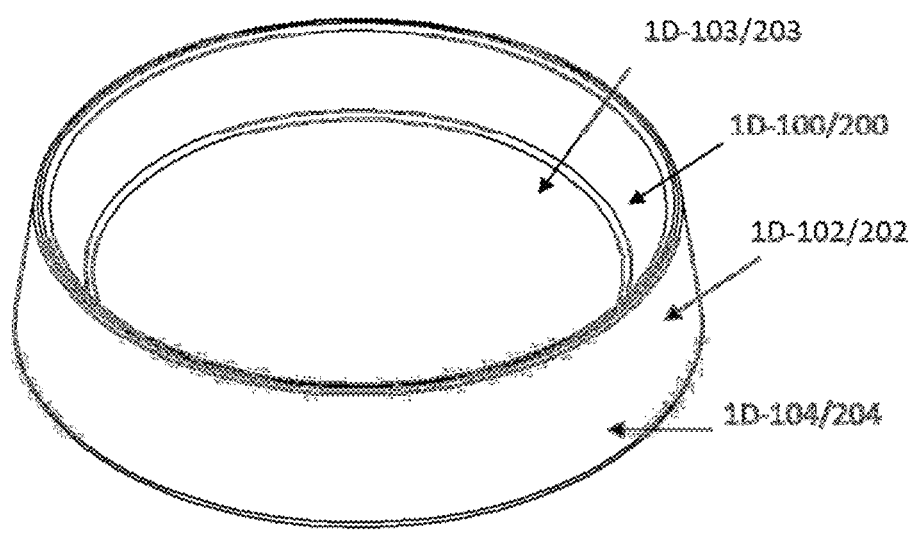
Figure 53:
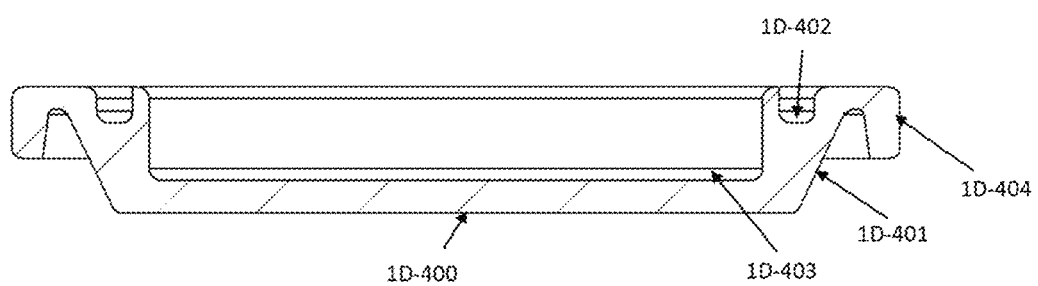
Figure 54:
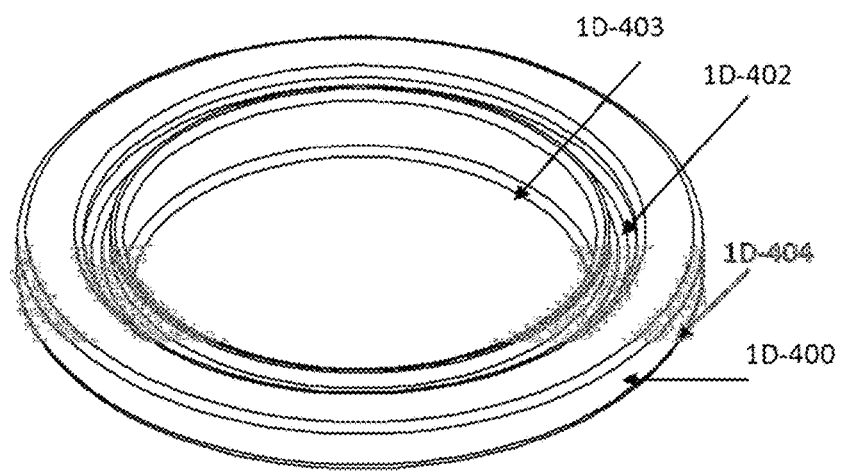
Figure 55:
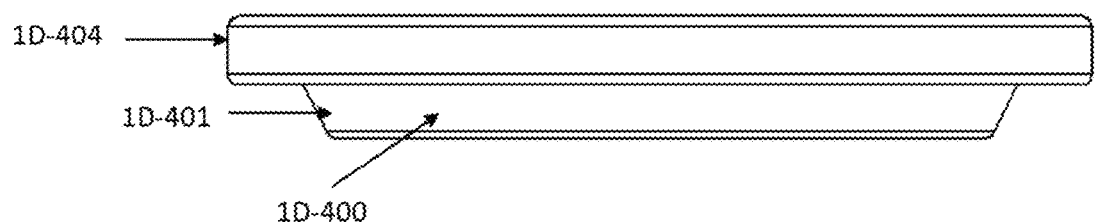
Figure 56:
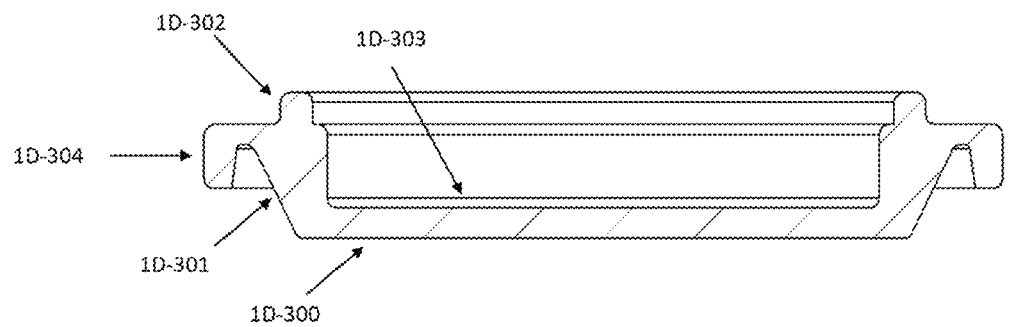
Figure 57:
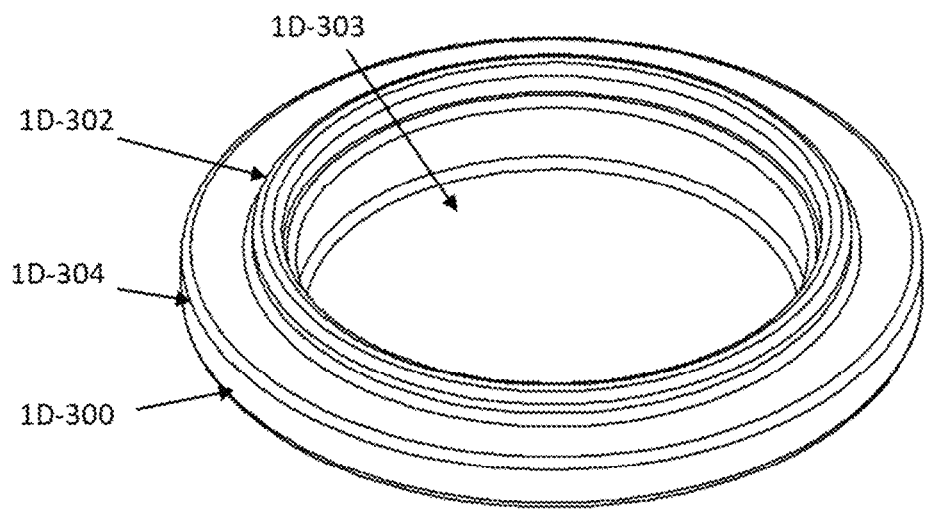
Figure 58:
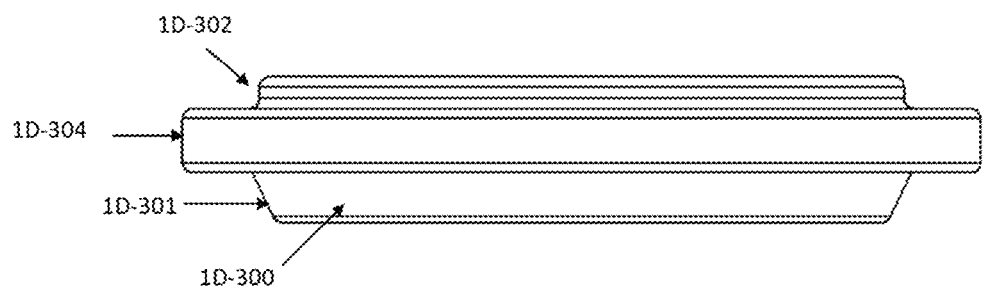
Figure 59:
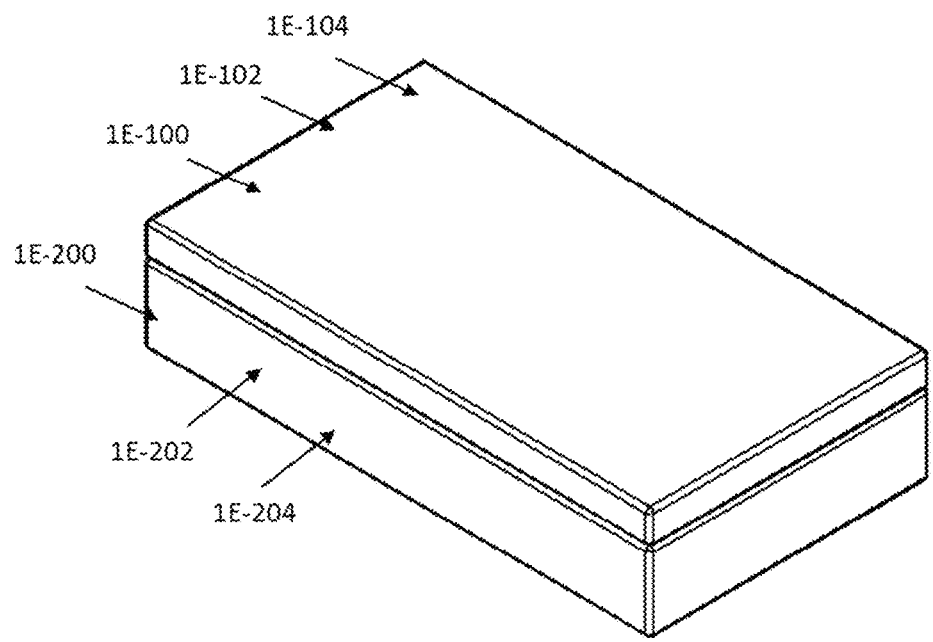
FIGS. 59-69 are schematic views of a vacuum sealed protective case for carrying multiple high aspect ratio auto-injectors, according to example embodiments.
Figure 60:
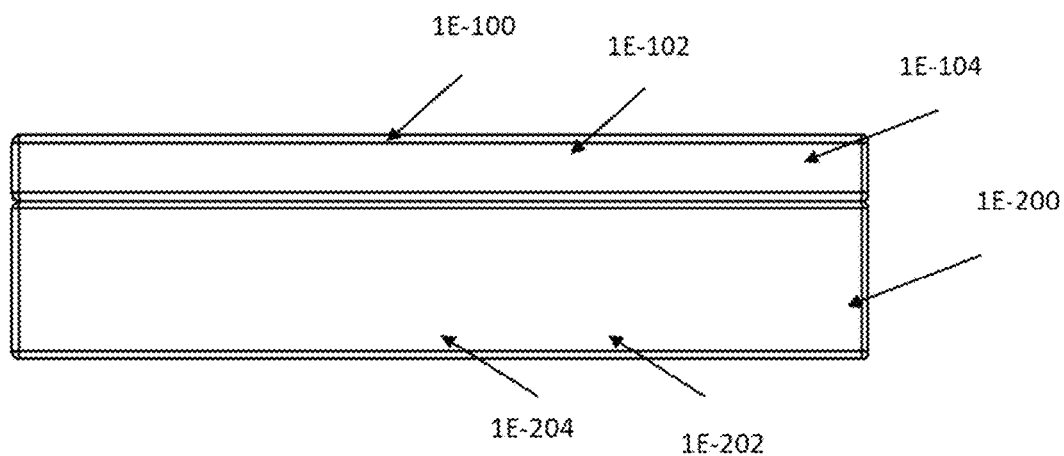
Figure 61:
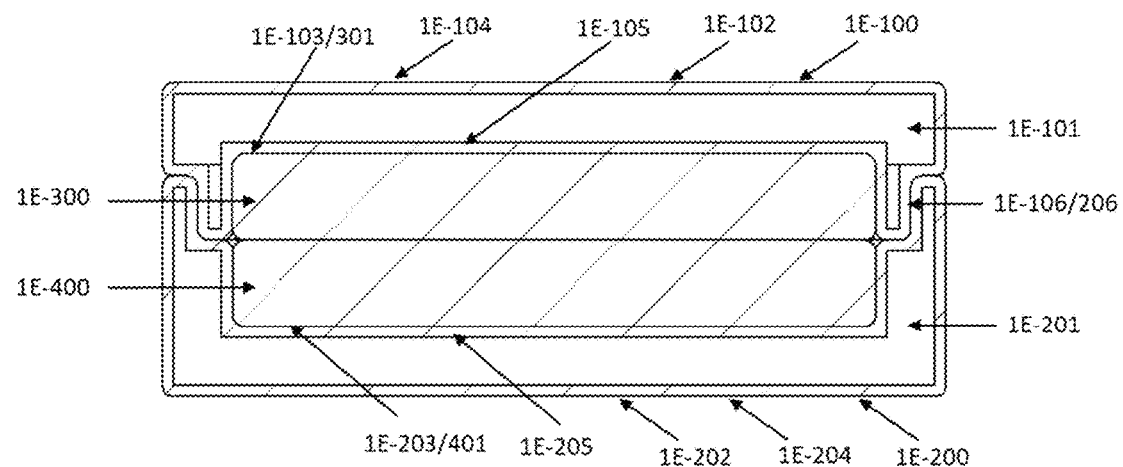
Figure 62:
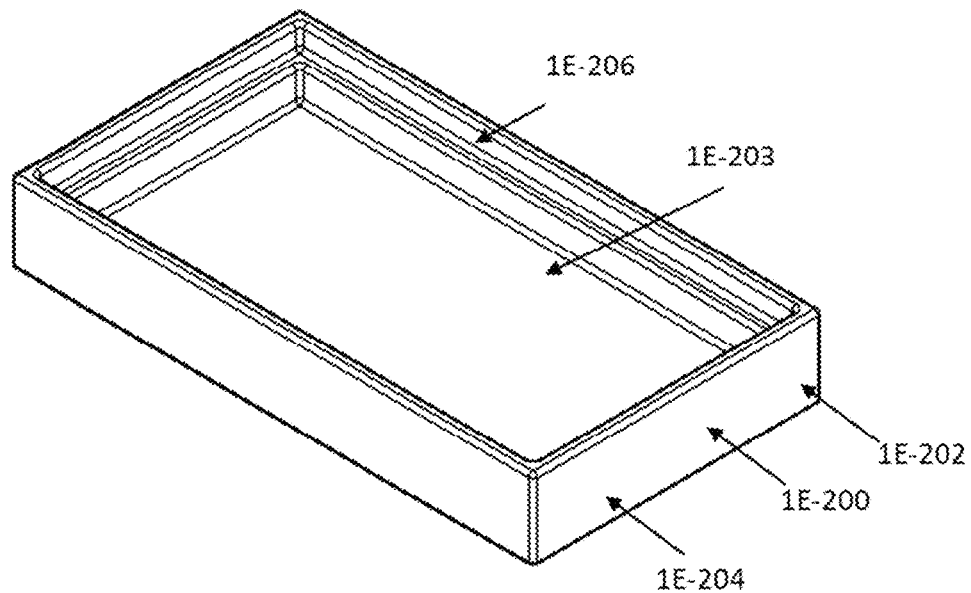
Figure 63:
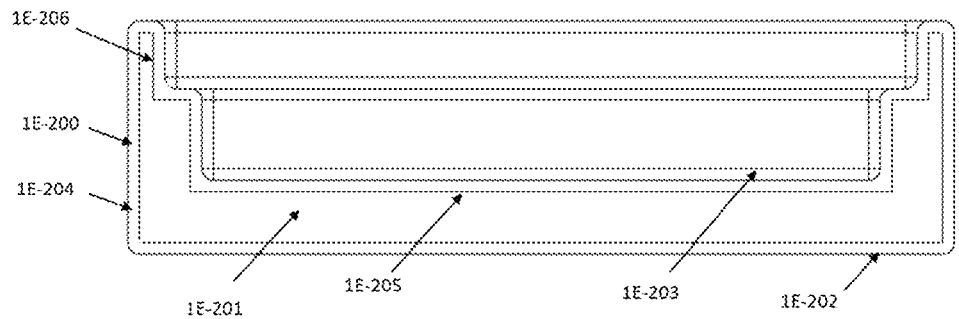
Figure 64:
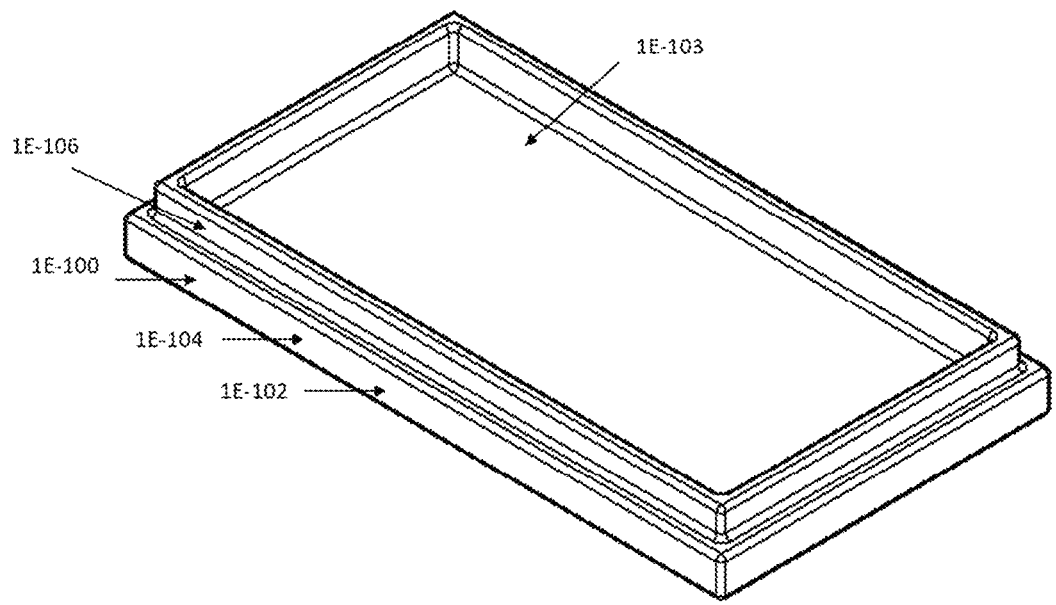
Figure 65:
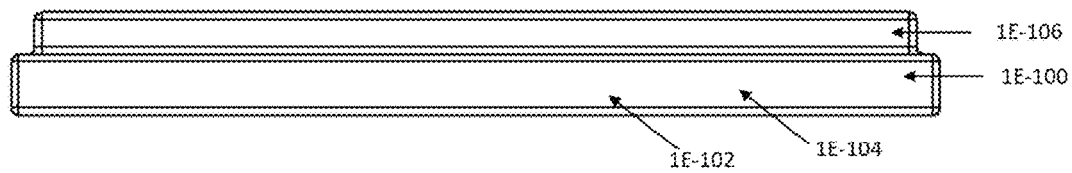
Figure 66:
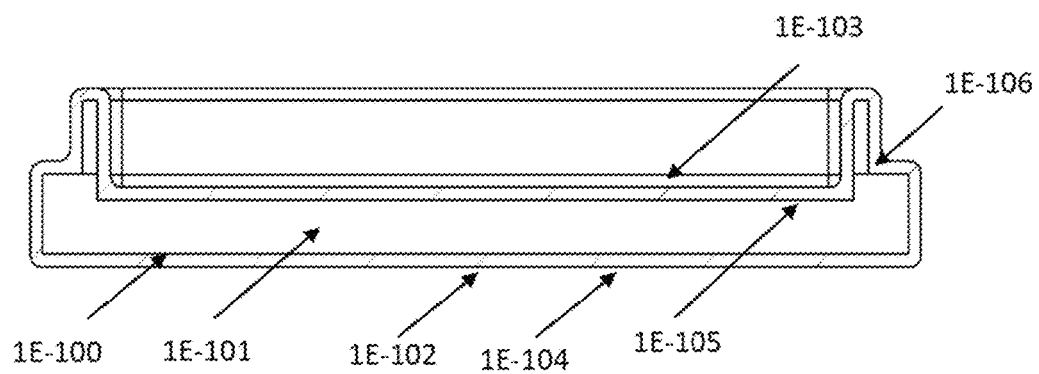
Figure 67:
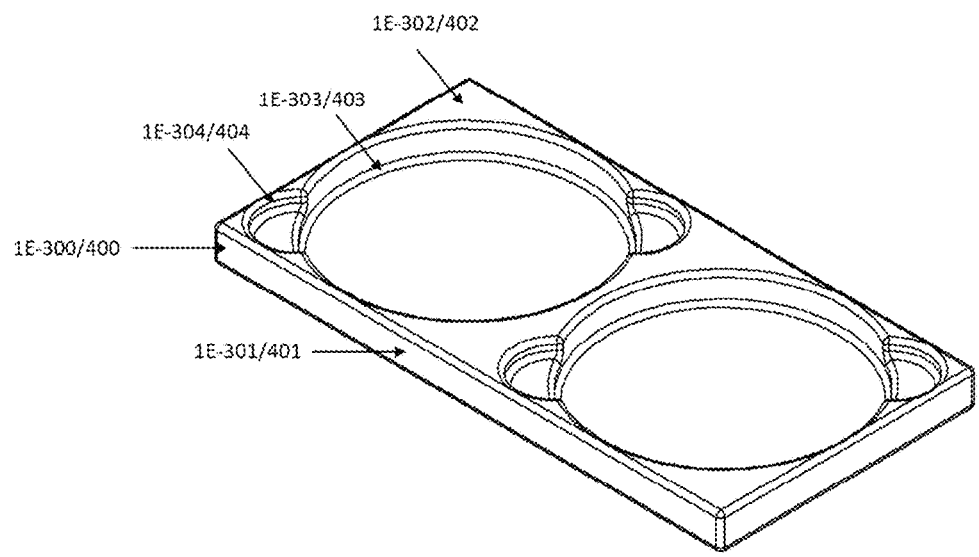
Figure 68:
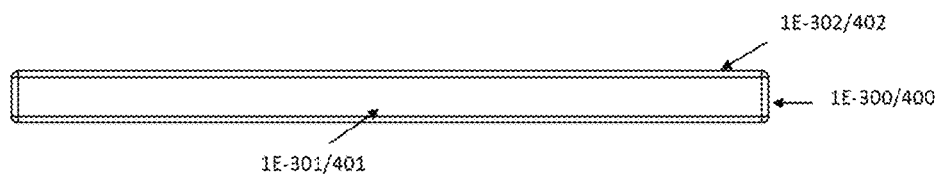
Figure 69:
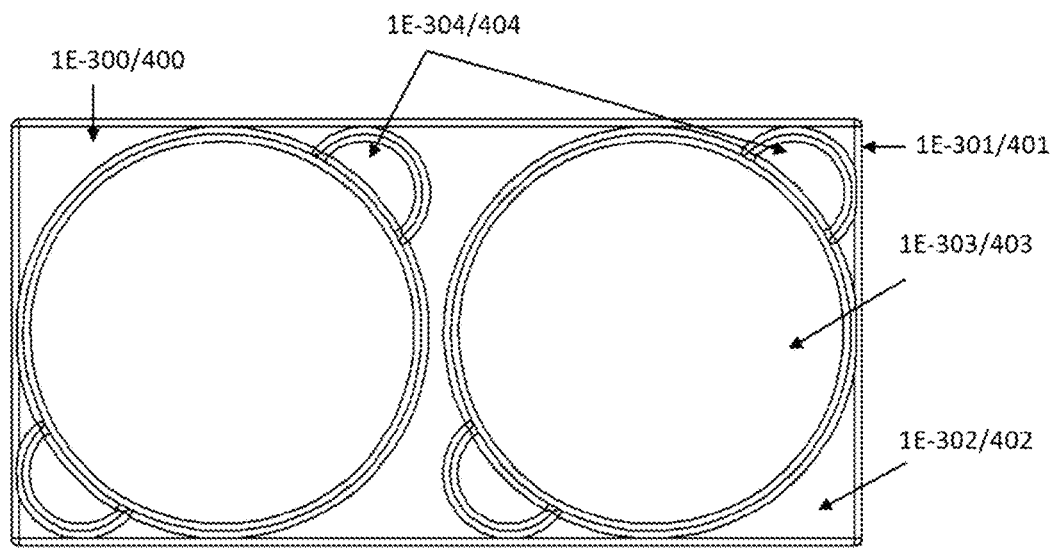

Exemplary Embodiment No. 1 (Vacuum Sealed High-Aspect Ratio Protective Case)

The protective case (1A, 1B, 1C, 1D, 1E) can be constructed of a rigid material of the following compositions: metal, TP, TPE, fiber reinforced composite, ceramic, or a combination of these materials. The protective case is composed of an upper half (1A-400, 1B-100, 1C-100, 1D-100, 1E-100) and a lower half (1A-300, 1B-200, 1C-200, 1D-200, 1E-200), that when mated together form an enclosure (1A, 1B, 1C, 1D, 1E) that is substantially sealed that can provide insulation to the enclosed auto-injector and may be watertight. The upper half (1A-400, 1B-100, 1C-100, 1D-100, 1E-100) and the lower half (1A-300, 1B-200, 1C-200, 1D-200, 1E-200) of the protective case can be composed of a rigid inner and outer wall (1A-305, 1A-404, 1B-103, 1B-202, 1C-103, 1C-104, 1C-203, 1C-204, 1D-102, 1D-202, 1E-102, 1E-202) that form the sealed vacuum chamber (1A-301, 1A-401, 1B-101, 1B-201, 1C-101, 1C-201, 1D-101, 1D-201, 1E-101, 1E-201). The two vacuum sealed halves insulate the disposed auto-injector to limit the heat transfer between the internal chamber and the outside environment. The sealed vacuum chambers are extended to the furthest point (1A-307, 1A-406, 1B-105, 1B-204, 1C-106, 1C-206, 1E-106, 1E-206) at the joints of the two halves to maximize the insulating properties of the case and limit thermal bridging to the interior of the device.

The connection between the upper half (1A-400, 1B-100, 1C-100, 1D-100, 1E-100) and lower half (1A-300, 1B-200, 1C-200, 1D-200, 1E-200) may be a threaded connection (1A-302, 1A-402, 1B-102, 1B-503), a friction fit (1C-102, 1C-202, 1E-106, 1E-206), or any other variation (1D-302, 1D-402) that may provide a sealed connection. The joint between the two halves may provide a watertight connection and in certain embodiments may utilize a gasket (1B-300). Furthermore, the watertight/water-resistant connection may be facilitated through the addition of a coating or separate material applied at the joint interface (1A-303, 1A-403). In certain embodiments the joint between the upper half (1A-400, 1B-100, 1C-100, 1D-100, 1E-100) and the lower half (1A-300, 1B-200, 1C-200, 1D-200, 1E-200) may be facilitated by the thermal barrier (1A-500, 1A-600, 1B-400, 1B-500, 1C-300, 1C-400, 1D-300, 1D-400, 1E-300, 1E-400) affixed to the interior of the housing. The thermal barrier may be affixed to the housing (1A-306, 1A-405, 1B-104, 1B-203, 1C-105, 1C-205, 1D-103, 1D-203, 1E-103, 1E-203) through adhesive, mechanical means, or form molded (1A-501, 1A-601, 1B-401, 1B-501, 1C-301, 1C-401, 1D-301, 1D-401, 1E-301, 1E-401). The sealed connection may be performed via a threaded connection on the insulation sleeve (1B-503) and a corresponding threaded connection on the inside of the top housing (1B-102), such that the threads are concealed once the housings are mated together.

The case may provide additional thermal insulation through a thermal barrier (1A-500, 1A-600, 1B-400, 1B-500, 1C-300, 1C-400, 1D-300, 1D-400, 1E-300, 1E-400) to improve the insulating properties. The additional thermal barrier (1A-500, 1A-600, 1B-400, 1B-500, 1C-300, 1C-400, 1D-300, 1D-400, 1E-300, 1E-400) may consist of a TP, TPE, open or closed cell foam layer or combinations of such, which may or may not be one complete piece but can include multiple pieces that may interlock (1A-503, 1A-603, 1B-402, 1B-502, 1C-302, 1C-402, 1D-302, 1D-402, 1E-302, 1E-402) when the two halves of the case are mated together, forming a substantially sealed barrier. In certain embodiments the device enclosure may be lined with an insulating sleeve (1A-500, 1A-600, 1B-400, 1B-500, 1C-300, 1C-400, 1D-300, 1D-400, 1E-300, 1E-400) formed of one or two pieces, which interlock through stepped ledges or interference fits (1A-503, 1A-603, 1B-402, 1B-502, 1C-302, 1C-402, 1D-302, 1D-402, 1E-302, 1E-402). In certain embodiments the insulation barriers form a well or cradle (1A-502, 1A-602, 1B-403, 1B-505, 1C-503, 1D-303, 1D-403, 1E-303, 1E-403) for stabilizing the device and may dampen any relative motion between the device and the protective case (1A, 1B, 1C, 1D, 1E). Alternatively, the insulation barrier and the stabilizing cradle may be two separate components (1C-500). The material selection for the insulation sleeve and cradle will be such that it minimizes the thermal conductivity and maximizes vibration damping. Additionally, the thermal barrier(s) may protrude from the joint between the upper half (1A-400, 1B-100, 1C-100, 1D-100, 1E-100) and the lower half (1A-300, 1B-200, 1C-200, 1D-200, 1E-200) and provide an interface for the user to separate the halves (1D-304, 1D-404). The insulation barrier may also form a cavity that releasably receives (1B-504, 1E-304, 1E-404) at least a portion of the auto-injector device and provides access for the user to remove the device from the case (1A-304). Furthermore, the insulation barrier or rigid upper or lower halves may provide a means of orientation for the device to be stored and as such removed.

Furthermore, certain embodiments may be configured to protect more than one device (1E) as well as hold dissimilar devices if deemed necessary. The configuration of holding multiple devices is not limited to a horizontal or vertical layout of stacking, but instead allows for the best optimized method of storing the devices while maintaining a relatively low-profile case.

In certain embodiments to aid in the insulating properties of the case, the internal surfaces of the vacuum sealed chambers may be polished or lined with a reflective coating, or similar means to reduce the heat transfer by radiation (1A-308, 1A-407, 1B-107, 1B-206, 1C-108, 1C-208, 1D-105, 1D-205, 1E-105, 1E-205). Additionally, some embodiments may contain an exterior coating (1A-100, 1A-200, 1B-106, 1B-205, 1C-107, 1C-207, 1D-104, 1D-204, 1E-104, 1E-204) or applied layer(s) of dissimilar material or combination of the two, to increase the insulating value of the exterior wall. Furthermore, the exterior coating (1A-100, 1A-200, 1B-106, 1B-205, 1C-107, 1C-207, 1D-104, 1D-204, 1E-104, 1E-204) or applied layer of dissimilar material or a combination of the two, to the exterior may provide a texture or profile to the case to assist the user in handling (1A-101, 1A-201). This exterior coating or layer(s) of dissimilar material or combination of such may perform the following functionalities; improve the ergonomics of the case, aid in reducing the induced vibrations from external loading, contribute to case aesthetics, provide structural support, provide labeling (1A-102), etc.

Furthermore, embodiments of the case may provide a power source (1A-701) to assist in monitoring the conditions of the case both internal and external, and providing connectivity of the case with other smart devices. The case may provide the user with an interface (1A-700) for monitoring internal device cavity and external conditions to better maintain the enclosed device.

In addition to providing a means of monitoring and connecting the case wirelessly to external devices, the case can provide a means of physically attaching to other external objects (1A-104). Additionally, certain embodiments may include the use of a combination of rigid and elastic cases (3H) to provide improved accessibility or portability. In one aspect the combination of the rigid and elastic cases may provide a means to affix the case or combination of cases to such everyday items like a backpack, lanyard, bike, keys, etc. The attachment mechanism may include a wrist strap, a wrist band, a clip, a tether, a necklace, a pin, a clamp, a mount, a tab forming an eyelet, an adhesive layer, a hand grip surface, and/or combinations thereof.

Exemplary Embodiment No. 2 (Vacuum Sealed Low-Aspect Ratio Protective Case)

Figure 70:
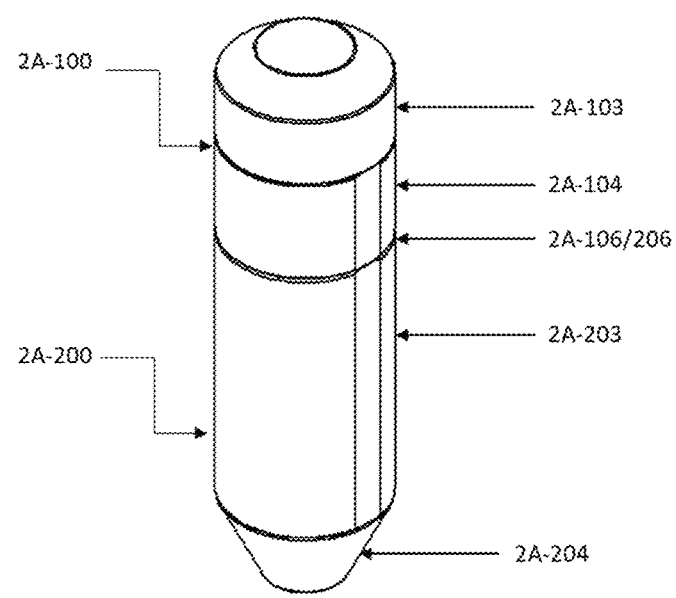
FIGS. 70-97 are schematic views of a vacuum sealed protective case for carrying a low aspect ratio auto-injector, according to example embodiments.
Figure 71:
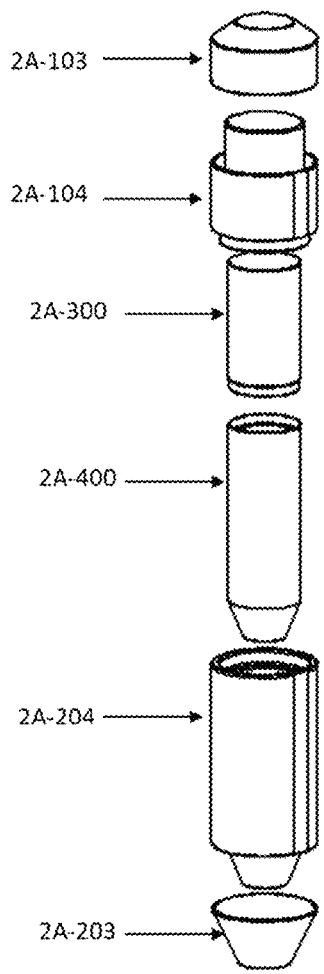
Figure 72:
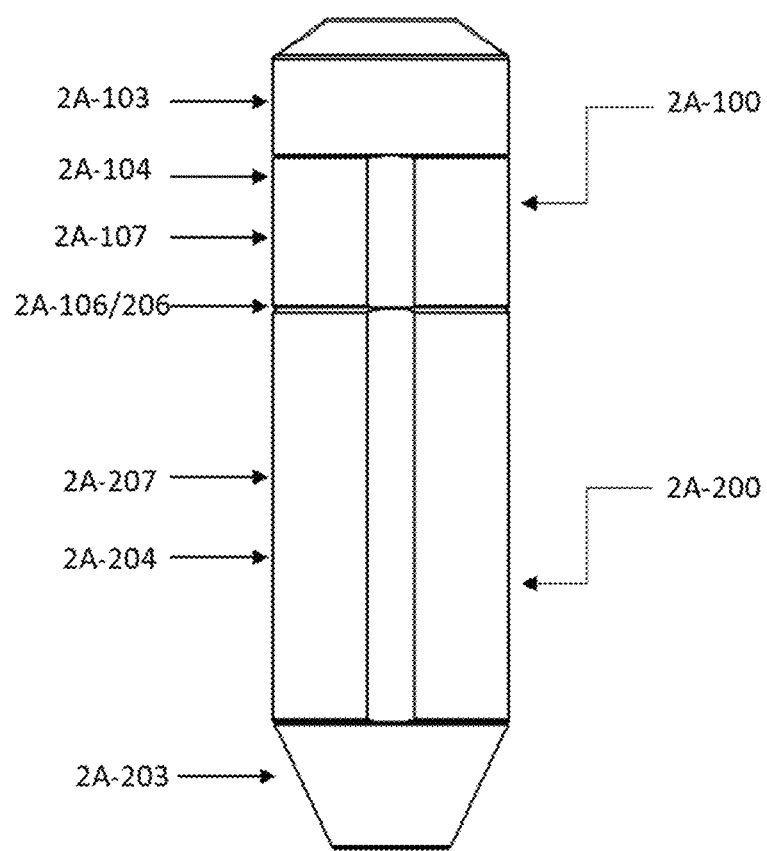
Figure 73:
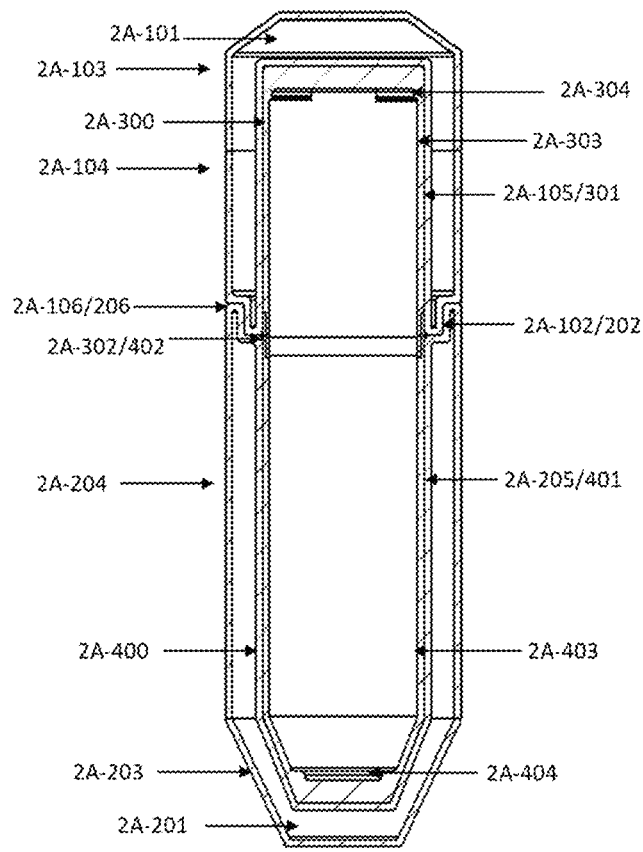
Figure 74:
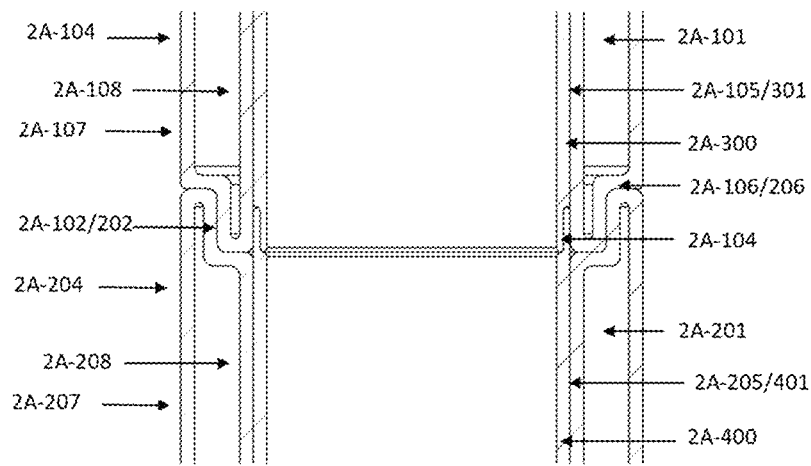
Figure 75:
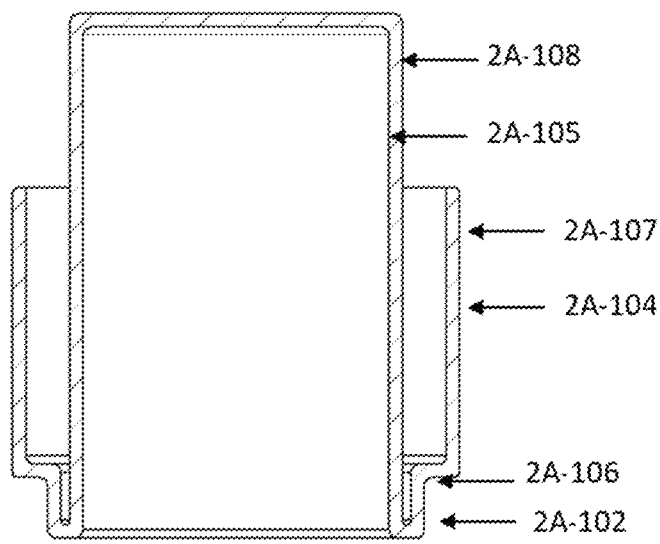
Figure 76:
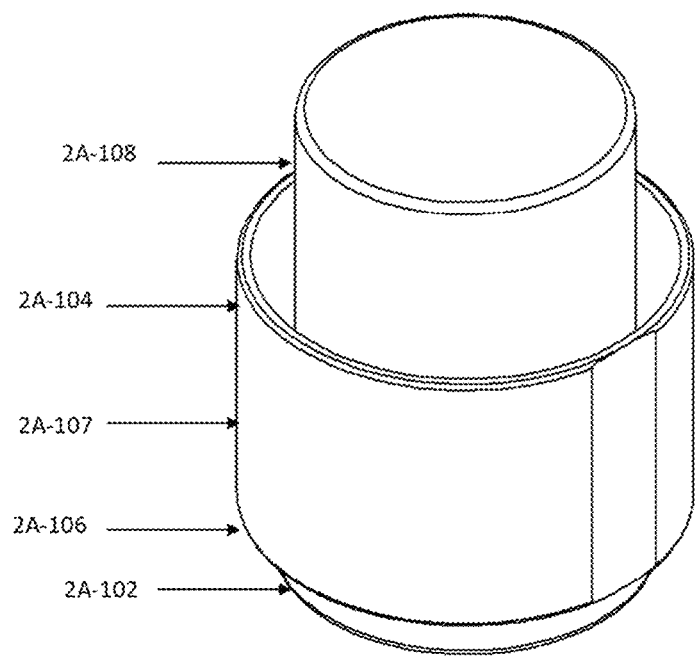
Figure 77:
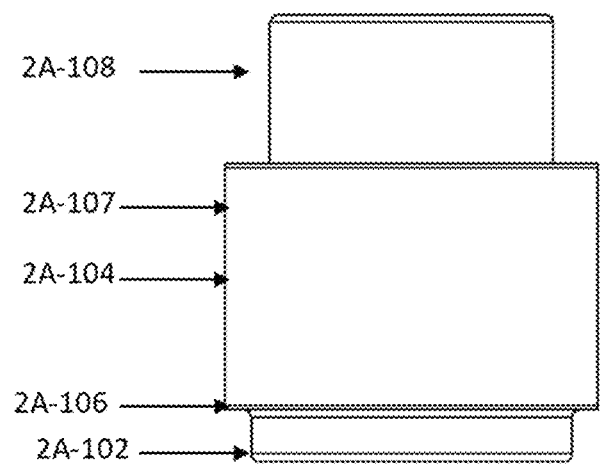
Figure 78:
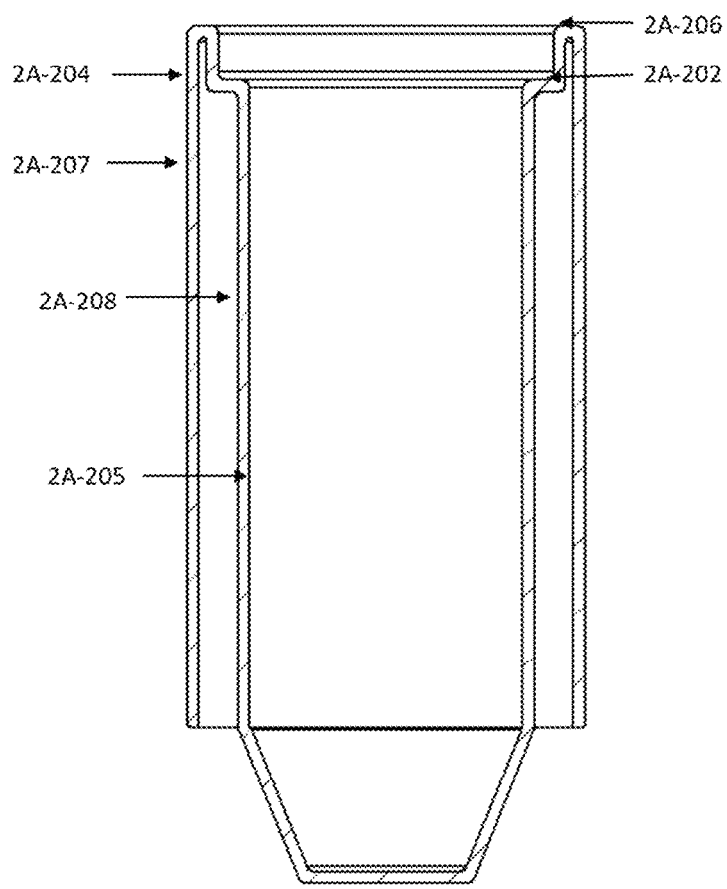
Figure 79:
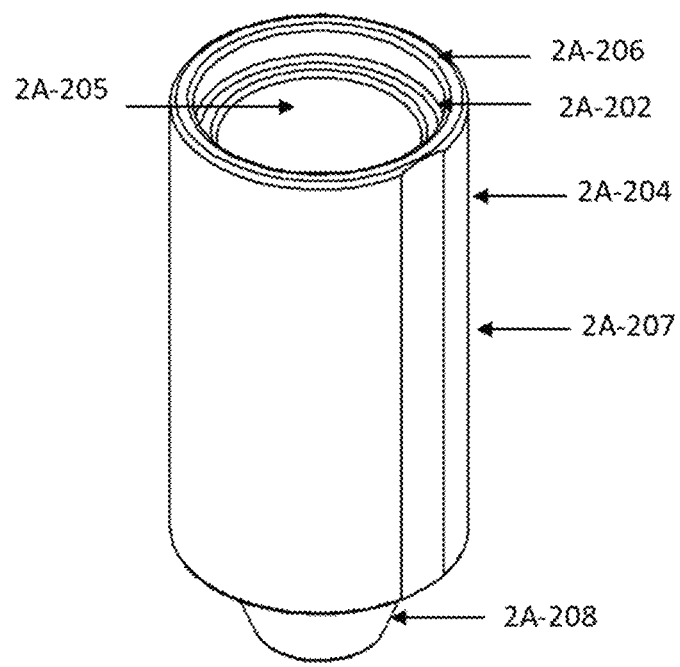
Figure 80:
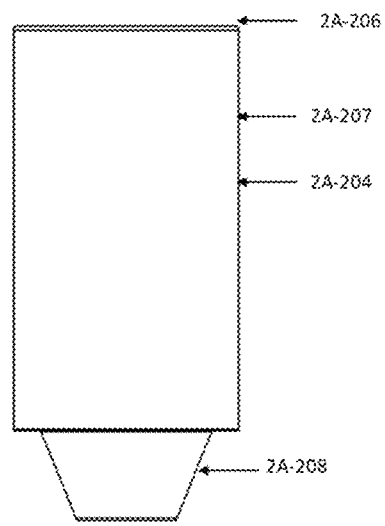
Figure 81:
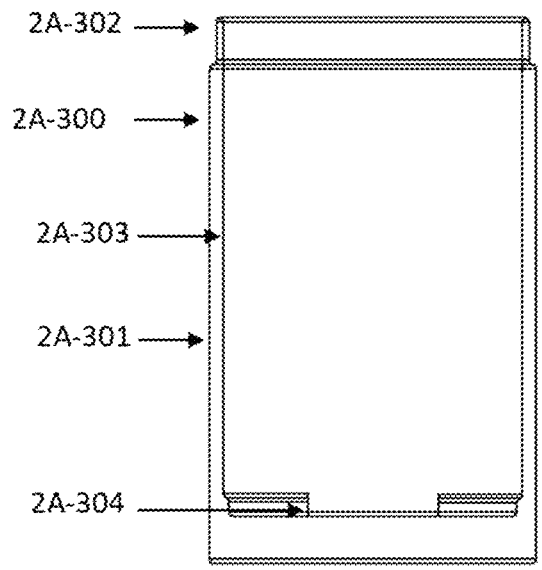
Figure 82:
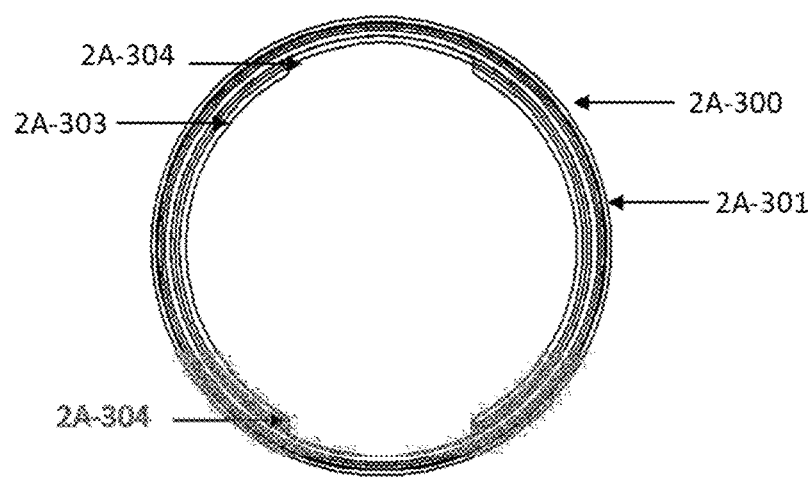
Figure 83:
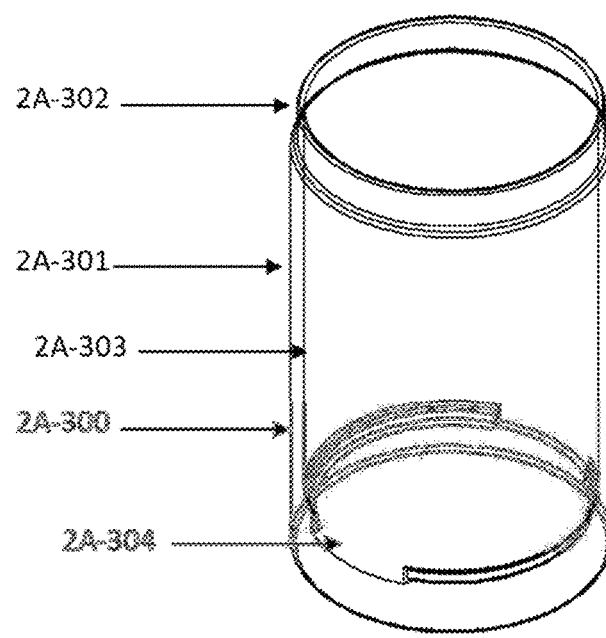
Figure 84:
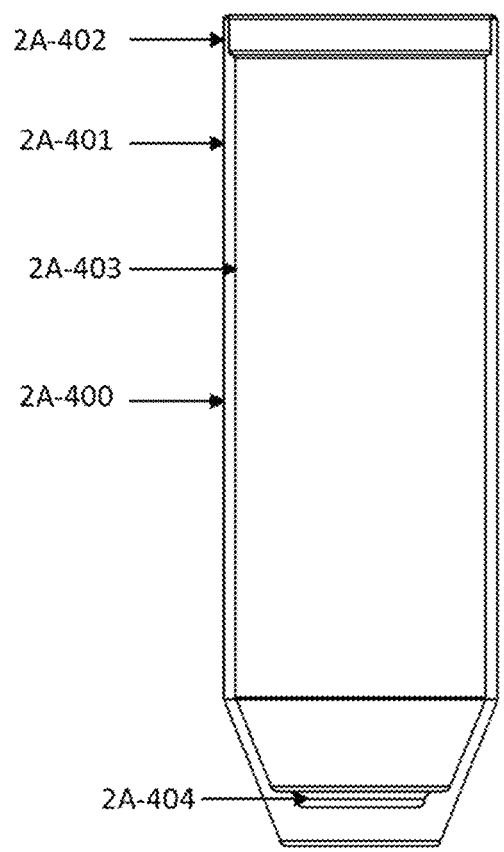
Figure 85:
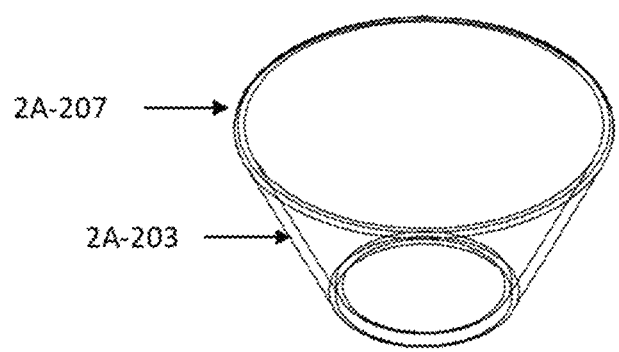
Figure 86:
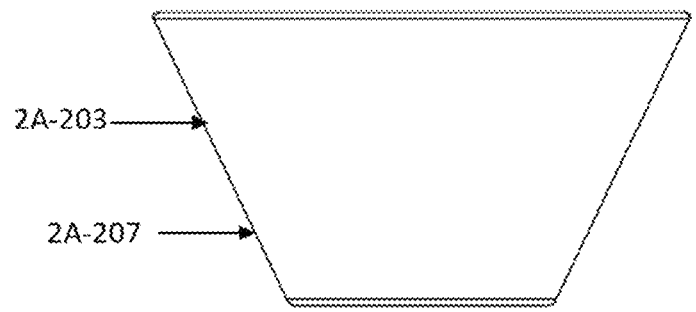
Figure 87:
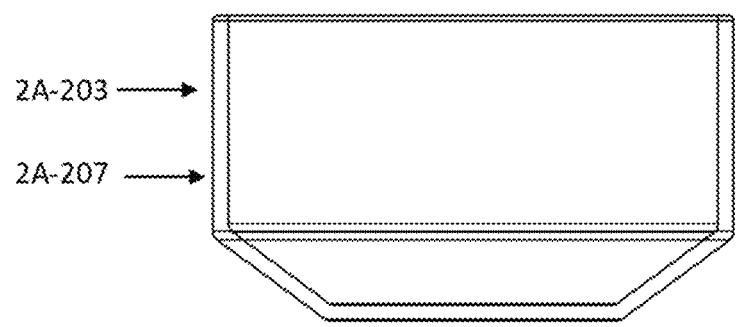
Figure 88:
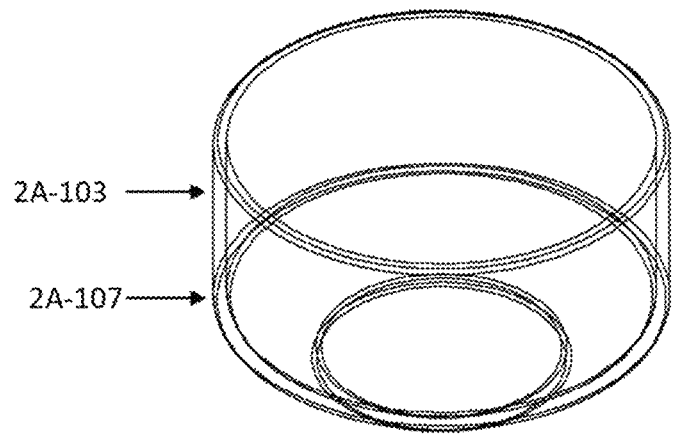
Figure 89:
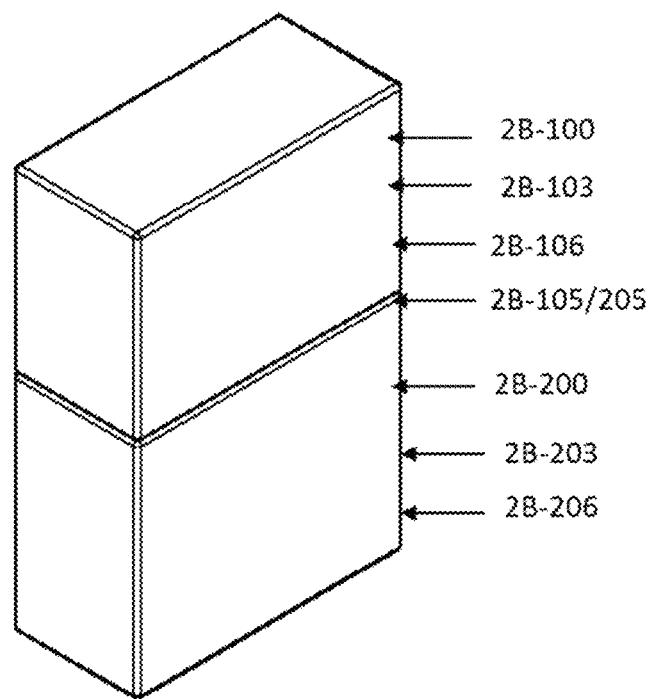
Figure 90:
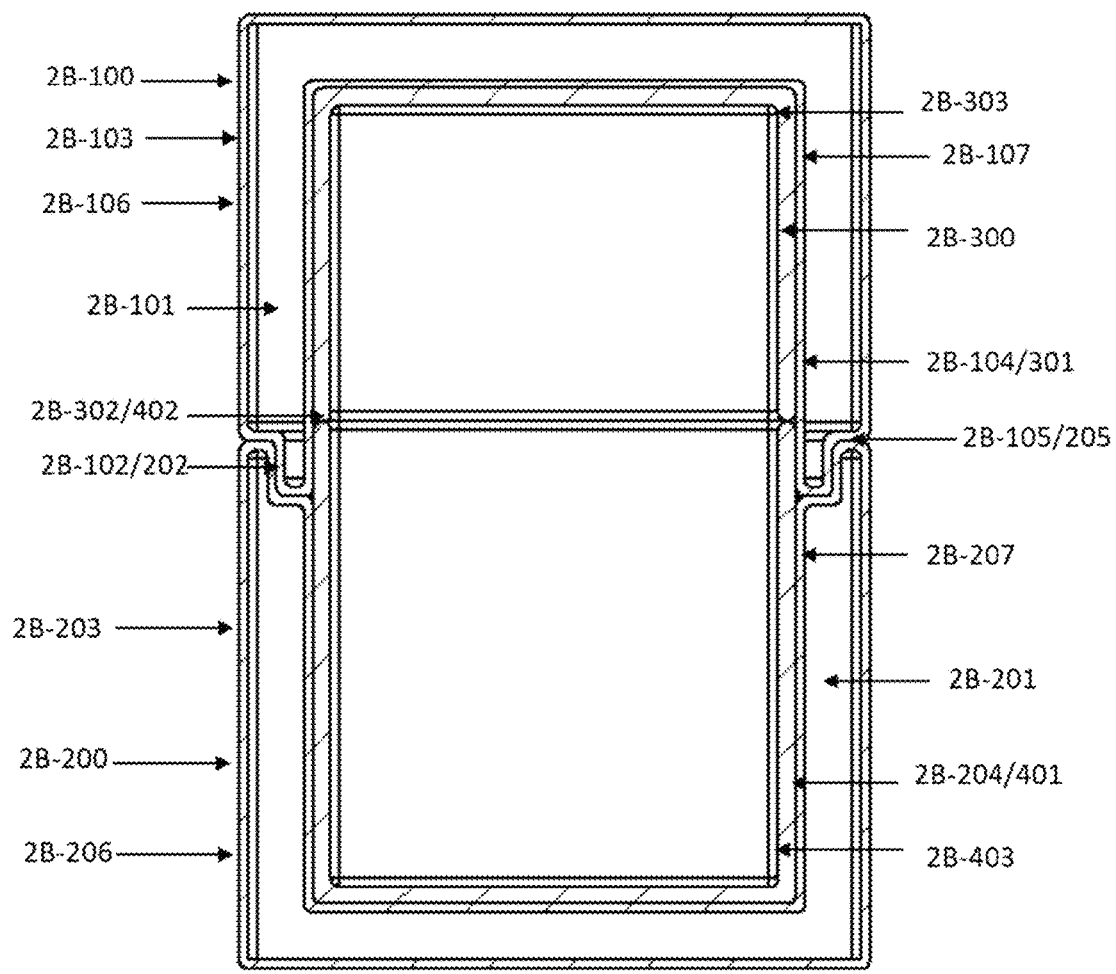
Figure 91:
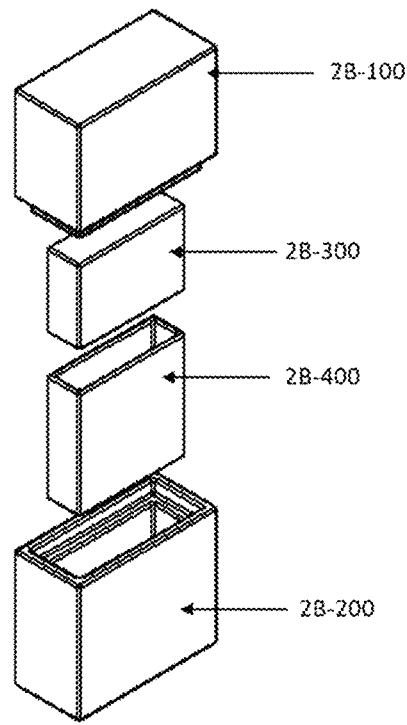
Figure 92:
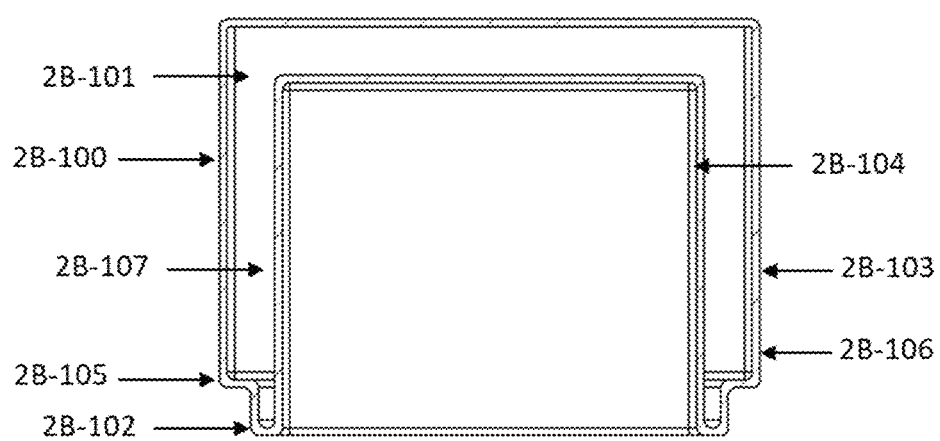
Figure 93:
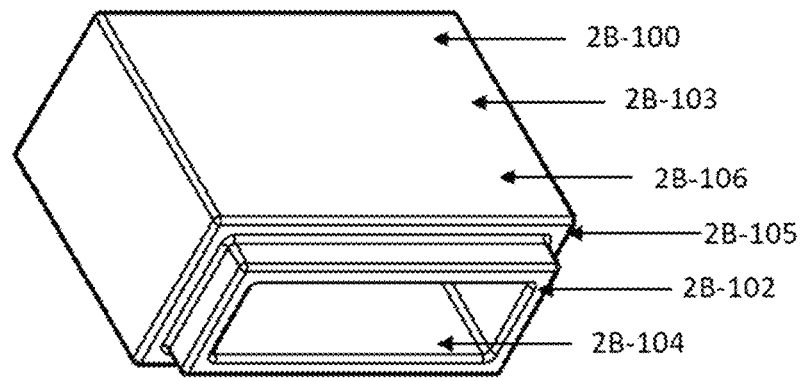
Figure 94:
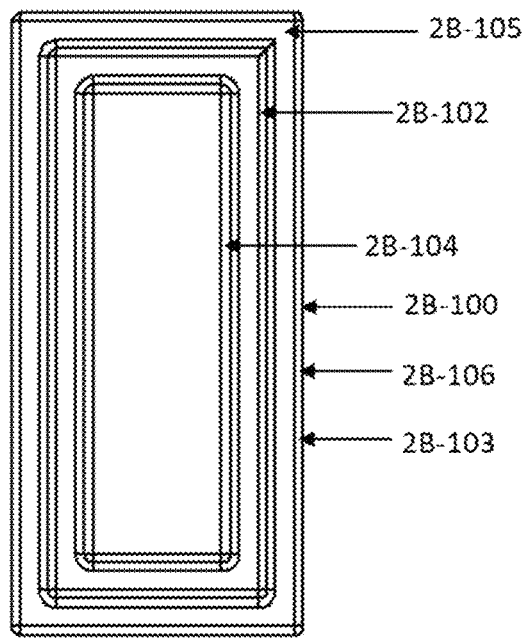
Figure 95:
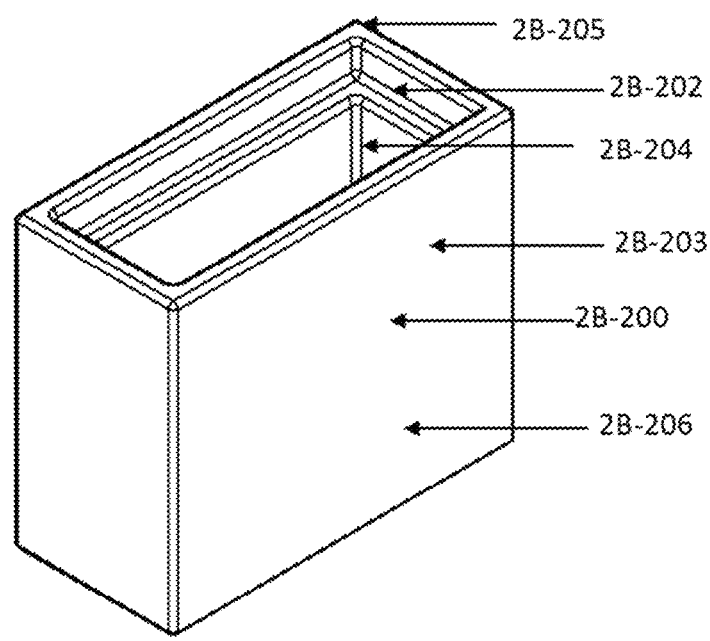
Figure 96:
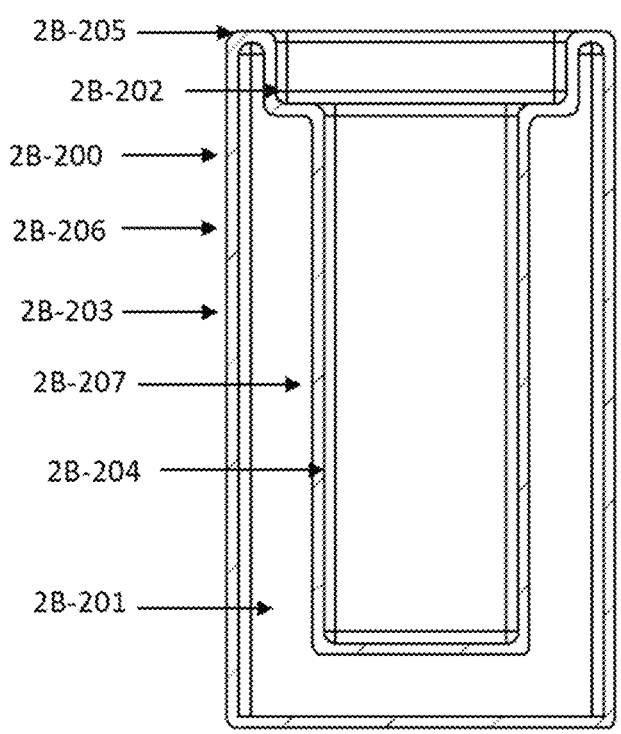
Figure 97:
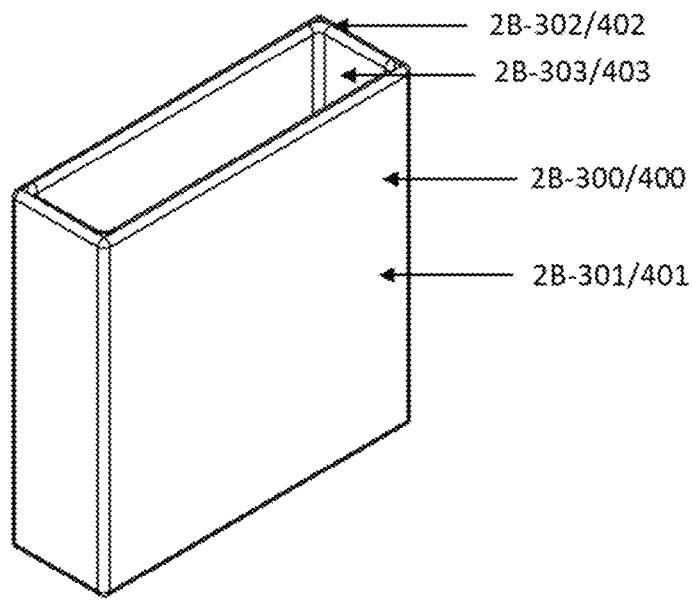

The embodiments depicted in FIGS. 70-97 mimic the functionality of exemplary embodiment No. 1 where: (I) the protective case can be constructed of a rigid material of the following compositions metal, TP, TPE, fiber reinforced composite, ceramic, or combination of such materials; (II) the protective case is composed of an upper half (2A-100, 2B-100) and a lower half (2A-200, 2B-200), that when mated together form an enclosure (2A, 2B) that is substantially sealed that can provide insulation to the enclosed auto-injector and may be watertight/water-resistant; (III) the upper half (2A-100, 2B-100) and the lower half (2A-200, 2B-200) of the protective case (2A, 2B) are composed of a rigid inner and outer wall (2A-103, 2A-104, 2A-203, 2A-204, 2B-103, 2B-203) that form the sealed vacuum chamber (2A-101, 2A-201, 2B-101, 2B-201); (IV) the sealed vacuum chambers are extended to the furthest point at the joints of the two halves (2A-106, 2A-206, 2B-105, 2B-206) to maximize the insulating properties of the case and limit thermal bridging to the interior of the device. The case may be composed of two sealed vacuum chambers (2A-101, 2A-201, 2B-101, 2B-201) of proportional or non-proportional size. In one embodiment, the vacuum sealed chamber is composed of two parts (2A-103, 2A-104, 2A-203, and 2A-204).

The connection between the upper and lower halves may be a threaded connection, a frictional interference fit (2A-102, 2A-202, 2B-102, 2B-202), or any other variation that may provide a sealed connection. The joint between the two halves may provide a watertight/water-resistant connection and in certain embodiments may utilize a gasket. Furthermore, the watertight/water-resistant connection may be facilitated through the addition of a coating or separate material applied at the joint interface. In certain embodiments the joint between the upper half (2A-100, 2B-100) and the lower half (2A-200, 2B-200) may be facilitated by the thermal barrier (2A-300, 2A-400, 2B-300, 2B-400) affixed to the interior of the housing. The thermal barrier may be affixed to the housing (2A-105, 2A-205, 2B-104, 2B-204) through an adhesive, mechanical means, or form molded (2A-301, 2A-401, 2B-301, 2B-401). The sealed connection may be performed via a threaded connection on the insulation sleeve and a corresponding threaded connection on the inner top housing, such that the threads are concealed once the housings are mated together. Similarly, the connection may be performed using a friction fit or interference connection (2A-302, 2A-402, 2B-302, 2B-402).

The case may provide additional thermal insulation through a thermal barrier to aid in the insulating properties (2A-300, 2A-400, 2B-300, 2B-400). The additional thermal barrier may consist of a TP, TPE, open or closed cell foam layer or combinations of such, which may or may not be one complete piece, but consists of multiple pieces that may interlock (2A-302, 2A-402, 2B-302, 2B-402) when the two halves of the case are mated together, forming a substantially sealed barrier. In certain embodiments the device enclosure may be lined with an insulating sleeve (2A-300, 2A-400, 2B-300, 2B-400) formed of one or two pieces, that interlock through stepped ledges or interference fits (2A-302, 2A-402, 2B-302, 2B-402). In certain embodiments the insulation barriers form a well or cradle (2A-303, 2A-403, 2B-303, 2B-403) for stabilizing the device and dampen any relative motion between the device and the protective case. Alternatively, the insulation barrier and the stabilizing cradle may be two separate components. The material selection for the insulation sleeve and cradle will be such that it minimizes the thermal conductivity and maximizes the shock absorption properties. Additionally, the thermal barrier(s) may protrude from the joint between the upper and lower halves and provide an interface for the user to separate the halves. The insulation barrier may also form a cavity that releasably receives at least a portion of the auto-injector device and provides access for the user to remove the device from the case. Furthermore, the insulation barrier or rigid upper or lower halves may provide a means of orientation (2A-304, 2A-404) for the device to be stored and as such removed.

Furthermore, certain embodiments may be configured to protect more than one device as well as hold dissimilar devices if deemed necessary. The configuration of holding multiple devices is not limited to a horizontal or vertical layout of stacking. The configuration allows for the method of storing multiple auto-injector devices while maintaining a low-profile case.

In certain embodiments to aid in the insulating properties of the case (2A, 2B), the internal surfaces of the vacuum sealed chambers (2A-101, 2A-201, 2B-101, 2B-201) may be polished or lined with a reflective coating (2A-108, 2A-208, 2B-107, 2B-207), or similar means to reduce the heat transfer through radiation. Additionally, some embodiments may contain an exterior coating or applied layer(s) of dissimilar material or combination of the two, to increase the insulating value of the exterior wall (2A-107, 2A-207, 2B-106, 2B-206). Furthermore, the exterior coating or exterior layer of dissimilar material or combinations of the two, to the exterior may provide a texture (2A-107, 2A-207, 2B-106, 2B-206) or profile to the case to assist the user in handling or gripping. This exterior coating or layer(s) of dissimilar material or combination of such may perform the following functionalities; increase the ergonomics of the case, aid in reducing the induced vibrations from external loading, assisting in case aesthetics, provide structural support, provide labeling, etc.

Furthermore, embodiments of the case may provide a power source to assist in monitoring the conditions of the internal device cavity and external environment and providing connectivity of the case with other smart devices. The case may provide the user with an interface for monitoring internal device cavity and external conditions to better maintain the enclosed device.

In addition to providing a means of monitoring and connecting the case wirelessly to external devices the case can provide a means of physically attaching the case to other external objects. Additionally, certain embodiments may include the use of a combination of rigid and elastic cases to provide a more accessible or portable means (3H). In one aspect the combination of the rigid and elastic cases may provide a means to affix the case or combination of cases to such everyday items like a backpack, lanyard, bike, keys, etc. The attachment mechanism may include a wrist strap, a wrist band, a clip, a tether, a necklace, a pin, a clamp, a mount, a tab forming an eyelet, an adhesive layer, a hand grip surface, and/or combinations thereof.

Exemplary Embodiment No. 3 (Protective Cases that Enable Increased Portability of Auto-Injectors)

Figure 98:
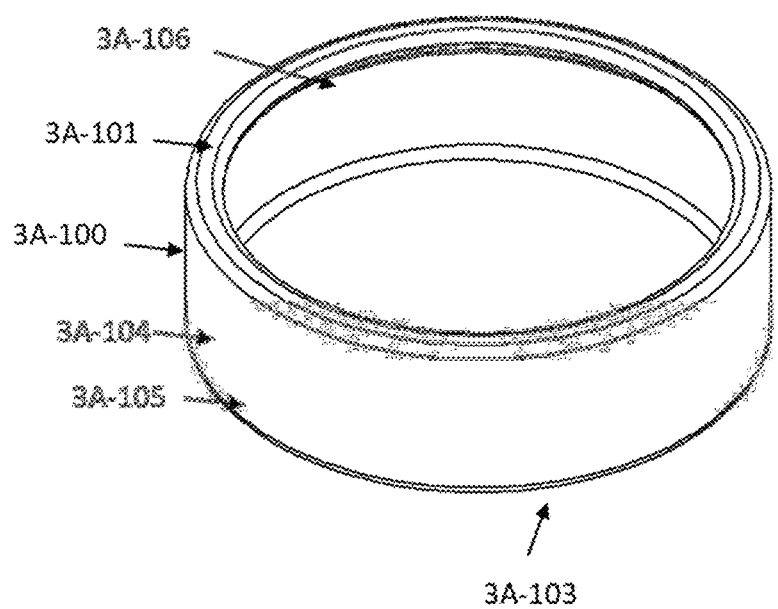
FIGS. 98-126 are schematic views of a non-vacuum sealed protective case for carrying a high aspect ratio auto-injector and for carrying a low aspect ratio auto-injector, according to example embodiments.
Figure 99:
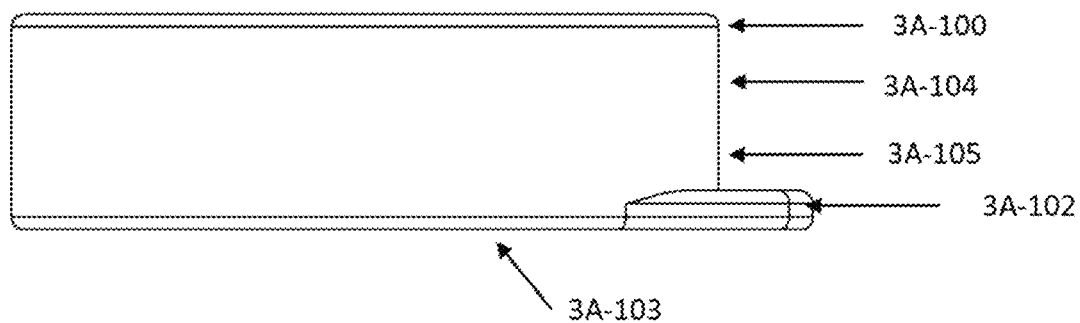
Figure 100:
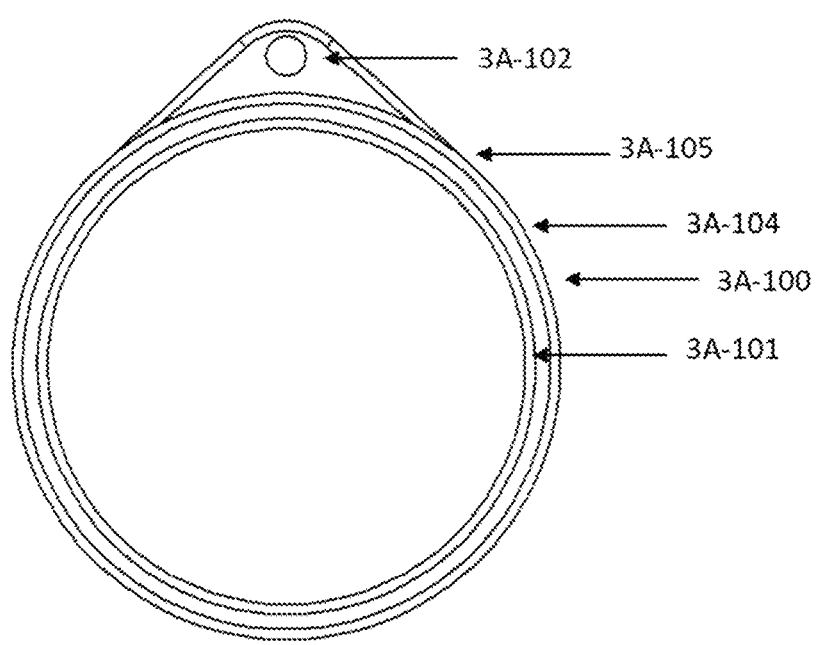
Figure 101:
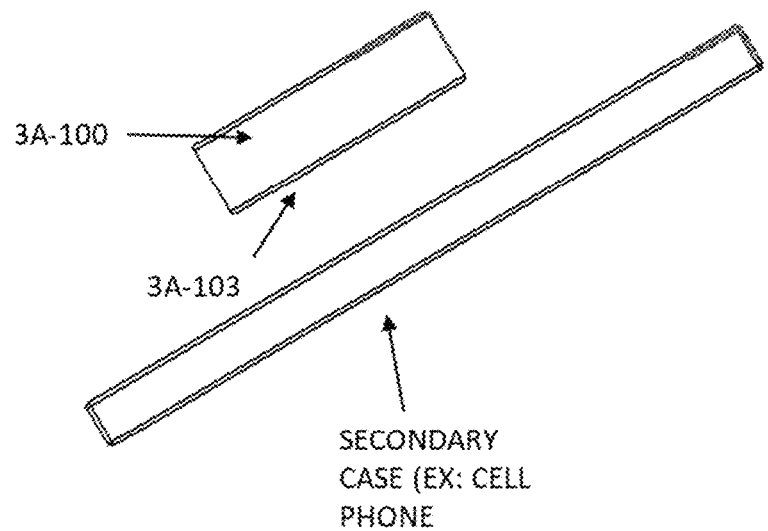
Figure 102:
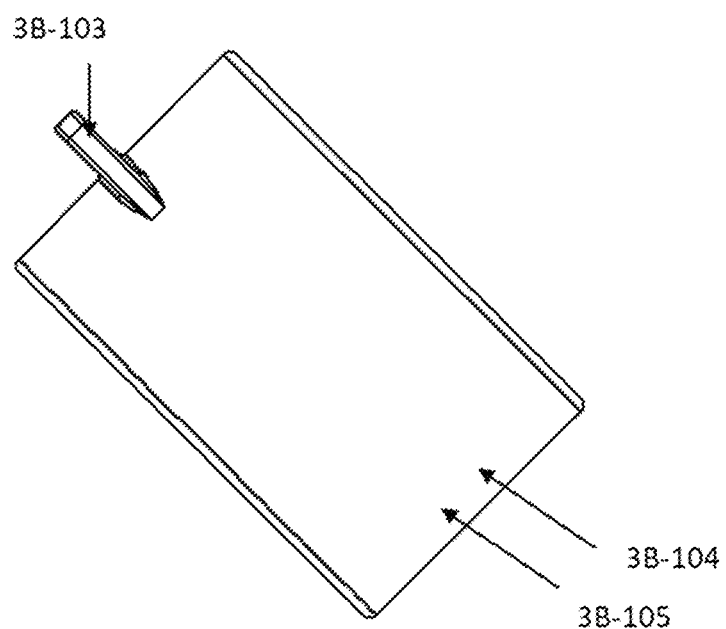
Figure 103:
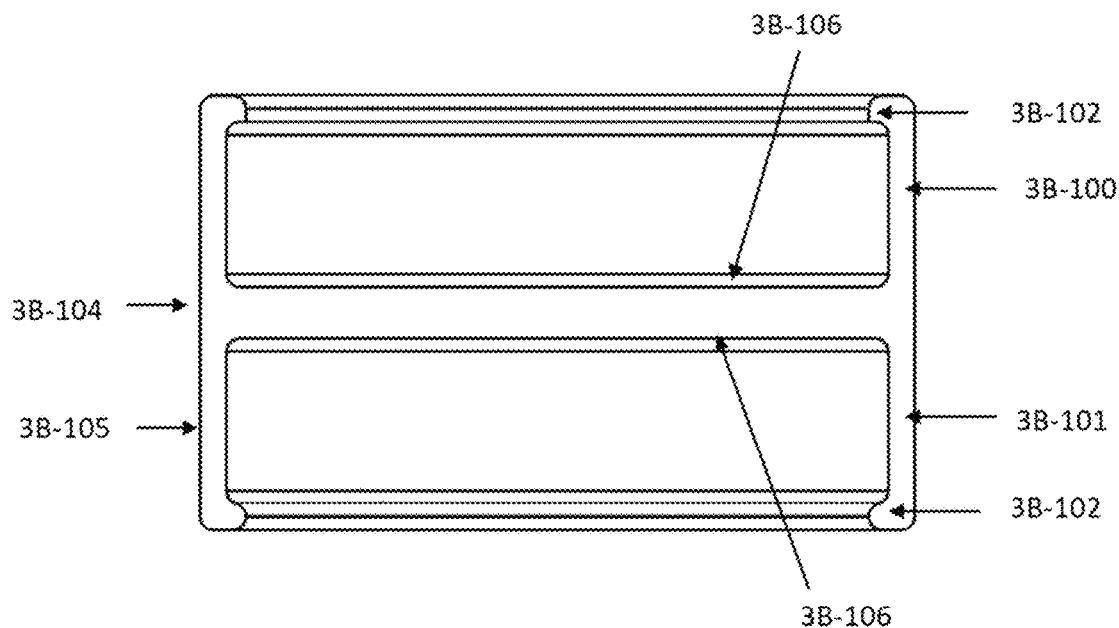
Figure 104:
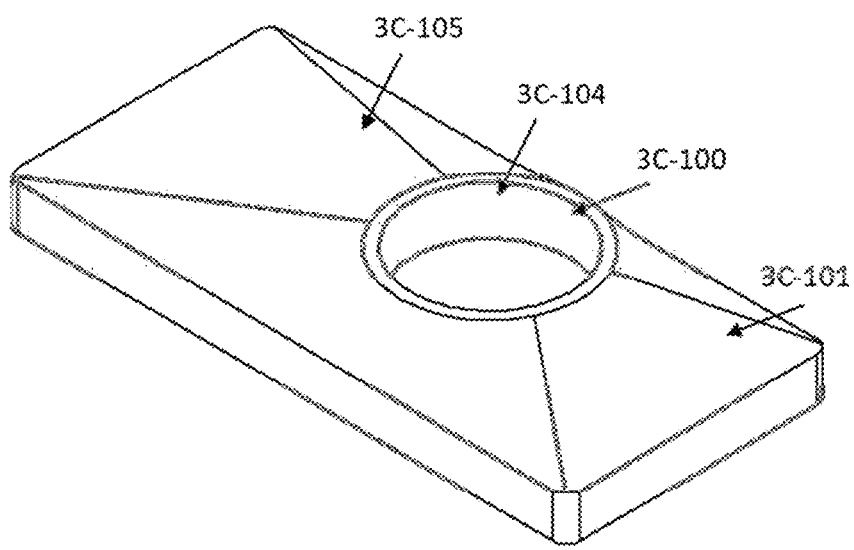
Figure 105:
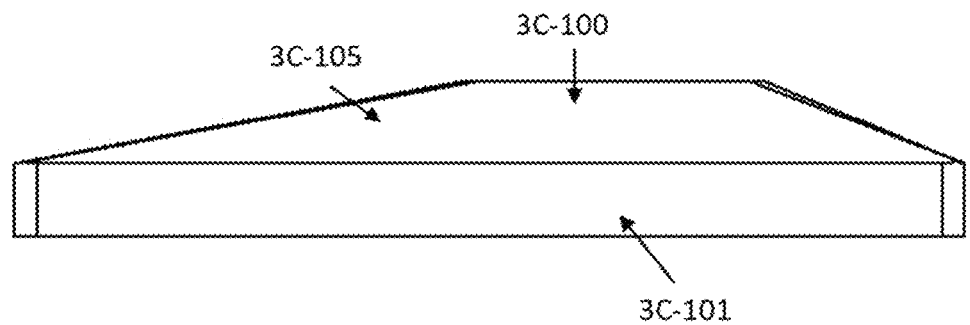
Figure 106:
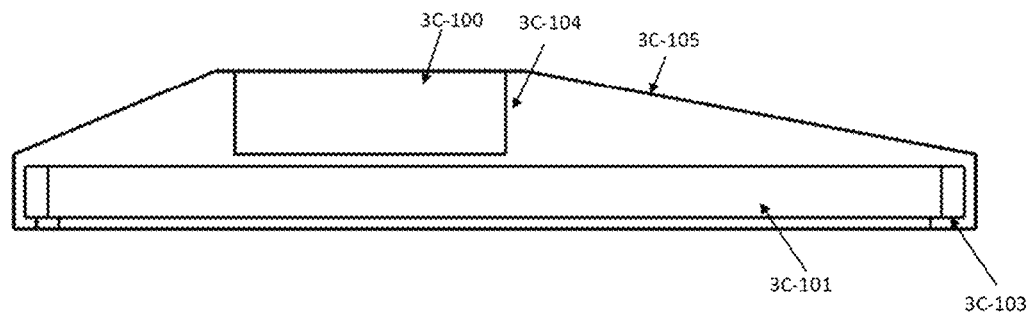
Figure 107:
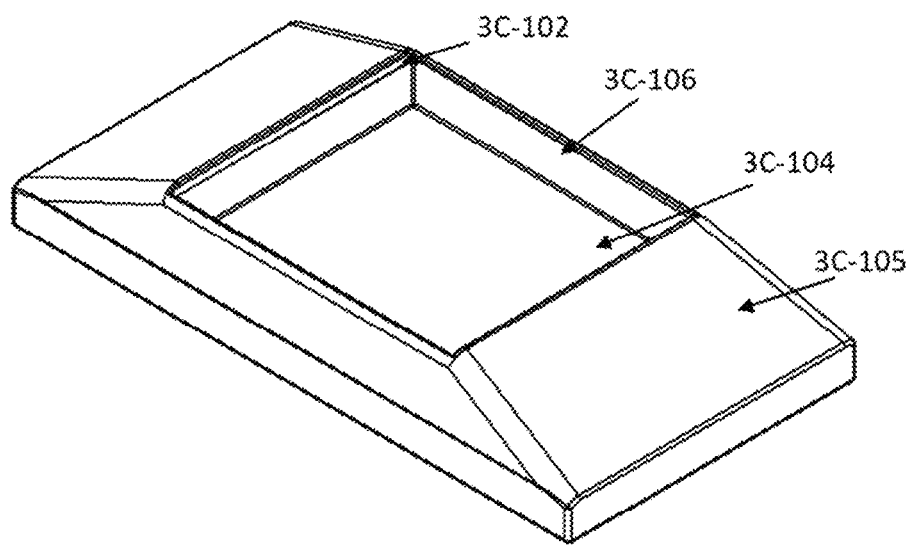
Figure 108:
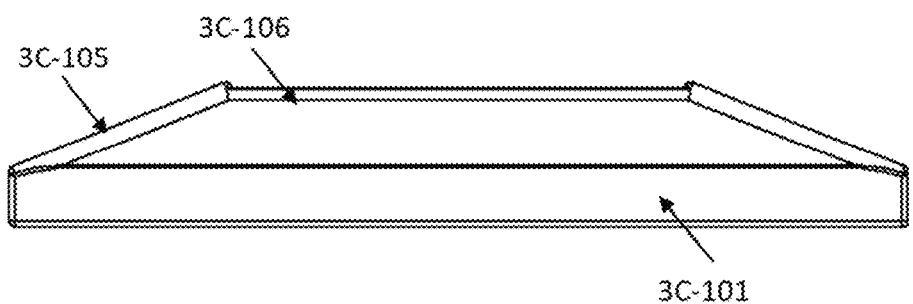
Figure 109:
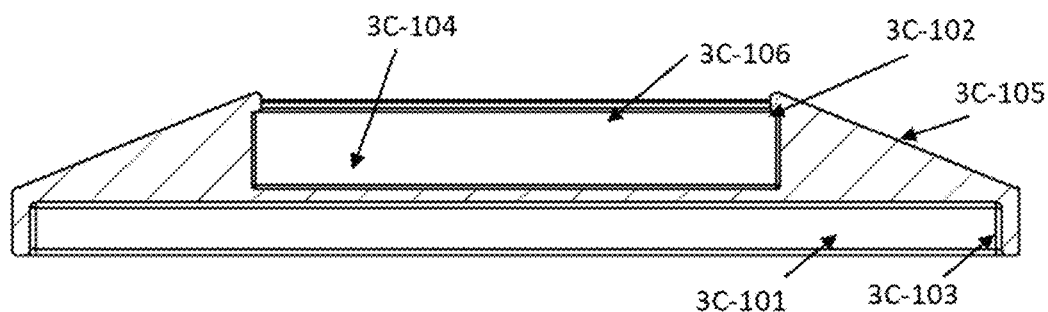
Figure 110:
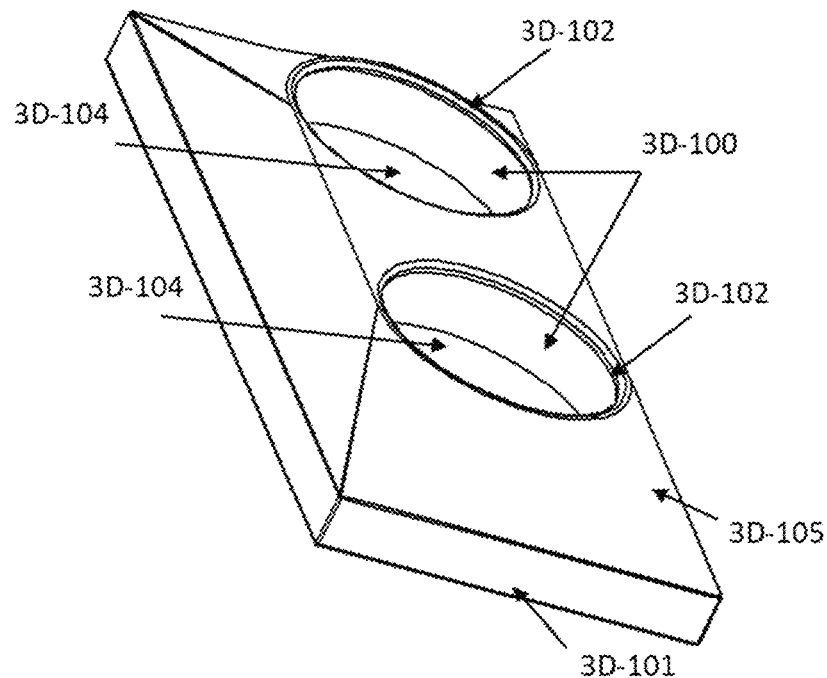
Figure 111:
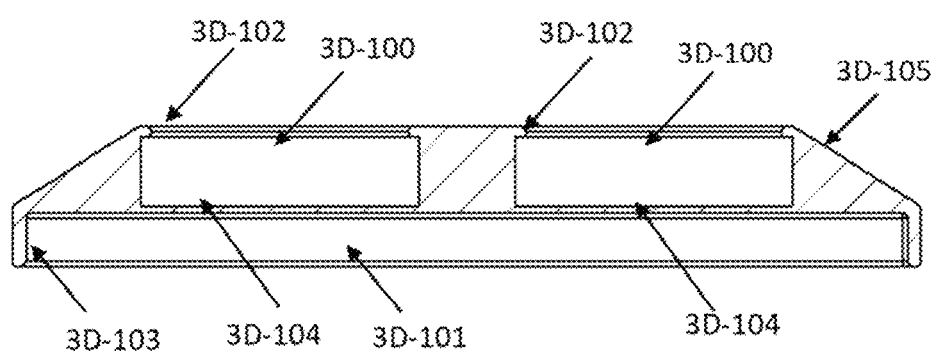
Figure 112:
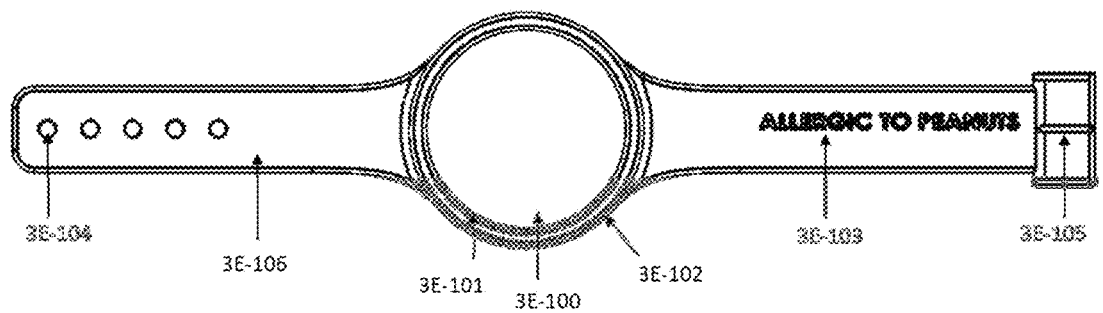
Figure 113:
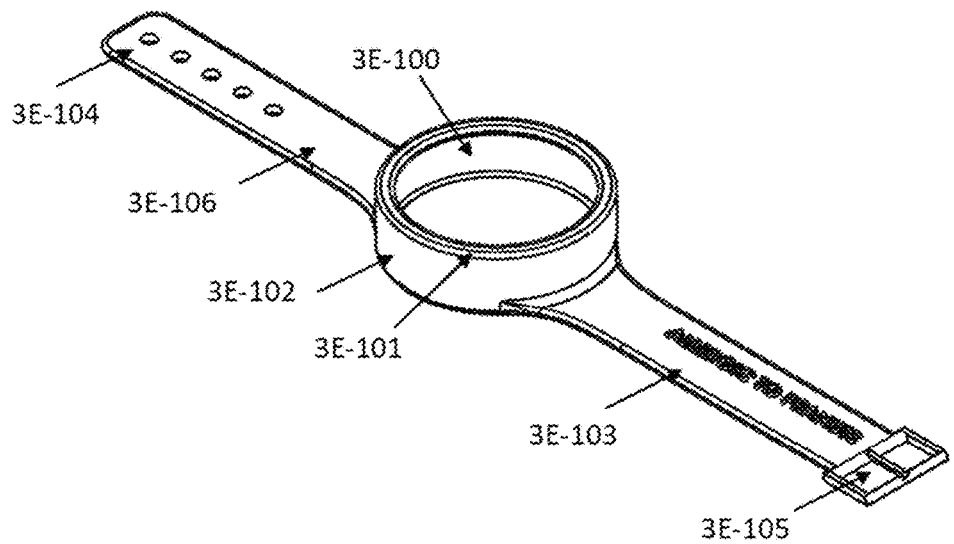
Figure 114:
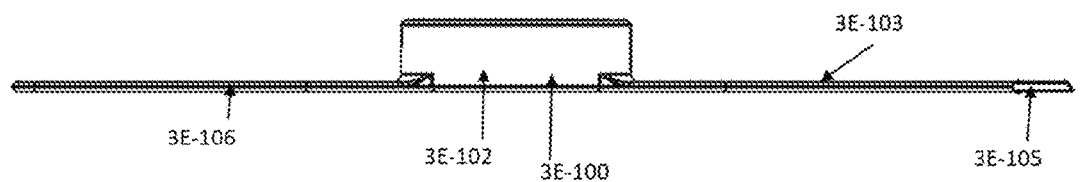
Figure 115:
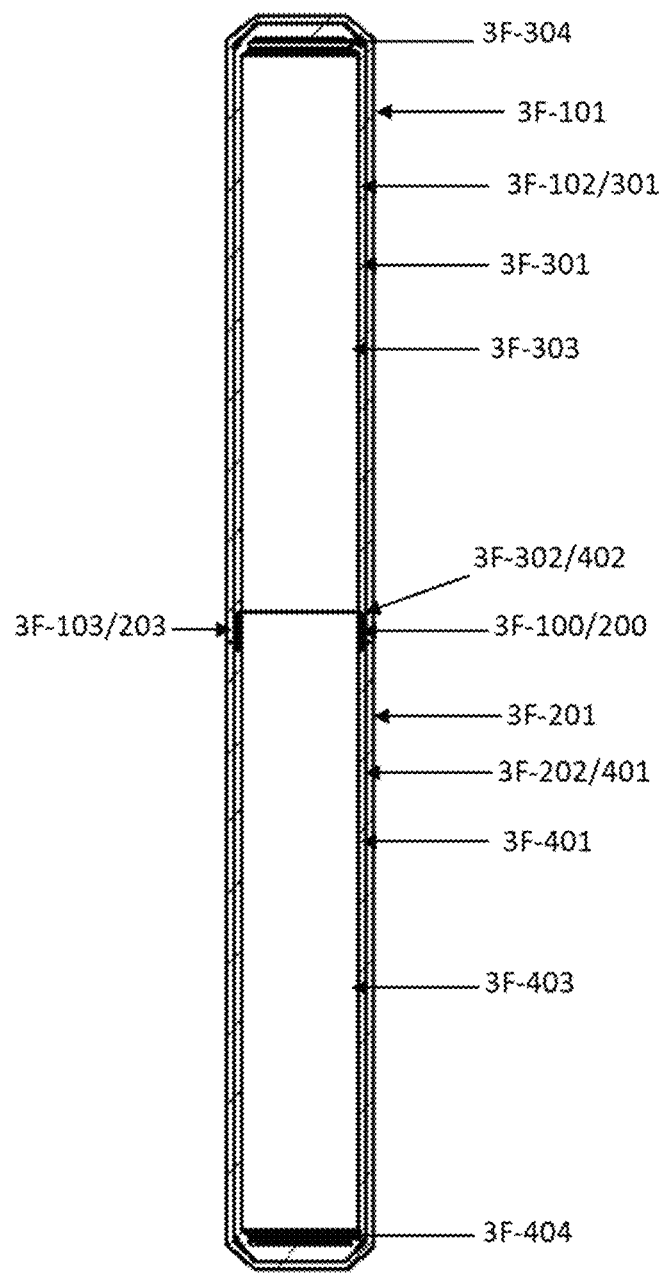
Figure 116:
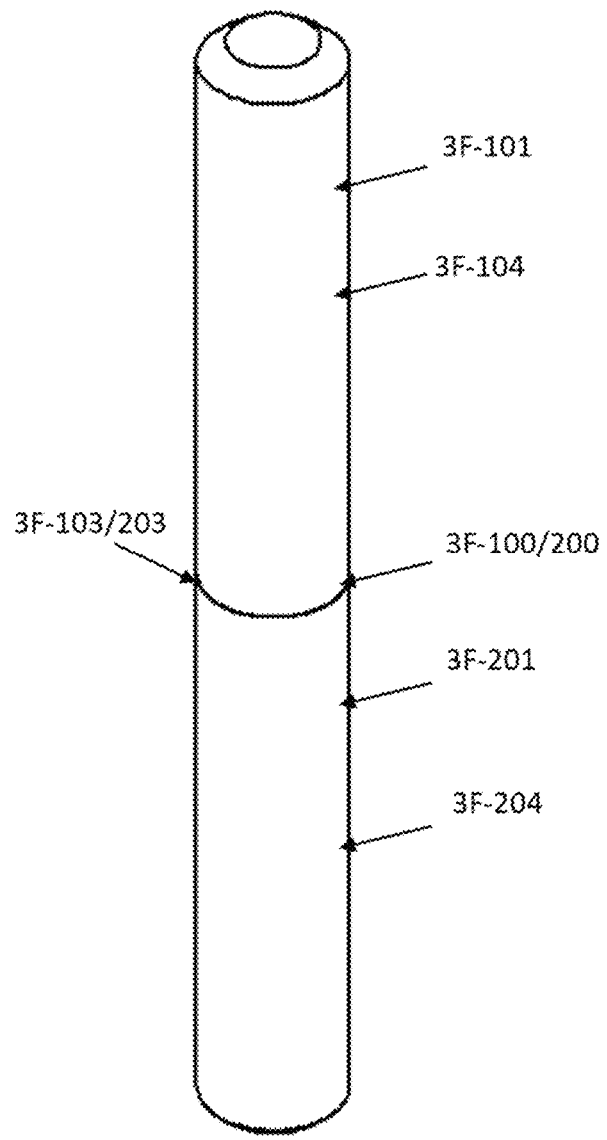
Figure 117:
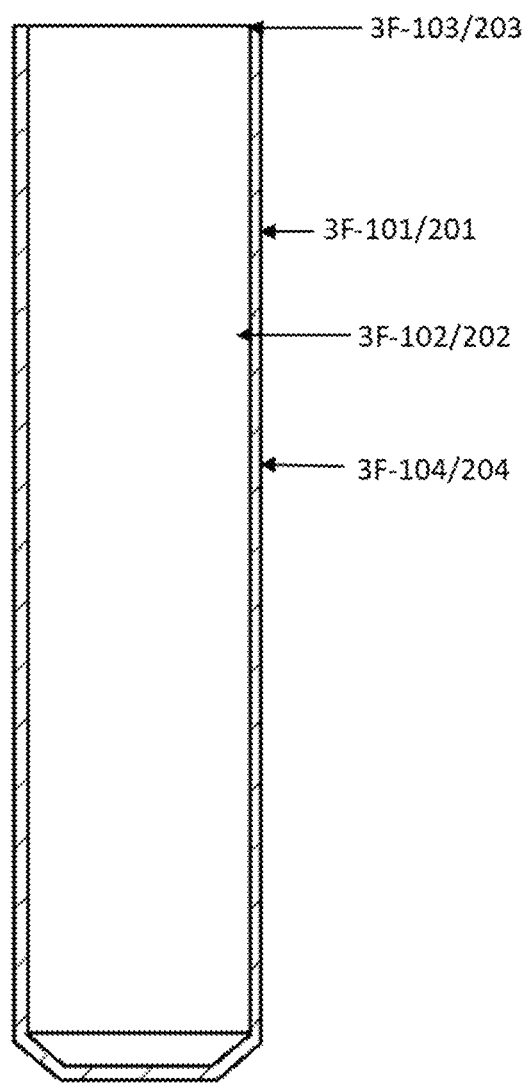
Figure 118:
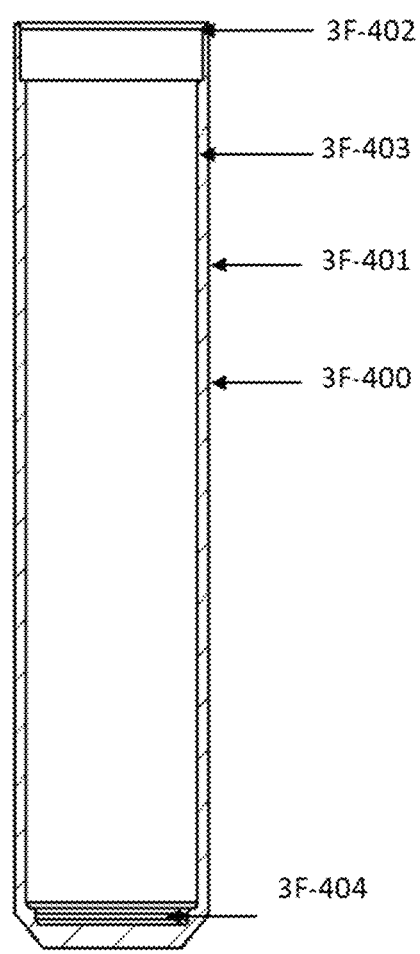
Figure 119:
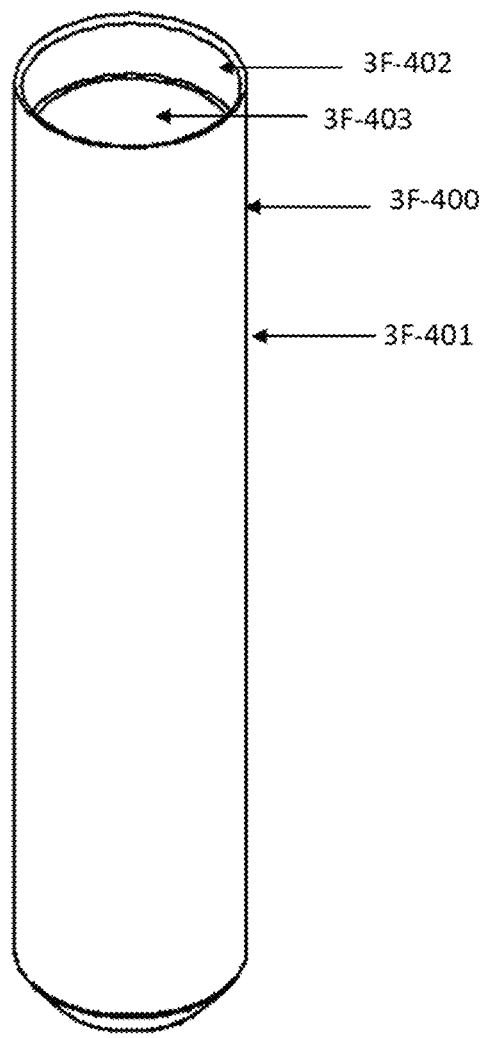
Figure 120:
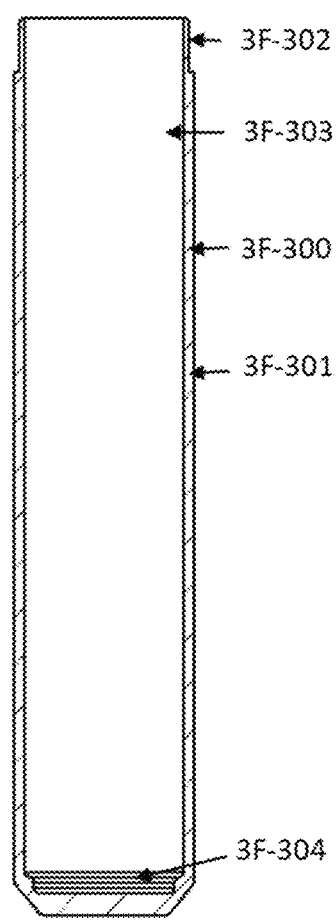
Figure 121:
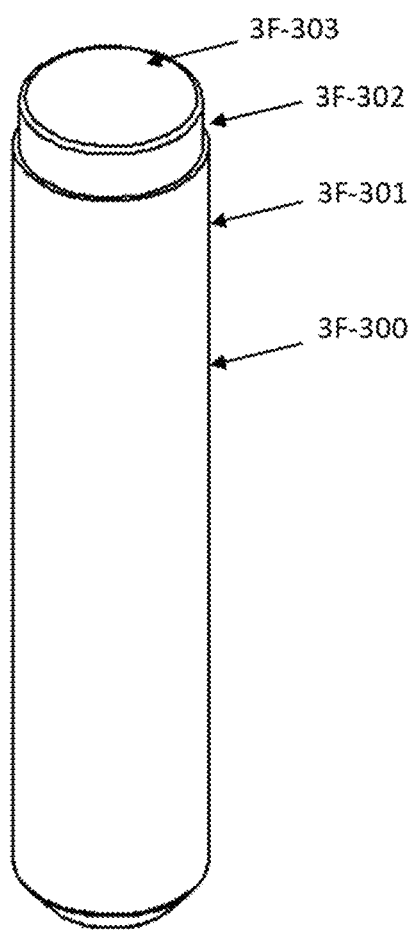
Figure 122:
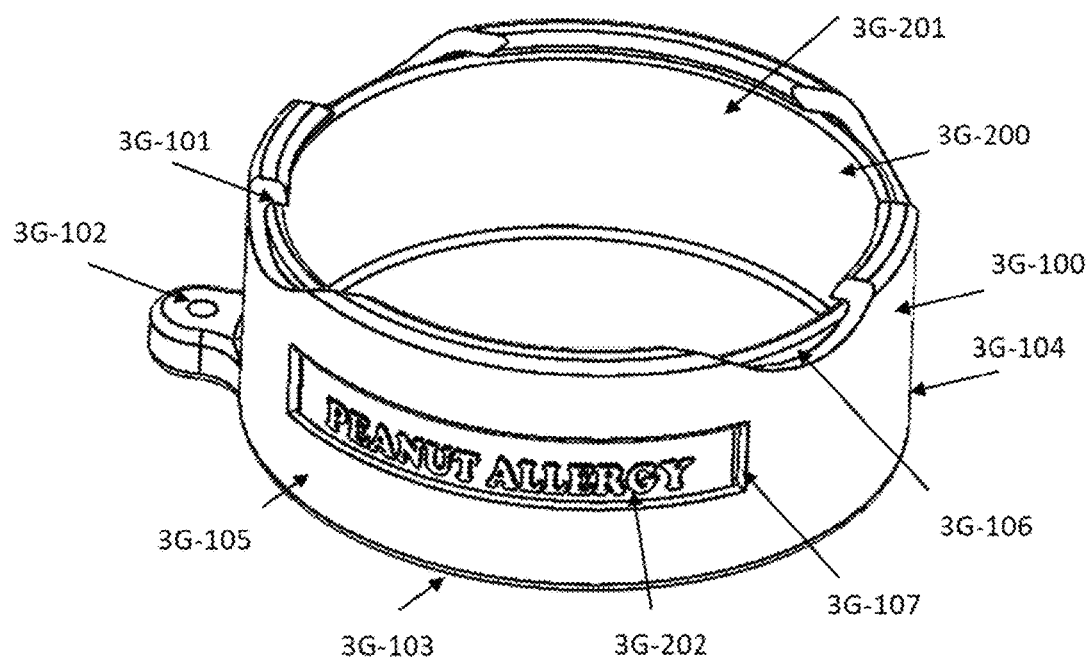
Figure 123:
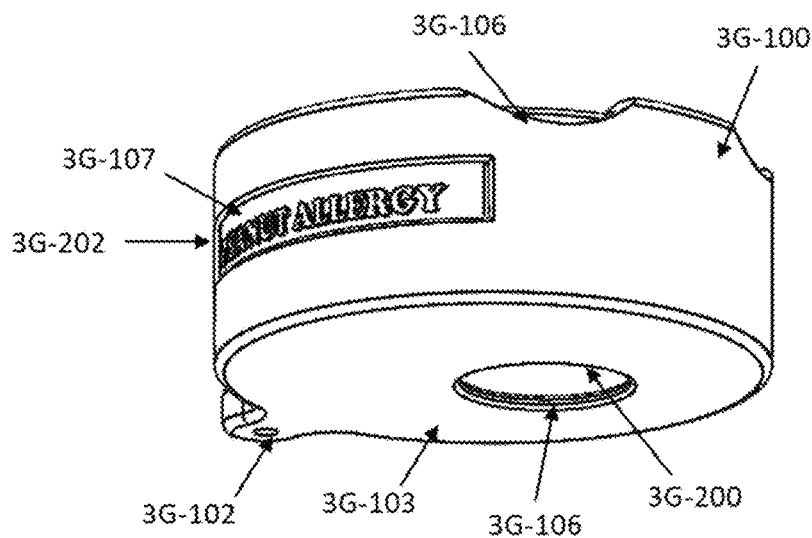
Figure 124:
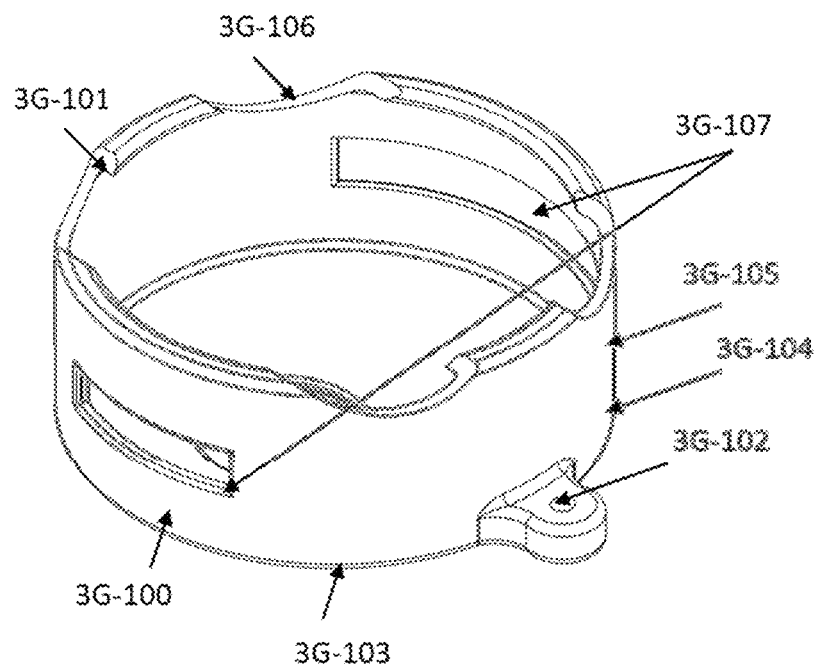
Figure 125:
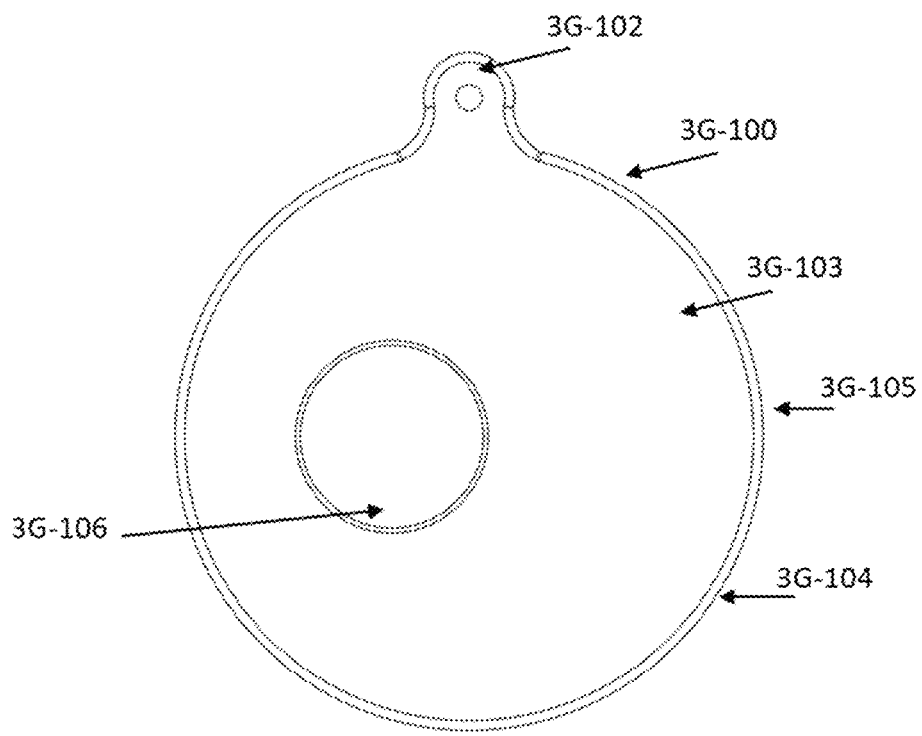
Figure 126:
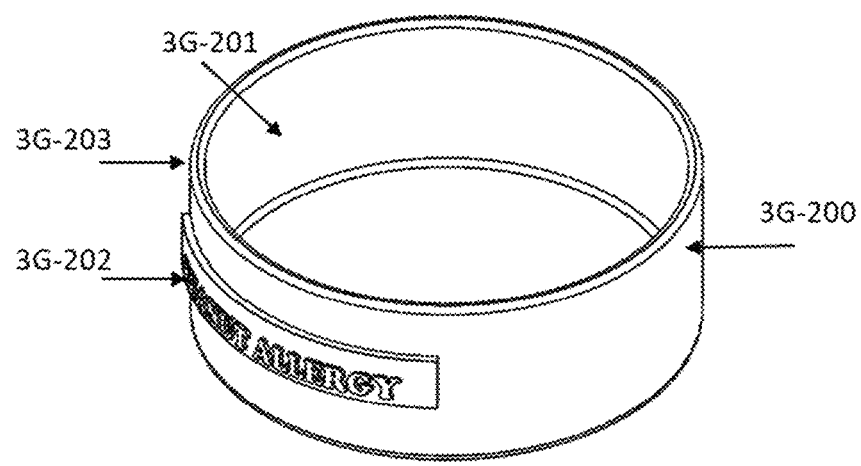
Figure 127:
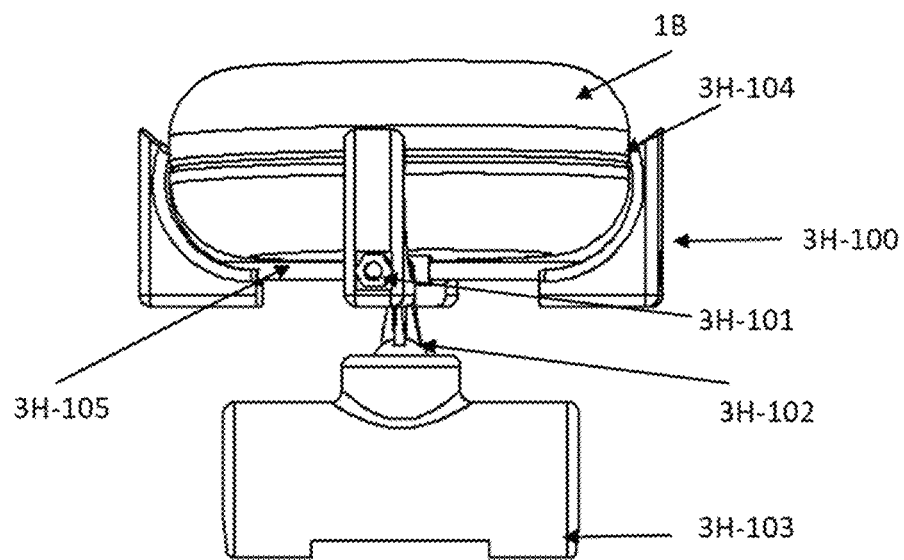
FIGS. 127-132 are schematic views of a non-vacuum sealed protective case for carrying a high aspect ratio auto-injector and for carrying a low aspect ratio auto-injector, that can pair with another protective case or be a stand-alone protective case, according to example embodiments.
Figure 128:
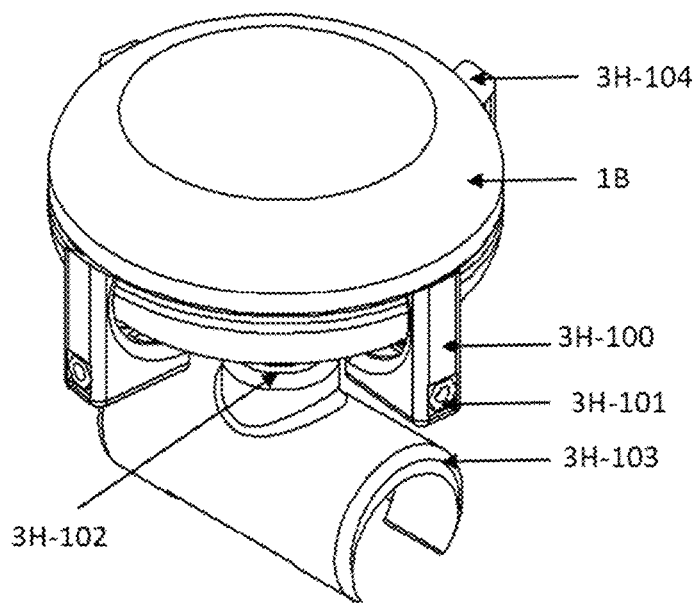
Figure 129:
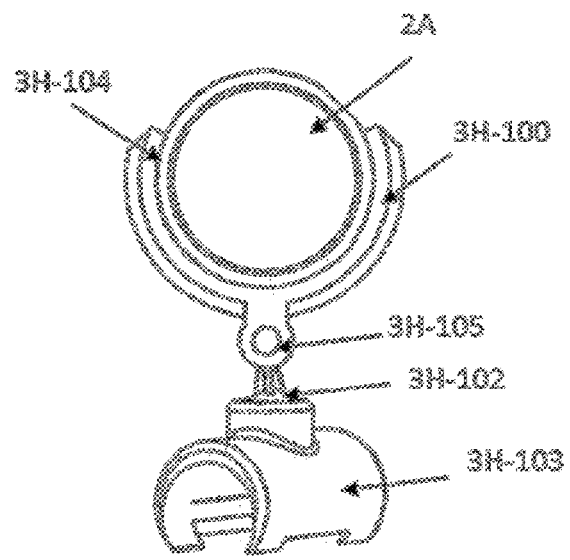
Figure 130:
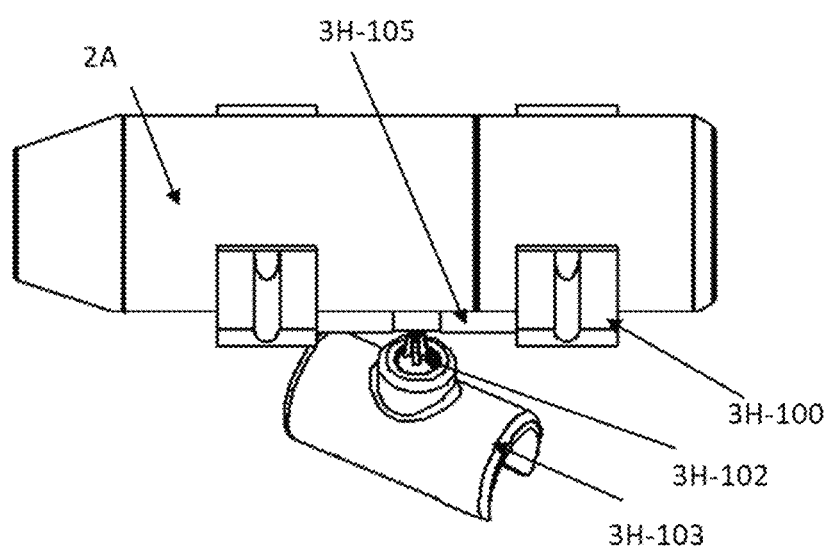
Figure 131:
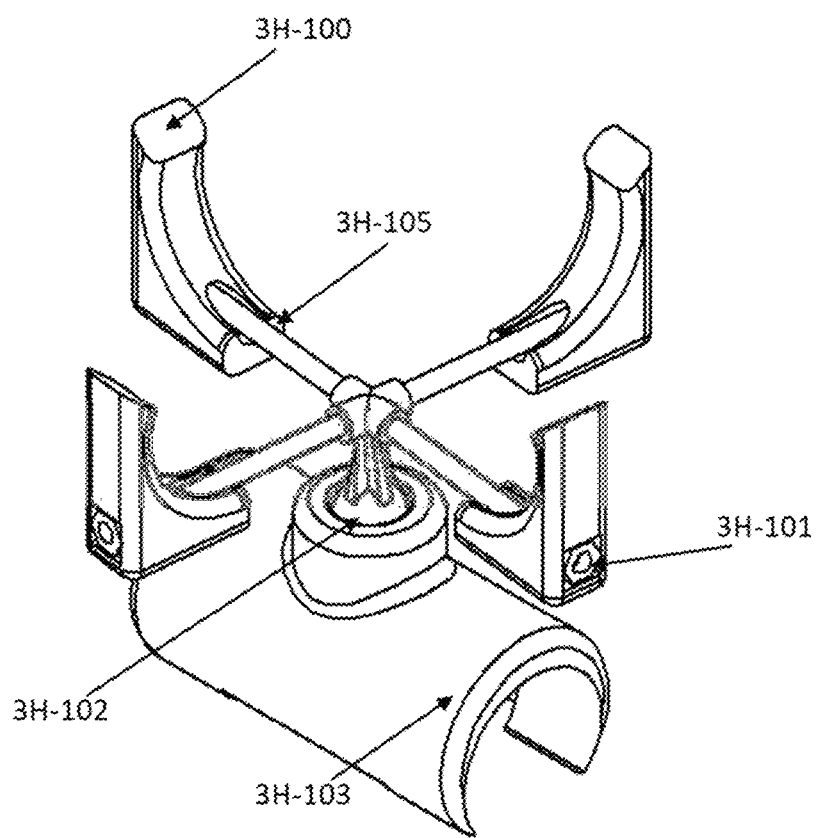
Figure 132:
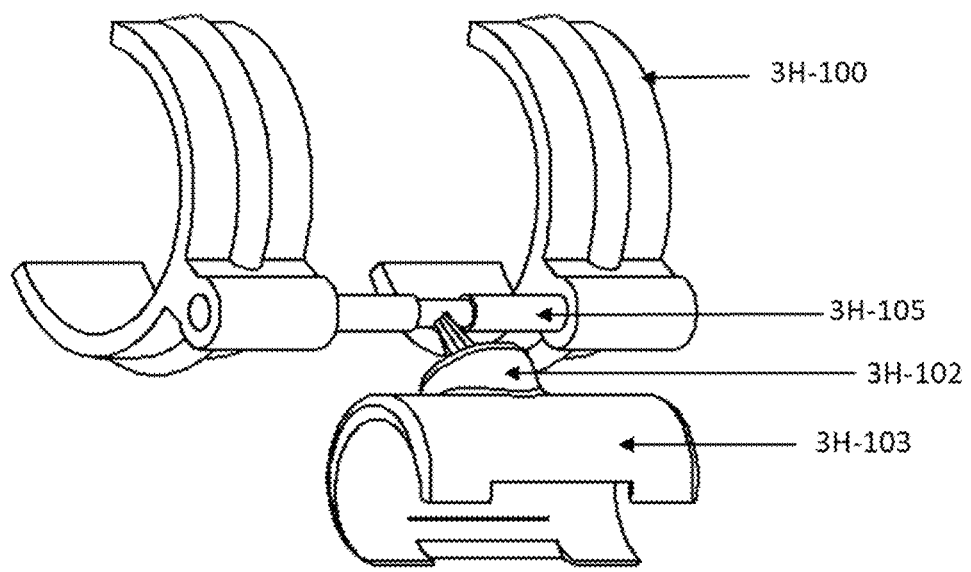

Embodiments of a protective case may not be required to possess thermally insulating properties (3A, 3B, 3C, 3D, 3E, 3F, 3G, 3H), but rather provide physical protection and a means of increased portability for an auto-injector. The protective case may form a cavity (3A-100, 3B-100, 3B-101, 3C-100, 3D-100, 3E-100, 3F-303, 3F-403, 3G-201, 3H-100) that releasably receives at least a portion of the auto-injector device. Embodiments shown in FIGS. 98-132 include but are not limited to different cases which may attach (3A-102, 3B-103, 3C-101, 3C-103, 3D-101, 3D-103, 3E-104, 3E-105, 3E-106, 3G-102, 3H-103) to everyday objects and allow for the auto-injector to be in close proximity to the user wherever they are. The protective cases may provide a manner of protection by damping any incurred forces or vibrations through material selections. Embodiments of a non-vacuum sealed case may be constructed of a metal, TP, TPE, fiber reinforced composite, ceramic, or combinations of similar materials. Certain embodiments may also provide a watertight/water-resistant or water-repellant enclosure (3F-101, 3F-201) around the device and may facilitate this watertight/water-resistant seal by means of a gasket or through the addition of a coating or separate material applied at the joint interface.

Certain embodiments of a protective case may provide a means of attaching the case to common everyday objects or similarly other protective cases (3A-102, 3B-103, 3C-101, 3C-103, 3D-101, 3D-103, 3E-104, 3E-105, 3E-106, 3G-102, 3H-103). The attachment mechanisms may include but are not limited to; a strap (3E-106), a clip, a pin, a clamp, a mount (3H-103), a tab forming an eyelet (3A-102, 3B-103, 3G-102), an adhesive layer (3A-103, 3G-103), and/or combinations thereof. One embodiment for the case may contain an eyelet (3A-102, 3B-103, 3G-102) or similar geometry to provide a means of fastening the case to another object. The eyelet (3A-102, 3B-103, 3G-102) or similar feature may be formed through a molded, adhered, or formed feature on the protective case. Alternatively, the case may provide a molded or formed strap (3E-106) or a similar feature. The strap (3E-106) may provide a means of adjustment to accommodate a desired circumference. This may be accomplished by of adjustment holes (3E-104), the adjustment holes may be fixed by means of a buckle (3E-105) or similar manner to fasten the case. In addition, the protective case for the auto-injector may have an adhesive (3A-103, 3G-103) applied to one surface for fixating the case to another object. Furthermore, one embodiment of the protective case for containing an auto-injector may allow for the integration of a cell phone, or similar electronic device, for better adaptation and meshing with the user's daily routine (ex: 3C-101, 3C-103, 3D-101, 3D-103) Further embodiments may be adapted to store one or more devices (3B-101, 3D-100). The case may hold a single device or multiple devices whether similar form or not. The configuration of holding multiple devices is not limited to a horizontal or vertical layout, but the best optimized method of storing the devices while maintaining as low a profile case as possible.

Embodiments of the protective case may contain a housing which receives the auto-injector (3A-100, 3B-100, 3B-101, 3C-100, 3D-100, 3E-100, 3F-303, 3F-403, 3G-201, 3H-100) and may stabilize the auto-injector by means of a feature molded or formed into the housing (ex: a ridge, lip, etc.) (3A-101, 3B-102, 3C-102, 3D-102, 3E-101, 3G-101, 3H-100). The ridge maintains constant communication between the device and the housing at all times until removed for use. Furthermore, the geometry of the housing may be such that once the device is disposed within, the housing is placed under a state of stress and as such maintains constant communication with the device (3C-104). The housing may or may not enclose all sides of the auto-injector (3A-106, 3B-106, 3C-106, 3D-104, 3E-102, 3F-303, 3F-403, 3G-201, 3H-100) whilst providing a means to easily and rapidly remove in times of need (3G-106). In addition, the ridge, lip, etc. (3H-104). of the housing ensures that any external vibrations will not allow the auto-injector to become separated from the housing (3A-100, 3B-100, 3B-101, 3C-100, 3D-100, 3E-100, 3F-303, 3F-403, 3G-201, 3H-100). One embodiment (3G) may contain multiple materials to provide a layering effect to protect and conceal the device. In certain embodiments the housing may provide a means of orienting the device during storage using molded or formed shoulders or other similar features. In certain embodiments the housing may also be adjustable to accommodate different sized auto-injectors (3H).

Certain embodiments may provide a textured or contoured exterior surface (3A-105, 3B-105, 3C-105, 3D-105, 3E-103, 3F-104, 3F-204, 3G-202, 3G-105) by means of a coating or applying additional materials, or molded features, or a combination of such. In some embodiments the external coating or textured surface may be accomplished by layering materials (3G). The exterior surface texture or contours may aid in increasing the ergonomics or handling of the case, or likewise in assisting the user in removing the auto-injector (3G-106). Furthermore, this exterior coating or layer(s) of dissimilar material or combination of such may perform the following functionalities; increase the ergonomics of the case, aid in reducing the induced vibrations from external loading, assisting in case aesthetics, provide structural support, provide labeling (3G-302), etc.

Furthermore, these cases may provide a means to be able to accommodate the auto-injector alone or incorporate other protective cases in combination as well (vacuum sealed or not) (3H-100, 3H-101, 3H-104, 3H-105). Embodiments of certain protective cases may present themselves with a feature to allow for the mounting and joining to other cases. Adjustments for securing various sized auto-injectors and cases may be accomplished through, but not limited to, clips, straps (3E-106), molded features (33-106, 3H-103), or other suitable means which can securely fasten one to the other.

Additional, embodiments of the case may provide a way of moving the auto-injector relative to the point of fixation (3H-103). This relative movement may be facilitated by but not limited to a ball joint and receiver (3H-102). The ability to move the auto-injector relative to the fixation point may allow the user better access, and improved ergonomics for handling and accessibility.

Certain embodiments of the case may provide a power source to assist in monitoring the conditions of the case both internal and external as well as the connectivity of the case with other smart devices. The case may provide the user with an interface for monitoring internal and external conditions to better maintain the enclosed device.

The table below provides names and brief descriptions of the references numerals appearing in the figures:

| REFERENCE NUMERAL | NAME | DESCRIPTION |
|---|---|---|
| 1A | VACUUM CASE (W/EXTERNAL GRIP SURFACE) | COMPLETE PART |
| 1A-100 | TOP GRIP SURFACE | COMPLETE PART |
| 1A-101 | TOP GRIP SURFACE | USER INTERFACE (FINGER SCALLOPS) |
| 1A-102 | TOP GRIP SURFACE | LABEL (EMBOSSED WRITING) |
| 1A-103 | TOP GRIP SURFACE | SEALING EDGE |
| 1A-104 | TOP GRIP SURFACE | EXTERNAL ATTACHMENT MECHANISM |
| 1A-200 | BOTTOM GRIP SURFACE | COMPLETE PART |
| 1A-201 | BOTTOM GRIP SURFACE | USER INTERFACE (FINGER SCALLOPS) |
| 1A-202 | BOTTOM GRIP SURFACE | IOT INTERFACE AND POWER SOURCE HOUSING/CAVITY |
| 1A-203 | BOTTOM GRIP SURFACE | SEALING EDGE |
| 1A-300 | BOTTOM HALF OF ENCLOSURE/CASE | COMPLETE PART |
| 1A-301 | BOTTOM HALF OF ENCLOSURE/CASE | SEALED VACUUM CHAMBER |
| 1A-302 | BOTTOM HALF OF ENCLOSURE/CASE | THREADED CONNECTION |
| 1A-303 | BOTTOM HALF OF ENCLOSURE/CASE | WATER-RESISTANT COATING ON SEALING INTERFACE |
| 1A-304 | BOTTOM HALF OF ENCLOSURE/CASE | SCALLOPS FOR DEVICE REMOVAL |
| 1A-305 | BOTTOM HALF OF ENCLOSURE/CASE | RIGID HOUSING FOR FORMING THE VACUUM CHAMBER |
| 1A-306 | BOTTOM HALF OF ENCLOSURE/CASE | INTERFACE BETWEEN INSULATION BARRIER AND BOTTOM HOUSING |
| 1A-307 | BOTTOM HALF OF ENCLOSURE/CASE | SEALING EDGE |
| 1A-308 | BOTTOM HALF OF ENCLOSURE/CASE | POLISHED SURFACE OR REFLECTIVE COATED SURFACE INSIDE VACUUM CHAMBER |
| 1A-400 | TOP HALF OF ENCLOSURE/CASE | COMPLETE PART |
| 1A-401 | TOP HALF OF ENCLOSURE/CASE | SEALED VACUUM CHAMBER |
| 1A-402 | TOP HALF OF ENCLOSURE/CASE | THREADED CONNECTION |
| 1A-403 | TOP HALF OF ENCLOSURE/CASE | WATER-RESISTANT COATING ON SEALING INTERFACE |
| 1A-404 | TOP HALF OF ENCLOSURE/CASE | RIGID HOUSING FOR FORMING THE VACUUM CHAMBER |
| 1A-405 | TOP HALF OF ENCLOSURE/CASE | INTERFACE BETWEEN INSULATION BARRIER AND TOP HOUSING |
| 1A-406 | TOP HALF OF ENCLOSURE/CASE | SEALING EDGE |
| 1A-407 | TOP HALF OF ENCLOSURE/CASE | POLISHED SURFACE OR REFLECTIVE COATED SURFACE INSIDE VACUUM CHAMBER |
| 1A-500 | TOP INSULATION BARRIER | COMPLETE PART |
| 1A-501 | TOP INSULATION BARRIER | INTERFACE BETWEEN INSULATION BARRIER AND TOP HOUSING |
| 1A-502 | TOP INSULATION BARRIER | STABILIZING SHOULDER FOR FIXING DEVICE |
| 1A-503 | TOP INSULATION BARRIER | SEALING INTERFACE WITH COORESPONDING INSULATION BARRIER |
| 1A-600 | BOTTOM INSULATION BARRIER | COMPLETE PART |
| 1A-601 | BOTTOM INSULATION BARRIER | INTERFACE BETWEEN INSULATION BARRIER AND BOTTOM HOUSING |
| 1A-602 | BOTTOM INSULATION BARRIER | STABILIZING SHOULDER FOR FIXING DEVICE |
| 1A-603 | BOTTOM INSULATION BARRIER | SEALING INTERFACE WITH COORESPONDING INSULATION BARRIER |
| 1A-700 | ELECTRONIC DISPLAY & POWER SOURCE | DISPLAY SCREEN AND USER INTERFACE |
| 1A-701 | ELECTRONIC DISPLAY & POWER SOURCE | POWER SOURCE |
| 1B | VACUUM CASE (WITH GASKET & THREADS ON INSULATION BARRIER) | COMPLETE PART |
| 1B-100 | TOP HALF OF ENCLOSURE/CASE | COMPLETE PART |
| 1B-101 | TOP HALF OF ENCLOSURE/CASE | SEALED VACUUM CHAMBER |
| 1B-102 | TOP HALF OF ENCLOSURE/CASE | THREADED CONNECTION |
| 1B-103 | TOP HALF OF ENCLOSURE/CASE | RIGID HOUSING FOR FORMING THE VACUUM CHAMBER |
| 1B-104 | TOP HALF OF ENCLOSURE/CASE | INTERFACE BETWEEN INSULATION BARRIER AND TOP HOUSING |
| 1B-105 | TOP HALF OF ENCLOSURE/CASE | SEALING EDGE |
| 1B-106 | TOP HALF OF ENCLOSURE/CASE | EXTERIOR TEXTURED OR COATED SURFACE |
| 1B-107 | TOP HALF OF ENCLOSURE/CASE | POLISHED SURFACE OR REFLECTIVE COATED SURFACE INSIDE VACUUM CHAMBER |

-continued

| REFERENCE NUMERAL | NAME | DESCRIPTION |
|---|---|---|
| 1B-200 | BOTTOM HALF OF ENCLOSURE/CASE | COMPLETE PART |
| 1B-201 | BOTTOM HALF OF ENCLOSURE/CASE | SEALED VACUUM CHAMBER |
| 1B-202 | BOTTOM HALF OF ENCLOSURE/CASE | RIGID HOUSING FOR FORMING THE VACUUM CHAMBER |
| 1B-203 | BOTTOM HALF OF ENCLOSURE/CASE | INTERFACE BETWEEN INSULATION BARRIER AND BOTTOM HOUSING |
| 1B-204 | BOTTOM HALF OF ENCLOSURE/CASE | SEALING EDGE |
| 1B-205 | BOTTOM HALF OF ENCLOSURE/CASE | EXTERIOR TEXTURED OR COATED SURFACE |
| 1B-206 | BOTTOM HALF OF ENCLOSURE/CASE | POLISHED SURFACE OR REFLECTIVE COATED SURFACE INSIDE VACUUM CHAMBER |
| 1B-300 | GASKET FOR WATERTIGHT/WATER-RESISTANT SEAL | COMPLETE PART |
| 1B-400 | TOP INSULATION BARRIER | COMPLETE PART |
| 1B-401 | TOP INSULATION BARRIER | INTERFACE BETWEEN INSULATION BARRIER AND TOP HOUSING |
| 1B-402 | TOP INSULATION BARRIER | SEALING INTERFACE WITH COORESPONDING INSULATION BARRIER |
| 1B-403 | TOP INSULATION BARRIER | DEVICE CONTACT SURFACE |
| 1B-500 | BOTTOM INSULATION BARRIER | COMPLETE PART |
| 1B-501 | BOTTOM INSULATION BARRIER | INTERFACE BETWEEN INSULATION BARRIER AND BOTTOM HOUSING |
| 1B-502 | BOTTOM INSULATION BARRIER | SEALING INTERFACE WITH COORESPONDING INSULATION BARRIER |
| 1B-503 | BOTTOM INSULATION BARRIER | THREADED CONNECTION |
| 1B-504 | BOTTOM INSULATION BARRIER | SCALLOPS FOR DEVICE REMOVAL |
| 1B-505 | BOTTOM INSULATION BARRIER | DEVICE CONTACT SURFACE |
| 1C | VACUUM CASE (W/SEPARATE DAMPING COMPONENT FOR DEVICE CRADLE) | COMPLETE PART |
| 1C-100 | TOP HALF OF ENCLOSURE/CASE | COMPLETE PART |
| 1C-101 | TOP HALF OF ENCLOSURE/CASE | SEALED VACUUM CHAMBER |
| 1C-102 | TOP HALF OF ENCLOSURE/CASE | FRICTION/INTERFERENCE CONNECTION FOR BOTTOM HALF OF ENCLOSURE/CASE |
| 1C-103 | TOP HALF OF ENCLOSURE/CASE | RIGID HOUSING #1 FOR FORMING THE VACUUM CHAMBER |
| 1C-104 | TOP HALF OF ENCLOSURE/CASE | RIGID HOUSING #2 FOR FORMING THE VACUUM CHAMBER |
| 1C-105 | TOP HALF OF ENCLOSURE/CASE | INTERFACE BETWEEN INSULATION BARRIER/STABILIZER AND TOP HOUSING |
| 1C-106 | TOP HALF OF ENCLOSURE/CASE | SEALING EDGE |
| 1C-107 | TOP HALF OF ENCLOSURE/CASE | EXTERIOR TEXTURED OR COATED SURFACE |
| 1C-108 | TOP HALF OF ENCLOSURE/CASE | POLISHED SURFACE OR REFLECTIVE COATED SURFACE INSIDE VACUUM CHAMBER |
| 1C-200 | BOTTOM HALF OF ENCLOSURE/CASE | COMPLETE PART |
| 1C-201 | BOTTOM HALF OF ENCLOSURE/CASE | SEALED VACUUM CHAMBER |
| 1C-202 | BOTTOM HALF OF ENCLOSURE/CASE | FRICTION/INTERFERENCE CONNECTION FOR TOP HALF OF ENCLOSURE/CASE |
| 1C-203 | BOTTOM HALF OF ENCLOSURE/CASE | RIGID HOUSING #1 FOR FORMING THE VACUUM CHAMBER |
| 1C-204 | BOTTOM HALF OF ENCLOSURE/CASE | RIGID HOUSING #2 FOR FORMING THE VACUUM CHAMBER |
| 1C-205 | BOTTOM HALF OF ENCLOSURE/CASE | INTERFACE BETWEEN INSULATION BARRIER/STABILIZER AND BOTTOM HOUSING |
| 1C-206 | BOTTOM HALF OF ENCLOSURE/CASE | SEALING EDGE |
| 1C-207 | BOTTOM HALF OF ENCLOSURE/CASE | EXTERIOR TEXTURED OR COATED SURFACE |
| 1C-208 | BOTTOM HALF OF ENCLOSURE/CASE | POLISHED SURFACE OR REFLECTIVE COATED SURFACE INSIDE VACUUM CHAMBER |
| 1C-300 | TOP INSULATION BARRIER | COMPLETE PART |
| 1C-301 | TOP INSULATION BARRIER | INTERFACE BETWEEN INSULATION BARRIER AND TOP HOUSING |
| 1C-302 | TOP INSULATION BARRIER | SEALING INTERFACE WITH COORESPONDING INSULATION BARRIER |

-continued

| REFERENCE NUMERAL | NAME | DESCRIPTION |
| --- | --- | --- |
| 1C-400 | BOTTOM INSULATION BARRIER | COMPLETE PART |
| 1C-401 | BOTTOM INSULATION BARRIER | INTERFACE BETWEEN INSULATION BARRIER AND BOTTOM HOUSING |
| 1C-402 | BOTTOM INSULATION BARRIER | SEALING INTERFACE WITH COORESPONDING INSULATION BARRIER |
| 1C-500 | STABILIZATION/SHOCK ABSORBING COMPONENT | COMPLETE PART |
| 1C-501 | STABILIZATION/SHOCK ABSORBING COMPONENT | INTERFACE WITH INSULATION BARRIER |
| 1C-502 | STABILIZATION/SHOCK ABSORBING COMPONENT | INTERFACE WITH SURFACE OF UPPER/LOWER HALF OF ENCLOSURE/CASE |
| 1C-503 | STABILIZATION/SHOCK ABSORBING COMPONENT | DEVICE CRADDLE |
| 1D | VACUUM CASE (INSULATION BARRIER PROVIDES USER WITH INTERFACE) | COMPLETE PART |
| 1D-100 | TOP HALF OF ENCLOSURE/CASE | COMPLETE PART |
| 1D-101 | TOP HALF OF ENCLOSURE/CASE | SEALED VACUUM CHAMBER |
| 1D-102 | TOP HALF OF ENCLOSURE/CASE | RIGID HOUSING FOR FORMING THE VACUUM CHAMBER |
| 1D-103 | TOP HALF OF ENCLOSURE/CASE | INTERFACE BETWEEN INSULATION BARRIER AND TOP HOUSING |
| 1D-104 | TOP HALF OF ENCLOSURE/CASE | EXTERIOR TEXTURED OR COATED SURFACE |
| 1D-105 | TOP HALF OF ENCLOSURE/CASE | POLISHED SURFACE OR REFLECTIVE COATED SURFACE INSIDE VACUUM CHAMBER |
| 1D-200 | BOTTOM HALF OF ENCLOSURE/CASE | COMPLETE PART |
| 1D-201 | BOTTOM HALF OF ENCLOSURE/CASE | SEALED VACUUM CHAMBER |
| 1D-202 | BOTTOM HALF OF ENCLOSURE/CASE | RIGID HOUSING FOR FORMING THE VACUUM CHAMBER |
| 1D-203 | BOTTOM HALF OF ENCLOSURE/CASE | INTERFACE BETWEEN INSULATION BARRIER AND BOTTOM HOUSING |
| 1D-204 | BOTTOM HALF OF ENCLOSURE/CASE | EXTERIOR TEXTURED OR COATED SURFACE |
| 1D-205 | BOTTOM HALF OF ENCLOSURE/CASE | POLISHED SURFACE OR REFLECTIVE COATED SURFACE INSIDE VACUUM CHAMBER |
| 1D-300 | TOP INSULATION BARRIER | COMPLETE PART |
| 1D-301 | TOP INSULATION BARRIER | INTERFACE BETWEEN INSULATION BARRIER AND TOP HOUSING |
| 1D-302 | TOP INSULATION BARRIER | SEALING INTERFACE WITH COORESPONDING INSULATION BARRIER |
| 1D-303 | TOP INSULATION BARRIER | AUTO-INJECTOR CONTACT SURFACE |
| 1D-304 | TOP INSULATION BARRIER | EXTERIOR USER INTERFACE |
| 1D-400 | BOTTOM INSULATION BARRIER | COMPLETE PART |
| 1D-401 | BOTTOM INSULATION BARRIER | INTERFACE BETWEEN INSULATION BARRIER AND BOTTOM HOUSING |
| 1D-402 | BOTTOM INSULATION BARRIER | SEALING INTERFACE WITH COORESPONDING INSULATION BARRIER |
| 1D-403 | BOTTOM INSULATION BARRIER | AUTO-INJECTOR CONTACT SURFACE |
| 1D-404 | BOTTOM INSULATION BARRIER | EXTERIOR USER INTERFACE |
| 1E | VACUUM CASE (FOR HOLDING MULTIPLE AUTO-INJECTORS) | COMPLETE PART |
| IE-100 | TOP HALF OF ENCLOSURE/CASE | COMPLETE PART |
| IE-101 | TOP HALF OF ENCLOSURE/CASE | SEALED VACUUM CHAMBER |
| IE-102 | TOP HALF OF ENCLOSURE/CASE | RIGID HOUSING FOR FORMING THE VACUUM CHAMBER |
| IE-103 | TOP HALF OF ENCLOSURE/CASE | INTERFACE BETWEEN INSULATION BARRIER AND TOP HOUSING |
| IE-104 | TOP HALF OF ENCLOSURE/CASE | EXTERIOR TEXTURED OR COATED SURFACE |
| IE-105 | TOP HALF OF ENCLOSURE/CASE | POLISHED SURFACE OR REFLECTIVE COATED SURFACE INSIDE VACUUM CHAMBER |
| IE-106 | TOP HALF OF ENCLOSURE/CASE | FRICTION/INTERFERENCE CONNECTION FOR BOTTOM HALF OF ENCLOSURE/CASE |
| IE-200 | BOTTOM HALF OF ENCLOSURE/CASE | COMPLETE PART |
| IE-201 | BOTTOM HALF OF ENCLOSURE/CASE | SEALED VACUUM CHAMBER |
| IE-202 | BOTTOM HALF OF ENCLOSURE/CASE | RIGID HOUSING FOR FORMING THE VACUUM CHAMBER |

-continued

| REFERENCE NUMERAL | NAME | DESCRIPTION |
|---|---|---|
| IE-203 | BOTTOM HALF OF ENCLOSURE/CASE | INTERFACE BETWEEN INSULATION BARRIER AND BOTTOM HOUSING |
| IE-204 | BOTTOM HALF OF ENCLOSURE/CASE | EXTERIOR TEXTURED OR COATED SURFACE |
| IE-205 | BOTTOM HALF OF ENCLOSURE/CASE | POLISHED SURFACE OR REFLECTIVE COATED SURFACE INSIDE VACUUM CHAMBER |
| IE-206 | BOTTOM HALF OF ENCLOSURE/CASE | FRICTION/INTERFERENCE CONNECTION FOR BOTTOM HALF OF ENCLOSURE/CASE |
| IE-300 | TOP INSULATION BARRIER | COMPLETE PART |
| IE-301 | TOP INSULATION BARRIER | INTERFACE BETWEEN INSULATION BARRIER AND TOP HOUSING |
| IE-302 | TOP INSULATION BARRIER | SEALING INTERFACE WITH COORESPONDING INSULATION BARRIER |
| IE-303 | TOP INSULATION BARRIER | AUTO-INJECTOR CONTACT SURFACE |
| IE-304 | TOP INSULATION BARRIER | SCALLOPS FOR DEVICE REMOVAL |
| IE-400 | BOTTOM INSULATION BARRIER | COMPLETE PART |
| IE-401 | BOTTOM INSULATION BARRIER | INTERFACE BETWEEN INSULATION BARRIER AND BOTTOM HOUSING |
| IE-402 | BOTTOM INSULATION BARRIER | SEALING INTERFACE WITH COORESPONDING INSULATION BARRIER |
| IE-403 | BOTTOM INSULATION BARRIER | AUTO-INJECTOR CONTACT SURFACE |
| IE-404 | BOTTOM INSULATION BARRIER | SCALLOPS FOR DEVICE REMOVAL |
| 2A | VACUUM CASE (AUTO-INJECTORS W/ PEN FORM FACTOR) | COMPLETE PART |
| 2A-100 | TOP HALF OF ENCLOSURE/CASE | COMPLETE PART |
| 2A-101 | TOP HALF OF ENCLOSURE/CASE | SEALED VACUUM CHAMBER |
| 2A-102 | TOP HALF OF ENCLOSURE/CASE | FRICTION/INTERFERENCE CONNECTION FOR BOTTOM HALF OF ENCLOSURE/CASE |
| 2A-103 | TOP HALF OF ENCLOSURE/CASE | RIGID HOUSING #1 FOR FORMING THE VACUUM CHAMBER |
| 2A-104 | TOP HALF OF ENCLOSURE/CASE | RIGID HOUSING #2 FOR FORMING THE VACUUM CHAMBER |
| 2A-105 | TOP HALF OF ENCLOSURE/CASE | INTERFACE BETWEEN INSULATION BARRIER AND TOP HOUSING |
| 2A-106 | TOP HALF OF ENCLOSURE/CASE | SEALING EDGE |
| 2A-107 | TOP HALF OF ENCLOSURE/CASE | EXTERIOR TEXTURED OR COATED SURFACE |
| 2A-108 | TOP HALF OF ENCLOSURE/CASE | POLISHED SURFACE OR REFLECTIVE COATED SURFACE INSIDE VACUUM CHAMBER |
| 2A-200 | BOTTOM HALF OF ENCLOSURE/CASE | COMPLETE PART |
| 2A-201 | BOTTOM HALF OF ENCLOSURE/CASE | SEALED VACUUM CHAMBER |
| 2A-202 | BOTTOM HALF OF ENCLOSURE/CASE | FRICTION/INTERFERENCE CONNECTION FOR BOTTOM HALF OF ENCLOSURE/CASE |
| 2A-203 | BOTTOM HALF OF ENCLOSURE/CASE | RIGID HOUSING #1 FOR FORMING THE VACUUM CHAMBER |
| 2A-204 | BOTTOM HALF OF ENCLOSURE/CASE | RIGID HOUSING #2 FOR FORMING THE VACUUM CHAMBER |
| 2A-205 | BOTTOM HALF OF ENCLOSURE/CASE | INTERFACE BETWEEN INSULATION BARRIER AND BOTTOM HOUSING |
| 2A-206 | BOTTOM HALF OF ENCLOSURE/CASE | SEALING EDGE |
| 2A-207 | BOTTOM HALF OF ENCLOSURE/CASE | EXTERIOR TEXTURED OR COATED SURFACE |
| 2A-208 | BOTTOM HALF OF ENCLOSURE/CASE | POLISHED SURFACE OR REFLECTIVE COATED SURFACE INSIDE VACUUM CHAMBER |
| 2A-300 | TOP INSULATION BARRIER | COMPLETE PART |
| 2A-301 | TOP INSULATION BARRIER | INTERFACE BETWEEN INSULATION BARRIER AND TOP HOUSING |
| 2A-302 | TOP INSULATION BARRIER | SEALING INTERFACE WITH COORESPONDING INSULATION BARRIER |
| 2A-303 | TOP INSULATION BARRIER | AUTO-INJECTOR CONTACT SURFACE |
| 2A-304 | TOP INSULATION BARRIER | AUTO-INJECTOR ORIENTATION CUT-OUT |
| 2A-400 | BOTTOM INSULATION BARRIER | COMPLETE PART |
| 2A-401 | BOTTOM INSULATION BARRIER | INTERFACE BETWEEN INSULATION BARRIER AND BOTTOM HOUSING |

-continued

| REFERENCE NUMERAL | NAME | DESCRIPTION |
|---|---|---|
| 2A-402 | BOTTOM INSULATION BARRIER | SEALING INTERFACE WITH COORESPONDING INSULATION BARRIER |
| 2A-403 | BOTTOM INSULATION BARRIER | AUTO-INJECTOR CONTACT SURFACE |
| 2A-404 | BOTTOM INSULATION BARRIER | AUTO-INJECTOR ORIENTATION CUT-OUT |
| 2B | VACUUM CASE (AUTO-INJECTORS W/ RECTANGULAR FORM FACTOR) | COMPLETE PART |
| 2B-100 | TOP HALF OF ENCLOSURE/CASE | COMPLETE PART |
| 2B-101 | TOP HALF OF ENCLOSURE/CASE | SEALED VACUUM CHAMBER |
| 2B-102 | TOP HALF OF ENCLOSURE/CASE | FRICTION/INTERFERENCE CONNECTION FOR BOTTOM HALF OF ENCLOSURE/CASE |
| 2B-103 | TOP HALF OF ENCLOSURE/CASE | RIGID HOUSING FOR FORMING THE VACUUM CHAMBER |
| 2B-104 | TOP HALF OF ENCLOSURE/CASE | INTERFACE BETWEEN INSULATION BARRIER AND BOTTOM HOUSING |
| 2B-105 | TOP HALF OF ENCLOSURE/CASE | SEALING EDGE |
| 2B-106 | TOP HALF OF ENCLOSURE/CASE | EXTERIOR TEXTURED OR COATED SURFACE |
| 2B-107 | TOP HALF OF ENCLOSURE/CASE | POLISHED SURFACE OR REFLECTIVE COATED SURFACE INSIDE VACUUM CHAMBER |
| 2B-200 | BOTTOM HALF OF ENCLOSURE/CASE | COMPLETE PART |
| 2B-201 | BOTTOM HALF OF ENCLOSURE/CASE | SEALED VACUUM CHAMBER |
| 2B-202 | BOTTOM HALF OF ENCLOSURE/CASE | FRICTION/INTERFERENCE CONNECTION FOR BOTTOM HALF OF ENCLOSURE/CASE |
| 2B-203 | BOTTOM HALF OF ENCLOSURE/CASE | RIGID HOUSING FOR FORMING THE VACUUM CHAMBER |
| 2B-204 | BOTTOM HALF OF ENCLOSURE/CASE | INTERFACE BETWEEN INSULATION BARRIER AND BOTTOM HOUSING |
| 2B-205 | BOTTOM HALF OF ENCLOSURE/CASE | SEALING EDGE |
| 2B-206 | BOTTOM HALF OF ENCLOSURE/CASE | EXTERIOR TEXTURED OR COATED SURFACE |
| 2B-207 | BOTTOM HALF OF ENCLOSURE/CASE | POLISHED SURFACE OR REFLECTIVE COATED SURFACE INSIDE VACUUM CHAMBER |
| 2B-300 | TOP INSULATION BARRIER | COMPLETE PART |
| 2B-301 | TOP INSULATION BARRIER | INTERFACE BETWEEN INSULATION BARRIER AND TOP HOUSING |
| 2B-302 | TOP INSULATION BARRIER | SEALING INTERFACE WITH COORESPONDING INSULATION BARRIER |
| 2B-303 | TOP INSULATION BARRIER | AUTO-INJECTOR CONTACT SURFACE |
| 2B-400 | BOTTOM INSULATION BARRIER | COMPLETE PART |
| 2B-401 | BOTTOM INSULATION BARRIER | INTERFACE BETWEEN INSULATION BARRIER AND BOTTOM HOUSING |
| 2B-402 | BOTTOM INSULATION BARRIER | SEALING INTERFACE WITH COORESPONDING INSULATION BARRIER |
| 2B-403 | BOTTOM INSULATION BARRIER | AUTO-INJECTOR CONTACT SURFACE |
| 3A | TP/TPE CASE (FOR HOLDING 1 AUTO-INJECTOR WITH ATTACHMENT MEANS) | COMPLETE PART |
| 3A-100 | TP/TPE CASE (FOR HOLDING 1 AUTO-INJECTOR WITH ATTACHMENT MEANS) | HOUSING |
| 3A-101 | TP/TPE CASE (FOR HOLDING 1 AUTO-INJECTOR WITH ATTACHMENT MEANS) | LIP OR RESTRICTING FEATURE FOR SECURING AUTO-INJECTOR |
| 3A-102 | TP/TPE CASE (FOR HOLDING 1 AUTO-INJECTOR WITH ATTACHMENT MEANS) | EXTERNAL ATTACHMENT MECHANISM |
| 3A-103 | TP/TPE CASE (FOR HOLDING 1 AUTO-INJECTOR WITH ATTACHMENT MEANS) | BOTTOM SURFACE FOR ADDITION FIXATING (EX: ADHESIVE) |
| 3A-104 | TP/TPE CASE (FOR HOLDING 1 AUTO-INJECTOR WITH ATTACHMENT MEANS) | PERIMETER WALL |
| 3A-105 | TP/TPE CASE (FOR HOLDING 1 AUTO-INJECTOR WITH ATTACHMENT MEANS) | EXTERNAL SURFACE FOR LABELING/EMBOSING/TEXTURING/ COATING |
| 3A-106 | TP/TPE CASE (FOR HOLDING 1 AUTO-INJECTOR WITH ATTACHMENT MEANS) | AUTO-INJECTOR CONTACT SURFACE |
| 3B | TP/TPE CASE (FOR HOLDING MULTIPLE AUTO-INJECTORS WITH ATTACHMENT MEANS) | COMPLETE PART |
| 3B-100 | TP/TPE CASE (FOR HOLDING MULTIPLE AUTO-INJECTORS WITH ATTACHMENT MEANS) | HOUSING #1 |

-continued

| REFERENCE NUMERAL | NAME | DESCRIPTION |
|---|---|---|
| 3B-101 | TP/TPE CASE (FOR HOLDING MULTIPLE AUTO-INJECTORS WITH ATTACHMENT MEANS) | HOUSING #2 |
| 3B-102 | TP/TPE CASE (FOR HOLDING MULTIPLE AUTO-INJECTORS WITH ATTACHMENT MEANS) | LIP OR RESTRICTING FEATURE FOR SECURING AUTO-INJECTOR |
| 3B-103 | TP/TPE CASE (FOR HOLDING MULTIPLE AUTO-INJECTORS WITH ATTACHMENT MEANS) | EXTERNAL ATTACHMENT MECHANISM |
| 3B-104 | TP/TPE CASE (FOR HOLDING MULTIPLE AUTO-INJECTORS WITH ATTACHMENT MEANS) | PERIMETER WALL |
| 3B-105 | TP/TPE CASE (FOR HOLDING MULTIPLE AUTO-INJECTORS WITH ATTACHMENT MEANS) | EXTERNAL SURFACE FOR LABELING/EMBOSING/TEXTURING/COATING |
| 3B-106 | TP/TPE CASE (FOR HOLDING MULTIPLE AUTO-INJECTORS WITH ATTACHMENT MEANS) | AUTO-INJECTOR CONTACT SURFACE |
| 3C | TP/TPE CASE (FOR HOLDING 1 AUTO-INJECTOR ADAPTED FOR ATTACHMENT ON A SECONDARY DEVICE EX: CELL PHONE) | COMPLETE PART |
| 3C-100 | TP/TPE CASE (FOR HOLDING 1 AUTO-INJECTOR ADAPTED FOR ATTACHMENT ON A CELL PHONE) | HOUSING FOR AUTO-INJECTOR |
| 3C-101 | TP/TPE CASE (FOR HOLDING 1 AUTO-INJECTOR ADAPTED FOR ATTACHMENT ON A CELL PHONE) | HOUSING FOR SECONDARY DEVICE (EX: CELL PHONE) |
| 3C-102 | TP/TPE CASE (FOR HOLDING 1 AUTO-INJECTOR ADAPTED FOR ATTACHMENT ON A CELL PHONE) | RESTRAINING FEATURE FOR THE AUTO-INJECTOR |
| 3C-103 | TP/TPE CASE (FOR HOLDING 1 AUTO-INJECTOR ADAPTED FOR ATTACHMENT ON A CELL PHONE) | RESTRAINING FEATURE FOR THE SECONDARY DEVICE |
| 3C-104 | TP/TPE CASE (FOR HOLDING 1 AUTO-INJECTOR ADAPTED FOR ATTACHMENT ON A CELL PHONE) | CONTACT/BRACING SURFACE FOR THE AUTO-INJECTOR |
| 3C-105 | TP/TPE CASE (FOR HOLDING 1 AUTO-INJECTOR ADAPTED FOR ATTACHMENT ON A CELL PHONE) | EXTERNAL SURFACE FOR LABELING/EMBOSING/TEXTURING/COATING |
| 3C-106 | TP/TPE CASE (FOR HOLDING 1 AUTO-INJECTOR ADAPTED FOR ATTACHMENT ON A CELL PHONE) | HOUSING FOR LOW ASPECT RATION AUTO-INJECTOR |
| 3D | TP/TPE CASE (FOR HOLDING MULTIPLE AUTO-INJECTORS WITH ATTACHMENT MEANS) | COMPLETE PART |
| 3D-100 | TP/TPE CASE (FOR HOLDING MULTIPLE AUTO-INJECTORS WITH ATTACHMENT MEANS) | HOUSING FOR AUTO-INJECTOR |
| 3D-101 | TP/TPE CASE (FOR HOLDING MULTIPLE AUTO-INJECTORS WITH ATTACHMENT MEANS) | HOUSING FOR SECONDARY DEVICE (EX: CELL PHONE) |
| 3D-102 | TP/TPE CASE (FOR HOLDING MULTIPLE AUTO-INJECTORS WITH ATTACHMENT MEANS) | RESTRAINING FEATURE FOR THE AUTO-INJECTOR |
| 3D-103 | TP/TPE CASE (FOR HOLDING MULTIPLE AUTO-INJECTORS WITH ATTACHMENT MEANS) | RESTRAINING FEATURE FOR THE SECONDARY DEVICE |
| 3D-104 | TP/TPE CASE (FOR HOLDING MULTIPLE AUTO-INJECTORS WITH ATTACHMENT MEANS) | CONTACT/BRACING SURFACE FOR THE AUTO-INJECTOR |
| 3D-105 | TP/TPE CASE (FOR HOLDING MULTIPLE AUTO-INJECTORS WITH ATTACHMENT MEANS) | EXTERNAL SURFACE FOR LABELING/EMBOSING/TEXTURING/COATING |
| 3E | TP/TPE ADJUSTABLE STRAP CASE | COMPLETE PART |
| 3E-100 | TP/TPE ADJUSTABLE STRAP CASE | HOUSING FOR AUTO-INJECTOR |
| 3E-101 | TP/TPE ADJUSTABLE STRAP CASE | RESTRAINING FEATURE FOR THE AUTO-INJECTOR |
| 3E-102 | TP/TPE ADJUSTABLE STRAP CASE | CONTACT/BRACING SURFACE FOR THE AUTO-INJECTOR |
| 3E-103 | TP/TPE ADJUSTABLE STRAP CASE | EXTERNAL SURFACE FOR LABELING/EMBOSING/TEXTURING/COATING |
| 3E-104 | TP/TPE ADJUSTABLE STRAP CASE | ADJUSTABLE HOLES |
| 3E-105 | TP/TPE ADJUSTABLE STRAP CASE | FASTENING MECHANISM (EX: BUCKEL) |

-continued

| REFERENCE NUMERAL | NAME | DESCRIPTION |
|---|---|---|
| 3E-106 | TP/TPE ADJUSTABLE STRAP CASE | ATTACHMENST STRAPS FOR SECURING CASE |
| 3F | RIGID NON-VACUUM CASE WITH LINER | COMPLETE PART |
| 3F-100 | TOP HALF OF ENCLOSURE/CASE | FRICTION/INTERFERENCE/THREADED CONNECTION FOR BOTTOM HALF OF ENCLOSURE/CASE |
| 3F-101 | TOP HALF OF ENCLOSURE/CASE | UPPER RIGID HOUSING FOR FORMING THE CASE/ENCLOSURE |
| 3F-102 | TOP HALF OF ENCLOSURE/CASE | INTERFACE BETWEEN LINER/BARRIER AND UPPER HOUSING |
| 3F-103 | TOP HALF OF ENCLOSURE/CASE | SEALING EDGE |
| 3F-104 | TOP HALF OF ENCLOSURE/CASE | EXTERIOR TEXTURED OR COATED SURFACE |
| 3F-200 | BOTTOM HALF OF ENCLOSURE/CASE | FRICTION/INTERFERENCE/THREADED CONNECTION FOR BOTTOM HALF OF ENCLOSURE/CASE |
| 3F-201 | BOTTOM HALF OF ENCLOSURE/CASE | LOWER RIGID HOUSING FOR FORMING THE CASE/ENCLOSURE |
| 3F-202 | BOTTOM HALF OF ENCLOSURE/CASE | INTERFACE BETWEEN LINER/BARRIER AND BOTTOM HOUSING |
| 3F-203 | BOTTOM HALF OF ENCLOSURE/CASE | SEALING EDGE |
| 3F-204 | BOTTOM HALF OF ENCLOSURE/CASE | EXTERIOR TEXTURED OR COATED SURFACE |
| 3F-300 | UPPER LINER/BARRIER | COMPLETE PART |
| 3F-301 | UPPER LINER/BARRIER | INTERFACE BETWEEN LINER/BARRIER AND TOP HOUSING |
| 3F-302 | UPPER LINER/BARRIER | SEALING INTERFACE WITH COORESPONDING LINER/BARRIER |
| 3F-303 | UPPER LINER/BARRIER | AUTO-INJECTOR CONTACT SURFACE |
| 3F-304 | UPPER LINER/BARRIER | AUTO-INJECTOR ORIENTATION CUT-OUT |
| 3F-400 | LOWER LINER/BARRIER | COMPLETE PART |
| 3F-401 | LOWER LINER/BARRIER | INTERFACE BETWEEN LINER/BARRIER AND BOTTOM HOUSING |
| 3F-402 | LOWER LINER/BARRIER | SEALING INTERFACE WITH COORESPONDING INSULATION BARRIER |
| 3F-403 | LOWER LINER/BARRIER | AUTO-INJECTOR CONTACT SURFACE |
| 3F-404 | LOWER LINER/BARRIER | AUTO-INJECTOR ORIENTATION CUT-OUT |
| 3G | TP/TPE CASE (FOR HOLDING 1 OR MORE AUTO-INJECTORS WITH LINER) | COMPLETE PART |
| 3G-100 | TP/TPE CASE (FOR HOLDING 1 OR MORE AUTO-INJECTORS WITH LINER) | EXTERNAL HOUSING |
| 3G-101 | TP/TPE CASE (FOR HOLDING 1 OR MORE AUTO-INJECTORS WITH LINER) | RESTRICTING FEATURE FOR SECURING AUTO-INJECTOR AND INNER LINER |
| 3G-102 | TP/TPE CASE (FOR HOLDING 1 OR MORE AUTO-INJECTORS WITH LINER) | EXTERNAL ATTACHMENT MECHANISM |
| 3G-103 | TP/TPE CASE (FOR HOLDING 1 OR MORE AUTO-INJECTORS WITH LINER) | BOTTOM SURFACE FOR ADDITION FIXATING (EX: ADHESIVE) |
| 3G-104 | TP/TPE CASE (FOR HOLDING 1 OR MORE AUTO-INJECTORS WITH LINER) | PERIMETER WALL |
| 3G-105 | TP/TPE CASE (FOR HOLDING 1 OR MORE AUTO-INJECTORS WITH LINER) | EXTERNAL SURFACE FOR LABELING/EMBOSING/TEXTURING/COATING |
| 3G-106 | TP/TPE CASE (FOR HOLDING 1 OR MORE AUTO-INJECTORS WITH LINER) | FEATURE FOR AUTO-INJECTOR EASE OF REMOVAL |
| 3G-107 | TP/TPE CASE (FOR HOLDING 1 OR MORE AUTO-INJECTORS WITH LINER) | CUT-OUT(S) FOR LINER LABEL/EMBOSS/FEATURE |
| 3G-200 | TP/TPE CASE (FOR HOLDING 1 OR MORE AUTO-INJECTORS WITH LINER) | COMPLETE PART |
| 3G-201 | TP/TPE CASE (FOR HOLDING 1 OR MORE AUTO-INJECTORS WITH LINER) | HOUSING FOR AUTO-INJECTOR |
| 3G-202 | TP/TPE CASE (FOR HOLDING 1 OR MORE AUTO-INJECTORS WITH LINER) | SURFACE FOR LABELING/EMBOSING/TEXTURING/COATING |
| 3G-203 | TP/TPE CASE (FOR HOLDING 1 OR MORE AUTO-INJECTORS WITH LINER) | INTERFACE SURFACE WITH EXTERNAL SURFACE |
| 3H | ADJUSTABLE PROTECTIVE CASE | COMPLETE PART |
| 3H-100 | ADJUSTABLE PROTECTIVE CASE | ADJUSTABLE FEATURE FOR HOLDING AUTO-INJECTOR OR ADDITIONAL PROTECTIVE CASE |

-continued

| REFERENCE NUMERAL | NAME | DESCRIPTION |
|---|---|---|
| 3H-101 | ADJUSTABLE PROTECTIVE CASE | RESTRICTING/SECURING FEATURE |
| 3H-102 | ADJUSTABLE PROTECTIVE CASE | AUTO-INJECTOR POSITION ADJUSTMENT FEATURE (EX: BALL JOINT) |
| 3H-103 | ADJUSTABLE PROTECTIVE CASE | EXTERNAL MOUNTING FEATURE |
| 3H-104 | ADJUSTABLE PROTECTIVE CASE | INTERFACE BETWEEN AUTO-INJECTOR/CASE AND SECURING/RESTRICTING FEATURE |
| 3H-105 | ADJUSTABLE PROTECTIVE CASE | SUPPORT FEATURE FOR HOLDING AUTO-INJECTOR |

Each numerical value presented herein is contemplated to represent a minimum value or a maximum value in a range for a corresponding parameter. Accordingly, when added to the claims, the numerical value provides express support for claiming the range, which may lie above or below the numerical value, in accordance with the teachings herein. Every value between the minimum value and the maximum value within each numerical range presented herein (including in the charts shown in the figures), is contemplated and expressly supported herein, subject to the number of significant digits expressed in each particular range. Absent express inclusion in the claims, each numerical value presented herein is not to be considered limiting in any regard.

Unless expressly described elsewhere in this application, as used herein, when the term "substantially" or "about" is before a quantitative value, the present disclosure also includes the specific quantitative value itself, as well as, in various cases, a ±1%, ±2%, ±5%, and/or ±10% variation from the nominal value unless otherwise indicated or inferred.

Having described certain embodiments of the invention, it will be apparent to those of ordinary skill in the art that other embodiments incorporating the concepts disclosed herein may be used without departing from the spirit and scope of the invention. Accordingly, the described embodiments are to be considered in all respects as only illustrative and not restrictive. The terms and expressions employed herein are used as terms and expressions of description and not of limitation and there is no intention, in the use of such terms and expressions, of excluding any equivalents of the features shown and described or portions thereof. The structural features and functions of the various embodiments may be arranged in various combinations and permutations, and all are considered to be within the scope of the disclosed invention. Unless otherwise necessitated, recited steps in the various methods may be performed in any order and certain steps may be performed substantially simultaneously.

What is claimed is:

1. A protective case for enclosing a compact auto-injector used for delivering a medicament dose, the protective case comprising:
a lower portion comprising:
a double wall forming a void therebetween that forms a sealed lower vacuum chamber; and
a lower sidewall flange, wherein the lower vacuum chamber extends within at least a portion of the lower sidewall flange; and
a mating upper portion comprising:
a double wall forming a void therebetween that forms a sealed upper vacuum chamber; and
an upper sidewall flange, wherein the upper vacuum chamber extends within at least a portion of the upper sidewall flange;
such that when the lower portion and the upper portion are mated, the lower and upper sidewall flanges overlap to form a substantially sealed thermally isolated interior cavity for receiving the auto-injector.

2. The protective case of claim 1, wherein the case is substantially symmetrical about a horizontal plane.

3. The protective case of claim 1, wherein the case is substantially uniform about a central vertical axis.

4. The protective case of claim 1, wherein a pressure in each of the lower vacuum chamber and the upper vacuum chamber is less than about 0.1 torr.

5. The protective case of claim 1, wherein the lower portion and the upper portion are disk-shaped.

6. The protective case of claim 1, wherein the lower sidewall flange and the upper sidewall flange overlap at least one of axially, radially, and circumferentially.

7. The protective case of claim 1, wherein the lower sidewall flange and the upper sidewall flange overlap axially, radially, and circumferentially.

8. The protective case of claim 1, wherein mating surfaces of the lower sidewall flange and the upper sidewall flange at least one of (i) form a threaded interface or (ii) are sized to maintain a sliding interference fit.

9. The protective case of claim 1, further comprising at least one of a lower insulating ring disposed about an interior perimeter of the lower sidewall flange and an upper insulating ring disposed about an interior perimeter of the upper sidewall flange.

10. The protective case of claim 9, wherein the insulating ring comprises a material selected from the group consisting of a closed cell polymer foam, an open cell polymer foam, rubber, TP, TPE, and combinations thereof.

11. The protective case of claim 1, further comprising at least one of a lower stabilizing element disposed within the lower portion and an upper stabilizing element disposed within the upper portion to support the auto-injector when disposed in the interior cavity.

12. The protective case of claim 11, wherein the stabilizing element comprises a material selected from the group consisting of a closed cell polymer foam, an open cell polymer foam, rubber, TP, TPE, and combinations thereof.

13. The protective case of claim 1, wherein the protective case comprises a material selected from the group consisting of metal, polymer, a composite material, a ceramic, and combinations thereof.

14. The protective case of claim 1, further comprising an attachment device to facilitate a user carrying the case.

15. The protective case of claim 14, wherein the attachment device comprises an element selected from the group consisting of an adjustable elastic strap, a non-elastic strap, a wrist strap, a wrist band, a clip, a tether, a necklace, a pin, a clamp, a mount, a tab forming an eyelet, an adhesive layer, a hand grip surface, and combinations thereof.

16. The protective case of claim 1, further characterized by an absence of active thermal control of the interior cavity.

17. The protective case of claim 1, wherein, when the lower portion and the upper portion are mated, the substantially sealed thermally isolated interior cavity is at least one of substantially watertight and substantially water resistant.

18. The protective case of claim 1, further comprising an external surface selected from the group consisting of a coating, an embossed surface, a ribbed surface, a grip, and combinations thereof.

19. The protective case of claim 1, further comprising a reflective coating disposed on an interior surface of the lower vacuum chamber and the upper vacuum chamber.

20. The protective case of claim 1, wherein the interior cavity is adapted to receive multiple autoinjectors.

21. The apparatus of claim 1, wherein the protective case forms a second cavity for receiving a second device.

22. The apparatus of claim 21, wherein the second device is selected from the group consisting of a cell phone and a second auto-injector device.

23. The apparatus of claim 1, wherein the interior cavity circumscribes at least a portion of the auto-injector device.

24. A method of thermally isolating a compact auto-injector containing a medicament dose from ambient environmental temperatures, the method comprising the steps of:
   providing a protective case comprising:
      a lower portion comprising:
         a double wall forming a void therebetween that forms a sealed lower vacuum chamber; and
         a lower sidewall flange, wherein the lower vacuum chamber extends within at least a portion of the lower sidewall flange; and
      a mating upper portion comprising:
         a double wall forming a void therebetween that forms a sealed upper vacuum chamber; and
         an upper sidewall flange, wherein the upper vacuum chamber extends within at least a portion of the upper sidewall flange;
   placing the auto-injector into an interior cavity portion formed by at least one of the lower portion and the upper portion; and
   mating the lower and upper sidewall flanges in overlapping relation to form a substantially sealed thermally isolated interior cavity for the auto-injector.

25. The method of claim 24, further comprising the step of providing an attachment device to associate the protective case with a user.

26. The method of claim 25, wherein the attachment device comprises an element selected from the group consisting of an adjustable elastic strap, a non-elastic strap, a wrist strap, a wrist band, a clip, a tether, a necklace, a pin, a clamp, a mount, a tab forming an eyelet, an adhesive layer, a hand grip surface, and combinations thereof.

27. The method of claim 24, further characterized by an absence of actively thermally controlling the interior cavity.

28. The method of claim 24, wherein the protective case forms a second cavity for receiving a second device.

29. The method of claim 28, wherein the second device is selected from the group consisting of a cell phone and a second auto-injector device.

30. The method of claim 24, wherein the interior cavity circumscribes at least a portion of the auto-injector device.

* * * * *